US012013572B2

(12) United States Patent
Vakoc et al.

(10) Patent No.: US 12,013,572 B2
(45) Date of Patent: Jun. 18, 2024

(54) APPARATUS AND METHODS FOR HIGH-SPEED AND LONG DEPTH RANGE IMAGING USING OPTICAL COHERENCE TOMOGRAPHY

(71) Applicant: The General Hospital Corporation, Boston, MA (US)

(72) Inventors: Benjamin Vakoc, Arlington, MA (US); Meena Siddiqui, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 79 days.

(21) Appl. No.: 17/708,143

(22) Filed: Mar. 30, 2022

(65) Prior Publication Data

US 2022/0221267 A1 Jul. 14, 2022

Related U.S. Application Data

(63) Continuation of application No. 17/106,690, filed on Nov. 30, 2020, now Pat. No. 11,320,256, which is a
(Continued)

(51) Int. Cl.
*H03M 1/12* (2006.01)
*A61B 5/00* (2006.01)
(Continued)

(52) U.S. Cl.
CPC .......... *G02B 6/2932* (2013.01); *A61B 5/0066* (2013.01); *G01B 9/02091* (2013.01);
(Continued)

(58) Field of Classification Search
CPC ... G02B 6/2932; A61B 5/0066; A61B 5/6826; G01B 9/02091; G01B 9/02002;
(Continued)

(56) References Cited

U.S. PATENT DOCUMENTS

| 5,926,277 A | 7/1999 | Marron |
| 7,355,716 B2 | 4/2008 | De Boer |
(Continued)

FOREIGN PATENT DOCUMENTS

| CN | 102469936 A | 5/2012 |
| CN | 102628799 A | 8/2012 |
(Continued)

OTHER PUBLICATIONS

Choi et al., Spectral Domain Optical Coherence Tomography of Multi-MHz A-Scan Rates at 1310 nm Range and Real-Time 4D-Display up to 41 Volumes/Second, Biomedical Optics Express, 2012, 3(12):3067-3086.
(Continued)

*Primary Examiner* — Jean B Jeanglaude
(74) *Attorney, Agent, or Firm* — Quarles & Brady LLP

(57) ABSTRACT

Exemplary apparatus can be provided which can include a laser arrangement that is configured to provide a laser radiation, and including an optical cavity. The optical cavity can include a dispersive optical waveguide first arrangement having first and second sides, and which is configured to (i) receive at least one first electro-magnetic radiation at the first side so as to provide at least one second electro-magnetic radiation, and (ii) to receive at least one third electro-magnetic radiation at the second side so as to provide at least one fourth electro-magnetic radiation. The first and second sides are different from one another, and the second and third radiations are related to one another. The optical cavity can also include an active optical modulator second arrangement which can be configured to receive and modulate the fourth radiation so as to provide the first electro-magnetic radiation to the first arrangement. The laser radiation can be associated with at least one of the first, second, third or fourth radiations.

16 Claims, 43 Drawing Sheets

Related U.S. Application Data continuation of application No. 16/077,294, filed as application No. PCT/US2017/017664 on Feb. 13, 2017, now Pat. No. 10,852,121.

(60) Provisional application No. 62/310,365, filed on Mar. 18, 2016, provisional application No. 62/294,822, filed on Feb. 12, 2016.

(51) Int. Cl.
*G01B 9/02091* (2022.01)
*G01K 11/32* (2021.01)
*G02B 6/293* (2006.01)
*H01S 3/067* (2006.01)
*H03M 1/20* (2006.01)
*H01S 3/08* (2023.01)
*H01S 3/106* (2006.01)

(52) U.S. Cl.
CPC ............ *G01K 11/32* (2013.01); *H01S 3/0675* (2013.01); *H03M 1/20* (2013.01); *A61B 5/6826* (2013.01); *H01S 3/06791* (2013.01); *H01S 3/08086* (2013.01); *H01S 3/106* (2013.01); *H01S 3/1062* (2013.01)

(58) Field of Classification Search
CPC ... G01K 11/32; H01S 3/0675; H01S 3/06791; H01S 3/08086; H01S 3/106; H01S 3/1062; H03M 1/20
USPC ........................................................ 341/155
See application file for complete search history.

(56) References Cited

U.S. PATENT DOCUMENTS

| | | | |
|---|---|---|---|
| 7,561,605 | B1 | 7/2009 | Delfyett et al. |
| 9,087,368 | B2 | 7/2015 | Tearney |
| 10,852,121 | B2 | 12/2020 | Vakoc et al. |
| 2002/0012472 | A1 | 1/2002 | Waterfall |
| 2002/0122246 | A1 | 9/2002 | Tearney |
| 2002/0168141 | A1 | 11/2002 | Verdrager |
| 2002/0196816 | A1 | 12/2002 | Shirasaki |
| 2003/0174743 | A1 | 9/2003 | Cliche |
| 2004/0037505 | A1 | 2/2004 | Morin |
| 2005/0007602 | A1 | 1/2005 | Haidner et al. |
| 2005/0018201 | A1 | 1/2005 | De Boer |
| 2005/0063430 | A1 | 3/2005 | Doucet |
| 2005/0215985 | A1 | 9/2005 | Mielke et al. |
| 2006/0093276 | A1 | 5/2006 | Bouma |
| 2006/0244973 | A1 | 11/2006 | Yun |
| 2007/0035743 | A1 | 2/2007 | Vakoc |
| 2009/0046295 | A1* | 2/2009 | Kemp ................... A61B 5/6852 356/479 |
| 2009/0289042 | A1 | 11/2009 | Ueda |
| 2009/0290828 | A1 | 11/2009 | Shimizu |
| 2010/0150422 | A1 | 6/2010 | Vakoc |
| 2011/0150293 | A1 | 6/2011 | Bower et al. |
| 2011/0206072 | A1 | 8/2011 | Karavitis |
| 2011/0222563 | A1 | 9/2011 | Bouma |
| 2012/0044971 | A1 | 2/2012 | Omichi |
| 2012/0099113 | A1 | 4/2012 | de Boer et al. |
| 2012/0230354 | A1 | 9/2012 | Huber et al. |
| 2013/0310643 | A1 | 11/2013 | Gora |
| 2014/0176963 | A1* | 6/2014 | Kemp ................. G01B 9/02048 356/497 |
| 2015/0055136 | A1* | 2/2015 | Huber ................. G01B 9/02004 356/479 |
| 2015/0253645 | A1 | 9/2015 | Coddington |
| 2016/0157721 | A1 | 6/2016 | Vakoc |

FOREIGN PATENT DOCUMENTS

| | | |
|---|---|---|
| CN | 104271031 A | 1/2015 |
| JP | 2010016270 A | 1/2010 |
| JP | 2013092544 A | 5/2013 |
| JP | 2013142667 A | 7/2013 |
| WO | 2005047813 A1 | 5/2005 |
| WO | 2012088320 A2 | 6/2012 |
| WO | 2015013651 A2 | 1/2015 |

OTHER PUBLICATIONS

Zhang et al., Real-Time Intraoperative 4D Full-Range FD-OCT Based on the Dual Graphics Processing Units Architecture for Microsurgery Guidance, Biomedical Optics Express, 2011, 2(4):764-770.
Australian Government—IP Australia, Examination Report No. 1, Application No. 2021261928, Feb. 7, 2023, 9 pages.
Canadian Intellectual Property Office, Office Action, Application No. 3,014,324, Feb. 21, 2023, 8 pages.
Mandridis et al., Semiconductor-Based Low Noise 100 MHz Chirped Pulse Laser Source Based on a Theta Cavity Design with an Intra-Cavity Etalon and Long-Term Stabilization, Proc. of SPIE, 2011, vol. 8054, pp. 805401-1 thru 805401-7.
European Patent Office, Communication, Application No. 17750960.1, Nov. 22, 2022, 8 pages.
Japan Patent Office, Notice of Reasons for Refusal, Application No. 2018-542747, May 13, 2022, 8 pages.
China National Intellectual Property Administration, Notice of the First Office Action for application 201780023073.4, mailed on Dec. 26, 2019. With Translation.
Choma, M. A., et al. "Instantaneous quadrature low-coherence interferometry with 3x 3 fiber-optic couplers." Optics letters 28.22 (2003): 2162-2164.
European Patent Office, Extended European Search Report for application 17750960.1, dated Mar. 4, 2020.
European Patent Office, Partial Supplementary European Search Report for application 17750960.1, dated Sep. 30, 2019.
Haus, H. A., et al. Stretched-pulse additive pulse mode-locking in fiber ring laser: theory and experiment. IEEE J. Quantum Electron. 31, 591-598 (1995).
International Searching Authority, International Search Report and Written Opinion for application PCT/US2017/017664, mailed on Jun. 9, 2017.
Japan Patent Office. Notification of Reasons for Refusal for application 2018-542747. Dated Sep. 8, 2020. With Translation.
Kim, K. et al. "extreme chirped pulse amplification-beyond the fundamental energy storage limit of semiconductor optical amplifiers." IEEE Journal of selected topics in quantum electronics 12.2 (2006): 245-254.
Kim, K. H., et al. "Two-axis magnetically-driven MEMS scanning catheter for endoscopic high-speed optical coherence tomography." Optics express 15.26 (2007): 18130-18140.
Lee, S. et al. "Extreme chirped pulse oscillator (XCPO) using a theta cavity design." IEEE photonics technology letters 18.7 (2006): 799-801.
Lee, S. et al. "extreme chirped pulse oscillator operating in the nanosecond stretched pulse regime." Optics express 16.7 (2008): 4766-4773.
Mandridis, D., et al. "Low noise chirped pulse mode-locked laser using an intra-cavity Fabry-Perot etalon." Optics Express 19.10 (2011): 8994-8999.
Siddiqui, M, et al. "Compensation of spectral and RF errors in swept-source OCT for high extinction complex demodulation." Optics express 23.5 (2015): 5508-5520.
Siddiqui, M, et al. Optical-domain subsampling for data efficient depth ranging in Fourier-domain optical coherence tomography. Opt. Express 20, 17938-17951 (2012).
Tamura, K., et al. 77-fs pulse generation from a stretched-pulse mode-locked all-fiber ring laser. Opt. Lett. 18, 1080-1082 (1993).
U.S. Appl. No. 61/589,083.
Vakoc, B. J., et al. "Elimination of depth degeneracy in optical frequency-domain imaging through polarization-based optical demodulation." Optics letters 31.3 (2006): 362-364.

(56) References Cited

OTHER PUBLICATIONS

Yezzi, A, et al. "A geometric snake model for segmentation of medical imagery." IEEE Transactions on medical imaging 16.2 (1997): 199-209.
Tozubrun, S., et al. A rapid, dispersion-based wavelength-stepped and wavelength-swept laser for optical coherence tomography. Opt. Express 22, 3414-3424 (2014).
Korean Intellectual Property Office, Notice of Preliminary Rejection, Application No. 10-2018-7026235, Jun. 8, 2023, 12 pages.
Japan Patent Office, Notification of Reasons for Refusal for application 2018-542747, dated Jul. 6, 2021, with translation (9 pages).
China National Intellectual Property Administration, Second Office Action, Application No. 201780023073.4, Oct. 9, 2020, 9 pages.
China National Intellectual Property Administration, Third Office Action, Application No. 201780023073.4, Jul. 6, 2021, 6 pages.
IP Australia. Examination report No. 1 for standard patent application 2017218007. Mailed on May 14, 2021. 4 pages.
China National Intellectual Property Administration, First Office Action and Search Report, Application No. 202210142915.0, Dec. 21, 2023, 13 pages.
Australian Government—IP Australia, Examination Report No. 2, Application No. 2021261928, Aug. 29, 2023, 4 pages.

* cited by examiner

APPARATUS AND METHODS FOR HIGH-SPEED AND LONG DEPTH RANGE IMAGING USING OPTICAL COHERENCE TOMOGRAPHY

CROSS-REFERENCE TO RELATED APPLICATION(S)

The present application is a continuation of U.S. patent application Ser. No. 17/106,690 filed Nov. 30, 2020, which is a continuation of U.S. patent application Ser. No. 16/077,294 filed Aug. 10, 2018, which issued as U.S. Pat. No. 10,852,121 on Dec. 1, 2020, and which is a U.S. National Stage of PCT Application No. PCT/US2017/017664 filed on Feb. 13, 2017, which relates to and claims priority from U.S. Patent Application Ser. No. 62/294,822 filed Feb. 12, 2016, and U.S. Patent Application Ser. No. 62/310,365 filed Mar. 18, 2016. Each of the preceding patent applications is hereby incorporated herein by reference in its entirety.

STATEMENT REGARDING FEDERALLY SPONSORED RESEARCH

This invention was made with government support under RR032042 awarded by the National Institutes of Health, and FA9550-13-1-0068 awarded by the Air Force Office of Scientific Research. The government has certain rights in the invention.

FIELD OF THE DISCLOSURE

The present disclosure relates to optical imaging systems, and more specifically apparatus and method related to high-speed imaging of the three-dimensional scattering properties of a sample located within a large imaging volume, and especially to rapid depth-resolved imaging of a sample that has a geometric structure that causes the distance of each region of sample relative to the imaging system to vary across the sample and over time.

BACKGROUND INFORMATION

Optical coherence tomography (OCT) provides cross-sectional images of biological samples with resolution on the scale of several to tens of microns. Conventional OCT, referred to as time-domain OCT ("TD-OCT"), can use low-coherence interferometry techniques to achieve depth ranging. In contrast, Fourier-Domain OCT ("FD-OCT") techniques can use spectral-radar techniques to achieve depth ranging. FD-OCT techniques have been shown to facilitate higher imaging speeds through improved signal-to-noise performance and elimination of a mechanically scanned interferometer reference arm.

FD-OCT systems generally operate by separating a light source into a sample beam and a reference beam. The sample beam can be directed at a sample to be imaged, and the reflected light from the sample is recombined with light from the reference beam (i.e., returning from the reference arm), resulting in an interference signal, which can provide information about the structure, composition and state, for example, of the sample. Light in the sample path and or light in the reference path can be modified by, for example, a phase modulator or frequency shifter, altering the characteristics of the interference and enhancing the information content of the signal or making the signal easier to detect. FD-OCT systems can sample the interference signal as a function of wavelength.

In one exemplary embodiment of the FD-OCT system, the interference signal as a function of wavelength can be obtained by using a light source that has an output wavelength which sweeps, varies or steps as a function of time. A detection of the interference signal as a function of time thereby can yield the interference signal as a function of wavelength. This exemplary embodiment can be referred to as optical frequency domain imaging ("OFDI") technique.

In another exemplary embodiment of the FD-OCT system, the interference signal as a function of wavelength can be obtained by using a broadband light source and a spectrally dispersing unit or a spectrometer that spatially separates the recombined sample and reference light according to wavelength such that a one-dimensional or two-dimensional camera can sample the signal as a function of the wavelength. This exemplary embodiment can be referred to as spectral-domain OCT technique. In both such exemplary embodiments, the detected interference signal as a function of wavenumber k (k=1/wavelength) can be used to provide information related to the depth profile of scattering in a turbid or semi-turbid sample, or a transparent sample. Such information can include information regarding, e.g., the structure of the sample, composition, state, flow, and birefringence.

A scatterer at a given depth can induce a modulation in the amplitude or polarization of the interfered signal. The frequency of such modulation in wavenumber-space can be related to the location of the scatter or the time delay of the light reflected from that scatter relative to the time delay of the light in the reference arm. Scatterers located at a depth that causes reflected signals with no net time delay relative to the reference arm light can induce an interference signal that may not modulate with wavenumber. As the location of the scatterers moves from this zero-delay point, the magnitude of the frequency can increase. To image over large delay windows, e.g., to detect and localize reflections within large time delay window, the interference signal may often be sampled with sufficiently high resolution in wavenumber-space to facilitate an unambiguous detection of the range of modulation frequencies that are associated with the large delay window.

To accommodate the sampling at high resolution in wavenumber, increasingly fast analog-to-digital converters ("ADC") can be used in the OFDI systems, and increasingly high pixel count cameras can be used in the SD-OCT systems. In both the OFDI and SD-OCT systems, the increased data volume resulting from imaging over large extents can often result in the use of increasingly-high bandwidth data transfer buses and data storage units.

Optical-domain subsampling can be used to increase the depth range of an OFDI or SD-OCT system without increasing the number of spectral measurements that are performed. In addition, optical-domain subsampling can be used to increase the imaging speed without increasing the electrical bandwidth of the imaging system. In this manner, an optical-domain subsampling OCT system can interrogate a larger volume of physical space with a given number of measurements than a FD-OCT or a SD-OCT system that is operated with the same number of measurements.

In a high-speed optical domain subsampled OCT system, it is possible to image across large depth ranges at extremely high speeds resulting in video-rate volumetric microscopy of samples that are not precisely located relative to the imaging system or contain a surface that varies in distance to the imaging system across the field.

Accordingly, there is a need to address and/or overcome at least some of the deficiencies described herein above.

SUMMARY OF EXEMPLARY EMBODIMENTS

In particular, at least some of the deficiencies with the conventional systems and method can be addressed with an exemplary apparatus which can include a laser arrangement that is configured to provide a laser radiation, and including an optical cavity. The optical cavity can include a dispersive optical waveguide first arrangement having first and second sides, and which is configured to (i) receive at least one first electro-magnetic radiation at the first side so as to provide at least one second electro-magnetic radiation, and (ii) to receive at least one third electro-magnetic radiation at the second side so as to provide at least one fourth electro-magnetic radiation. The first and second sides are different from one another, and the second and third radiations are related to one another. The optical cavity can also include an active optical modulator second arrangement which can be configured to receive and modulate the fourth radiation so as to provide the first electro-magnetic radiation to the first arrangement. The laser radiation can be associated with at least one of the first, second, third or fourth radiations.

In one exemplary embodiment, the first arrangement can be a fiber Bragg grating (FBG), a chirped FBG, and/or a FBG array. The FBG can be provided in a polarization maintaining optical fiber and/or a non-polarization maintaining optical fiber. The first arrangement can also be configured to cause a group delay that varies linearly with an optical frequency of the first radiation and/or the third radiation. According to another exemplary embodiment, the first arrangement can include (i) at least one first circulator which receives the first radiation and transmits the second radiation, and/or (ii) at least one second circulator which receives the third radiation and transmits the fourth radiation. The optical cavity can include at least one optical amplifier third arrangement which can be configured to amplify at least one of the first radiation, the second radiation, the third radiation or the fourth radiation. The optical amplifier arrangement can include a semiconductor amplifier, a Raman amplifier, a parametric optical amplifier, and/or a fiber amplifier. The optical cavity can also include a further active optical modulator fourth arrangement which can be configured to receive and modulate the second radiation so as to provide the third electro-magnetic radiation to the first arrangement. For example, the further active optical modulator fourth arrangement can be configured to suppress a light radiation that travels through the first arrangement, which is different from the second radiation. Additionally or alternatively, the further active optical modulator fourth arrangement can be a further active optical amplifier arrangement.

According to a further exemplary embodiment of the present disclosure, the optical cavity can include at least one optical polarizer fifth arrangement, which is configured to block a light radiation transmitted through the first arrangement. The optical cavity can also include a dispersion compensating arrangement and/or a fixed periodic spectral filter arrangement. The fixed periodic spectral filter arrangement can include (i) a Fabry-Perot etalon filter that has a finesse that is between 3 and 25, and/or (ii) an optical interleaver. The Fabry-Perot etalon filter can be an air gap etalon filter.

In a still further exemplary embodiment of the present disclosure, the laser radiation can have a wavelength that changes over time, e.g., continuously and/or discretely. For example, actions by the first and second arrangements can cause the wavelength to change at a rate that is faster than 80 nm/micro seconds.

In further alternative embodiments, the first arrangement can include a fiber Bragg grating (FBG) that is provided in a polarization maintaining optical waveguide, the first radiation can be launched along a first birefringent axis of the optical waveguide, and the third radiation can be launched along a second birefringent axis of the optical waveguide, with the first and second birefringent axes being different from one another. The second electro-magnetic radiation can be a reflection of the first electro-magnetic radiation, and the fourth electro-magnetic radiation can be a reflection of the third electro-magnetic radiation.

According to yet another exemplary embodiment of the present disclosure, an exemplary apparatus can be provided which can include a laser arrangement that is configured to provide a laser radiation, and including an optical cavity. The optical cavity can include a dispersive first arrangement can be configured to receive at least one first electro-magnetic radiation so as to provide at least one second electro-magnetic radiation, and a dispersive second arrangement which is configured to receive at least one third electro-magnetic radiation so as to provide at least one fourth electro-magnetic radiation, whereas the second and third radiations are related to one another. The optical cavity can further include an active optical modulator second arrangement which can be configured to receive and modulate the fourth radiation so as to provide the electro-magnetic radiation to the first arrangement, with the laser radiation being associated with at least one of the first, second, third or fourth radiations. The laser arrangement can also include an interferometer arrangement which is configured to generate (i) a fifth electro-magnetic radiation from the laser radiation in a sample arm, (ii) a sixth electro-magnetic radiation from the laser radiation in a reference arm, and (iii) an interference signal based on an interference between the fifth electro-magnetic radiation and the sixth electro-magnetic radiation. The laser arrangement can also include a beam scanning arrangement configured to scan the fifth electro-magnetic radiation across at least one portion of at least one sample. An interaction between the laser arrangement, the interferometer arrangement, and the beam scanning arrangement provides a three-dimensional measurement of an optical property of the portion(s) of the sample(s).

For example, according to one exemplary embodiment, the laser arrangement can further include an analog-to-digital acquisition arrangement configured to obtain the interference signal based on an electronic clock signal, and an electronic signal generator configured to drive the second arrangement, whereas the electronic clock signal can be phase-locked to the electronic signal generator. The first and second arrangements can include fiber Bragg gratings or part of the same fiber Bragg grating. The second electro-magnetic radiation can be a reflection of the first electro-magnetic radiation, and the fourth electro-magnetic radiation can be a reflection of the third electro-magnetic radiation. The laser radiation can be an optical frequency comb.

According to yet another exemplary embodiment of the present disclosure, an exemplary apparatus can be provided which can include a laser arrangement that is configured to generate a laser radiation at a particular number (N) of discrete optical frequencies. The exemplary apparatus cam also include an interferometer arrangement configured to generate an interference signal from the laser radiation, and a beam scanning arrangement configured to scan at least one portion of the laser radiation across at least one portion of at least one sample. A line width of each of the discrete optical frequencies can be less than 10 GHz, and a spacing between each of the discrete optical frequencies can be greater than 20 GHz. The laser radiation can step between the discrete optical frequencies at rate that is greater than 20 million discrete optical frequency steps per second. In a further exemplary embodiment of the present disclosure, the laser arrangement can include a continuous fiber Bragg grating having a length that is greater than 2 meters, and or a fiber Bragg grating array having a length that is greater than 2 meters.

According to a still further exemplary embodiment of the present disclosure, method computer-accessible medium (e.g., having software stored thereof to be executed by a computer) can be provided for displaying a video stream regarding at least one structure. For example, using such method and computer-accessible medium, it is possible to measure four-dimensional interferometric data regarding different portions of at least one structure at different points in time, wherein the four-dimensional data describing at least one optical property of the at least one structure. Further, it is possible to transform the four-dimensional interferometric data into two-dimensional video data, and display the video stream of the different portions of the structure using the two-dimensional video data. A latency of a performance of the measurement and the display is less than 1 second.

The exemplary procedures performed by such exemplary method and computer are done so in a medical procedure, and further can cause the procedure to be guided interactively using the video stream. Additionally, the measurement can be performed using a frequency comb optical source. Alternatively or additionally, the measurement can be performed using a laser arrangement as described in various embodiments herein above.

According to a still further exemplary embodiment of the present disclosure, method computer-accessible medium (e.g., having software stored thereof to be executed by a computer) can be provided to be used in a medical procedure on at least one anatomical structure. Using such exemplary method and computer, it is possible to measure single-dimensional interferometric data describing at least one optical property of the structure at a rate that greater than 5 Mega Hertz. Further, it is possible to construct four-dimensional interferometric data from the single-dimensional interferometric data regarding different portions of at least one structure at different points in time, and utilize the four-dimensional interferometric data in the medical procedure. For example, the measurement can be performed using a frequency comb optical source. Alternatively or additionally, the measurement can be performed using a laser arrangement as described in various embodiments herein above.

According to a yet still further exemplary embodiment of the present disclosure, method computer-accessible medium (e.g., having software stored thereof to be executed by a computer) can be provided for displaying a video stream regarding at least one structure. For example, using such method and computer-accessible medium, it is possible to measure four-dimensional interferometric data regarding different portions of at least one structure at different points in time, whereas the four-dimensional data describing at least one optical property of the structure, and the four-dimensional interferometric data can be circularly wrapped in a particular spatial dimension. Additionally, the exemplary method and computer can transform the four-dimensional interferometric data into two-dimensional video data by compressing the particular spatial dimension, and display the video stream of the different portions of the structure using the two-dimensional video data.

For example, the compression can include (i) locating a position of a surface of the structure within the four-dimensional interferometric data, and (ii) controlling the compression using the position. Further, the measurement can be is performed using a frequency comb optical source, and/or a laser arrangement as described in various embodiments herein above.

These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which.

Figure 1:
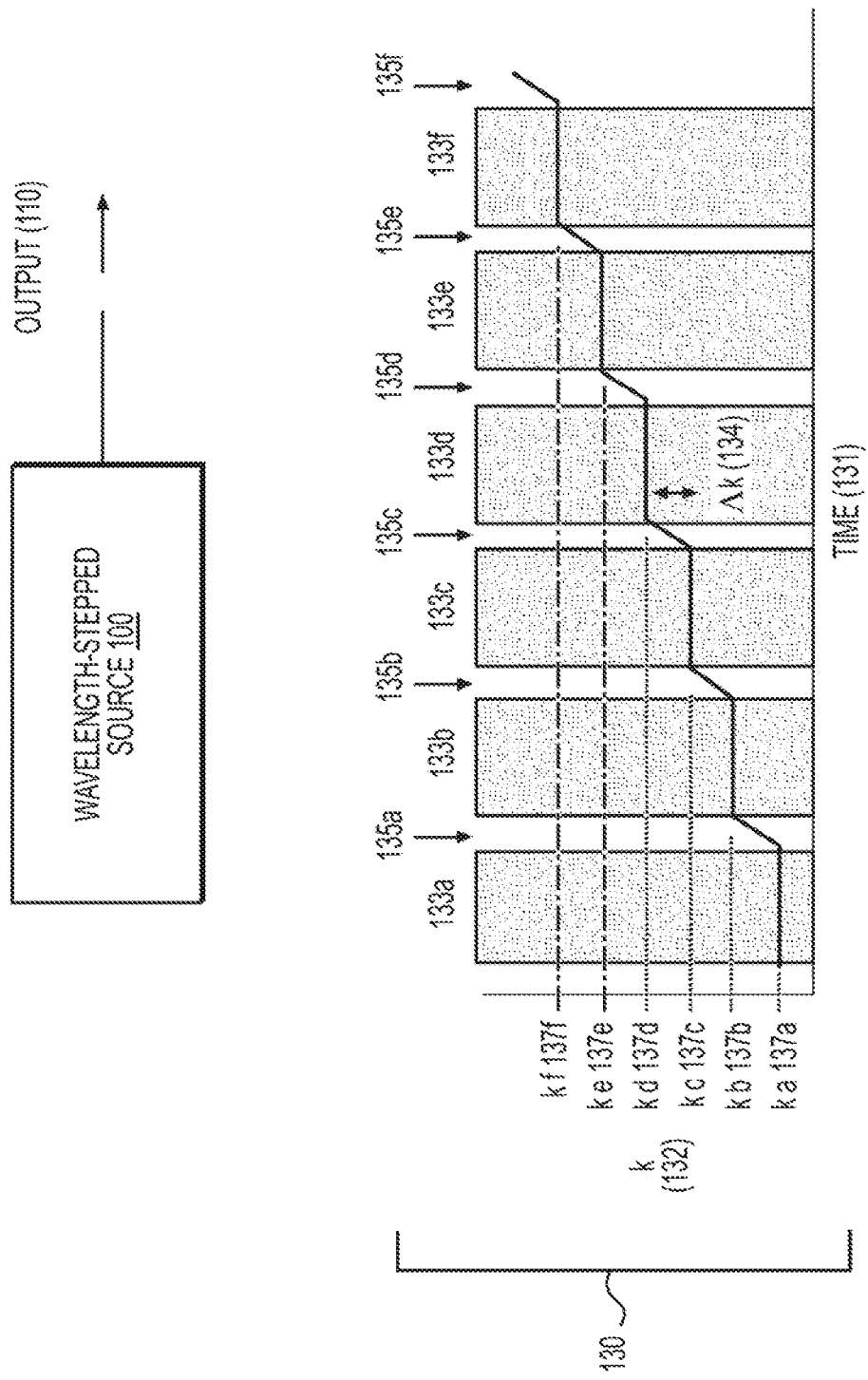
FIG. 1 is an exemplary illustration of a relationship between frequency content of an exemplary wavelength-stepped laser and time.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure and the appended claims.

DETAILED DESCRIPTION OF EXEMPLARY EMBODIMENT

Optical-domain subsampled OCT is referred hereafter to as optically subsampled OCT (OS-OCT). In one exemplary embodiment of the present disclosure, an imaging system can be provided that is based on optical frequency domain imaging (OFDI). Unlike conventional OCT systems that utilize wavelength-swept sources wherein the source wavelength varies substantially continuously with time, OS-OCT can use a wavelength-stepped source, where the source has a wavelength that varies in a stepwise fashion with discrete jumps in wavelength separating periods wherein the wavelength is substantially constant.

FIG. 1 illustrates an exemplary illustration of a relationship between frequency content of an exemplary wavelength-stepped laser and time. Such exemplary illustration of FIG. 1 shows the output wavenumber as a function of time of an exemplary wavelength-stepped source 100. This source can include an optical output 110 that can be time-varying in wavenumber. An exemplary wavenumber 132 versus time 131 trace is provided in plot 130. The exemplary trace can be characterized by periods of stability in the k of the laser 133a-133f separated by periods during which the source wavenumber is rapidly switching 135a-135f. The step size in wavenumber-space can be given as Δk 134. Alternatively or additionally, the wavelengths may not necessarily be equally spaced in wavenumber and there could be a range of Δk spacings in the source. Each of stable periods 133a-133f can define a wavenumber value k_a to k_f (137a-137f) for a specific channel of the source. The period of stability can occupy a variable percentage of the time gap between adjacent wavenumbers; for example it can fill the entire time gap and the laser can jump directly from one wavenumber to the next, or it can be a short pulse where the laser power is turned off until the next wavenumber. The exemplary plot 130 includes 6 channels, which can be a subset of the total channel count of the source, or the source can include less distinct wavenumber outputs such as for example two. The output power of the source is designed to yield appreciable power in each of the channels.

The power trace can be flat as a function of wavelength, and/or can vary according to, for example, the spectral response of the gain medium used in the source, or can be made to follow a particular profile. During the times 135a-135f between wavelengths, the power of the exemplary laser source can be modulated and/or turned off. While the wavenumber output shown in FIG. 1 indicates a monotonically increasing wavenumber, the wavenumber 137a-137f can follow non-monotonic orders such as for example the output wavenumbers may occur in descending monotonic order, or in a non-monotonic order such as, for example, in the order: 137a, then 137d, then 137f, then 137e, then 137b, then 137c. In one exemplary embodiment of the present disclosure, the source outputs wavelengths in the OCT imaging bands can be approximately centered at 800 nm, 1.0 μm, 1.3 μm, 1.5 m, 1.6 μm, or 1.7 μm. In further exemplary embodiments, it is possible to operate at any optical range including those in the UV and visible bands. In another exemplary embodiment of the present disclosure, the source can output wavelengths that are grouped into two or more spectral regions. For example, wavelengths within 1.0-1.1 m can be output followed by wavelengths from 1.3-1.4 μms. Alternatively, an exemplary source that yields multiple wavenumber stepped outputs within each of the red, green, and blue visible spectra can be used according to an exemplary embodiment of the present disclosure.

Figure 2:
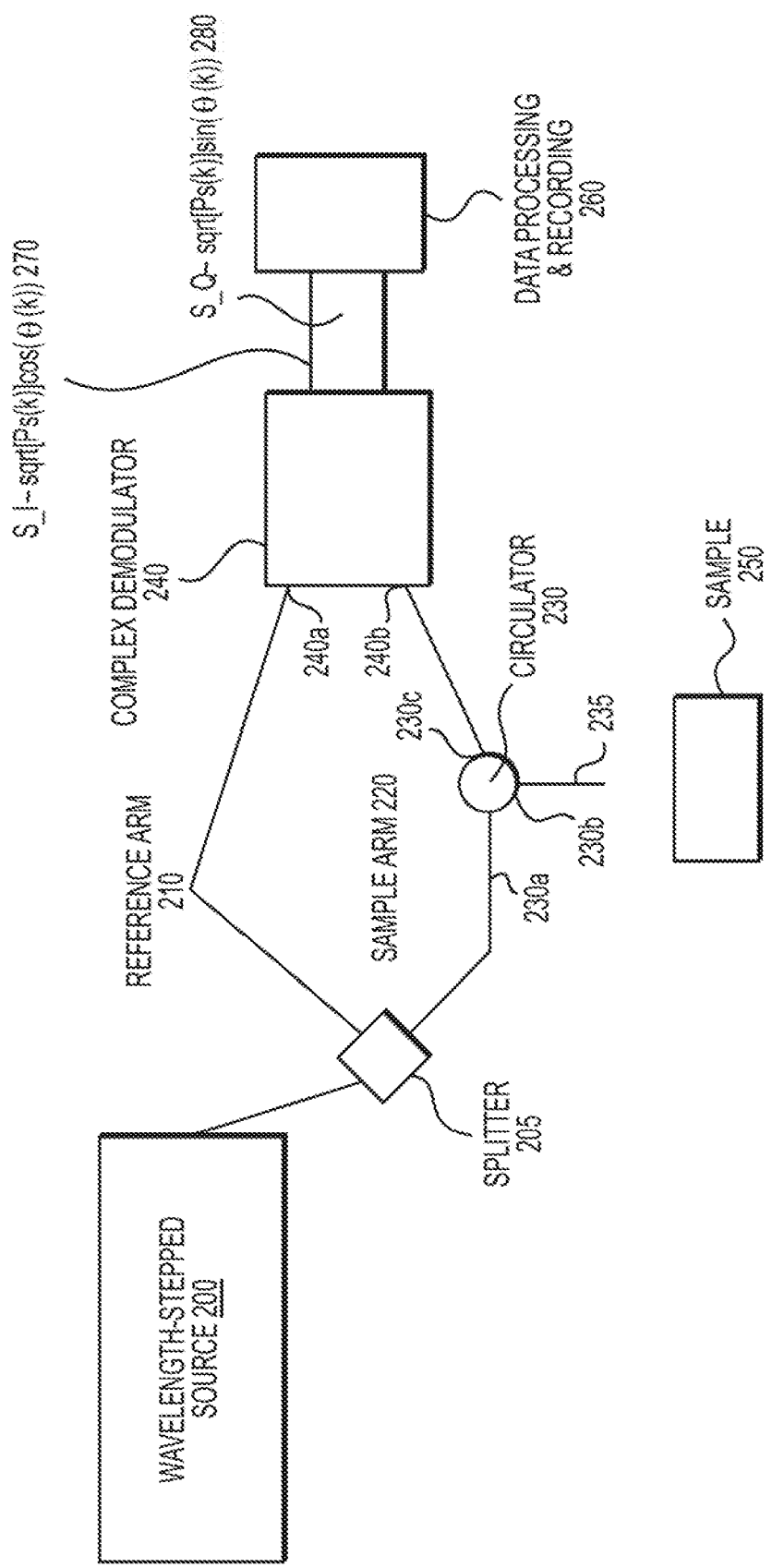
FIG. 2 is a block diagram of an exemplary optically subsampled (OS-OCT) imaging system according to an exemplary embodiment of the present disclosure.

In another exemplary embodiment of an exemplary optically subsampled (OS-OCT) imaging system shown in FIG. 2, the wavelength-stepped source 200 can be divided into a sample arm 220 and a reference arm 210 by an optical splitter 205. The light or other electromagnetic radiation in the reference arm 210 can be directed to a first port 240a of a complex demodulator 240. The light or other electromagnetic radiation in the sample arm 220 can be directed to and collected from a sample. This can be accomplished, for example, by directing the sample arm light to a first port 230a of an optical circulator which can direct this light or other electromagnetic radiation preferentially to port 230b. Light or other electromagnetic radiation from port 230b can be directed by an optical fiber 235 toward a sample 250. Optical fiber 235 can include but not limited to various probes, catheters, endoscopes, and microscopes, which are known in the art for controlling the location and other characteristics of the sample arm light on the sample. Backscattered light or other electromagnetic radiation from the sample 250 can be collected by the fiber 235, and returned to port 230b of the circulator 230 and preferentially directed to port 230c. This light or other electromagnetic radiation can then be directed to port 240b of the complex demodulator 240. The complex demodulator 240 can include, e.g., optical components, digitizers, and digital processing. The complex demodulator can be used to measure, for each wavenumber channel, signals that are associated with the interference between the sample arm 220 and the reference arm 210. For example, the complex demodulator can provide, corresponding to each wavenumber channel, a complex signal S (consisting of a combination of 270 and 280), which is proportional to complex reflected sample field, $$S_i \propto \sqrt{P(k_i)} e^{(\sqrt{-1})\theta(k_i)} \qquad \text{Eq. 1}$$

where $P(k_i)$ is the reflected signal power corresponding to wavenumber $k_i$ and $\theta(k_i)$ is the phase difference between the reference arm light and reflected sample light corresponding to wavenumber $k_i$. The complex signal S (including, e.g., a combination of 270 and 280) can be forwarded to a data processing and recording unit 260 (which can include one or more computers or one or more processors).

In an exemplary embodiment of the present disclosure, the complex demodulator 240 can be based on polarization-based demodulation apparatus, e.g., as described in Vakoc, Optics Letters 31(3) 362-364 (2006) U.S. Patent Publication No. 2007/0035743. In another exemplary embodiment of the present disclosure, a phase modulator can be placed in either the reference arm 210 or the sample arm 220. The exemplary phase modulator can be provided, configured and/or structured to induce, e.g., a phase shift of π/2 radians or 0 radians, such that two measurements can be made at each of these phase shifts for each wavenumber channel, providing time-multiplexed in-phase and quadrature signals necessary to construct the complex signal S. In another exemplary embodiment of the present disclosure, the complex demodulator can be based on the use of a 3×3 couple, as described in, e.g., Choma, Optics Letters 28(22) 2162-2164.

Figure 3:
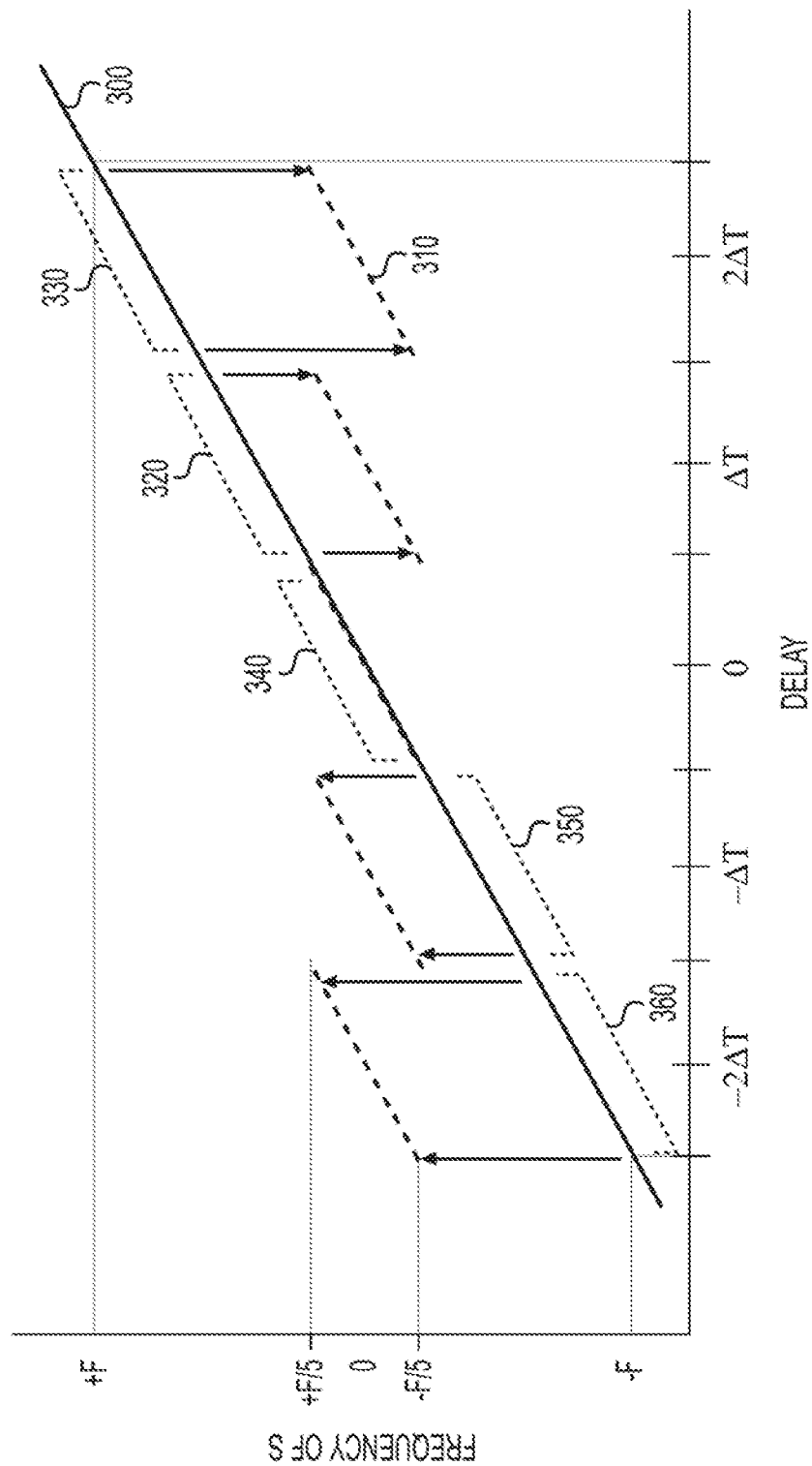
FIG. 3 is a graph illustrating an aliasing of depth signals in the exemplary OS-OCT system according to an exemplary embodiment of the present disclosure.

FIG. 3 depicts a graph illustrating an aliasing of depth signals in the exemplary OS-OCT system according to an exemplary embodiment of the present disclosure. As shown in FIG. 3, the frequency conversion can occur by subsampling the interference at the discrete wavenumbers $k_i$. The exemplary graph of FIG. 3 provides the frequency of the complex signal S as a function of delay between the sample arm and reference arm. The solid curve 300 shows the exemplary frequency for a continuously swept wavelength source, while dashed curve 310 shows the measured frequency using optical subsampling at wavenumbers $k_i$. In the frequency range centered at zero delay 340, no conversion is likely induced. At frequency ranges corresponding to larger magnitudes of delay, frequencies can be down-converted to a baseband signal. For example, the frequencies in the delay range 320, which appear between +F/5 and +3*F/5 when using a wavelength-swept source can be downsampled to the range −F/5 to F/5 using optical subsampling. By detecting only, e.g., the limited frequency range from −F/5 to F/5, signals over the full depth characterized by −2.50T to +2.5 OT can be acquired with reduced data volume.

Figure 4:
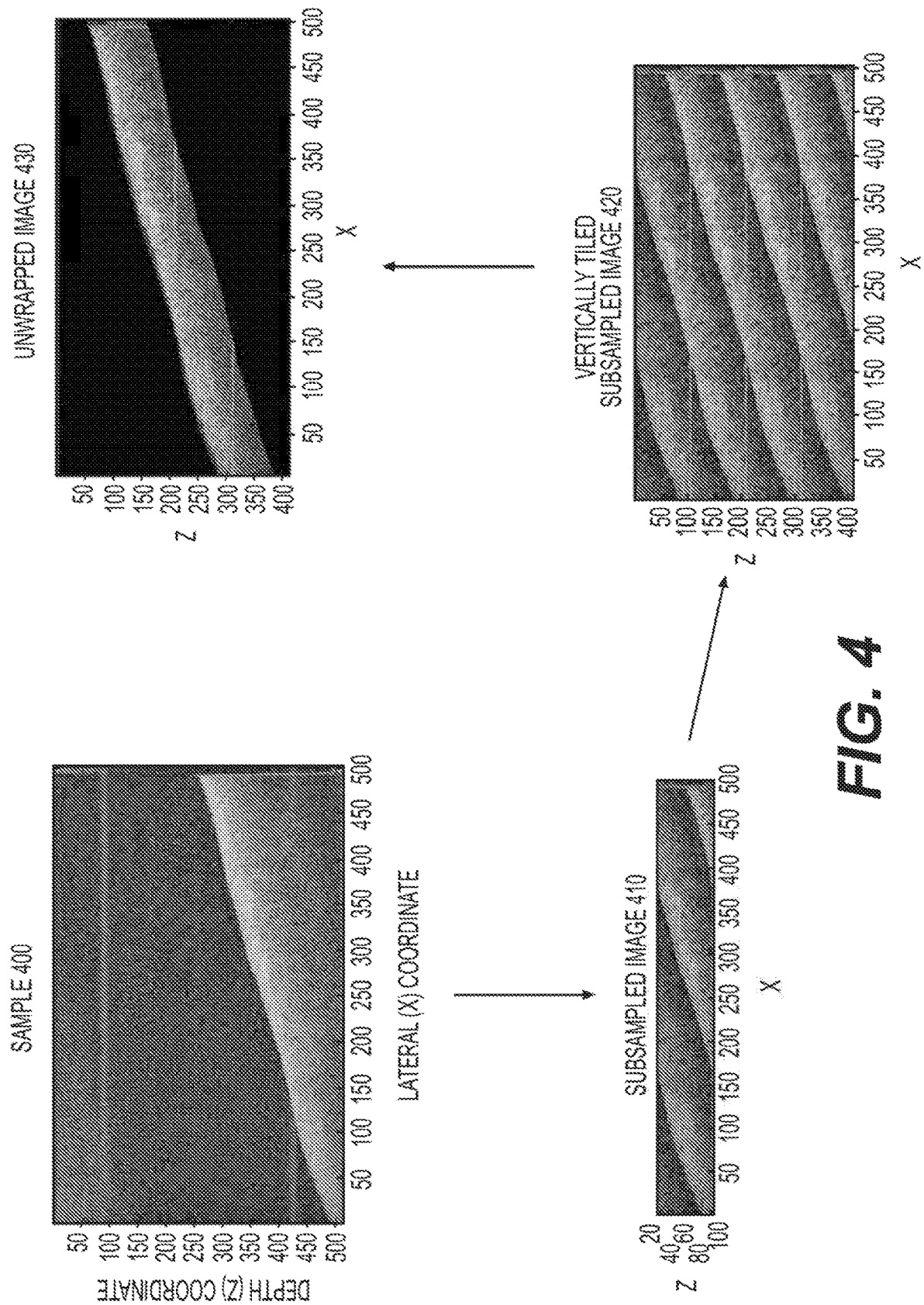
FIG. 4 is a set of exemplary illustrations of circular wrapping of imaging in the exemplary OS-OCT system according to an exemplary embodiment of the present disclosure.

In the exemplary embodiment described above, the data processing and data storage unit 260 (see FIG. 2) can generate a scattering profile in depth from each of the acquired complex signal arrays Si according to approaches utilizing discrete Fourier transforms, which are known in the art. These exemplary profiles can be concatenated to generate images. FIG. 4 illustrates a set of exemplary illustrations of circular wrapping of imaging in the exemplary OS-OCT system according to an exemplary embodiment of the present disclosure. As shown in FIG. 4, the subsampled image resulting from a sample that spans an extent greater the depth range of the subsampled image are generated. An exemplary sample can be utilized that is arranged at an angle as depicted in an exemplary image 400, which can be acquired with an exemplary OFDI system providing a complex demodulation and, e.g., without subsampling. By, e.g., discarding some of the sampled data-points within each A-line, a subsampled image can be generated and is shown in an exemplary image 410. The image depth range can be significantly reduced, and that signals occurring outside the baseband can be downconverted to appear within this reduced depth range. By tiling this image, i.e., concatenating copies of the image vertically, one can recognize the original structure 420. Using a surface finding routine, a single representation of the object can be isolated from the duplicate representations 430, recovering the image of the sample. Note that imaging was effectively achieved over a range sufficient to encompass the tilted sample, but with at a reduced data volume corresponding to the depth range depicted in 410.

Figure 5:
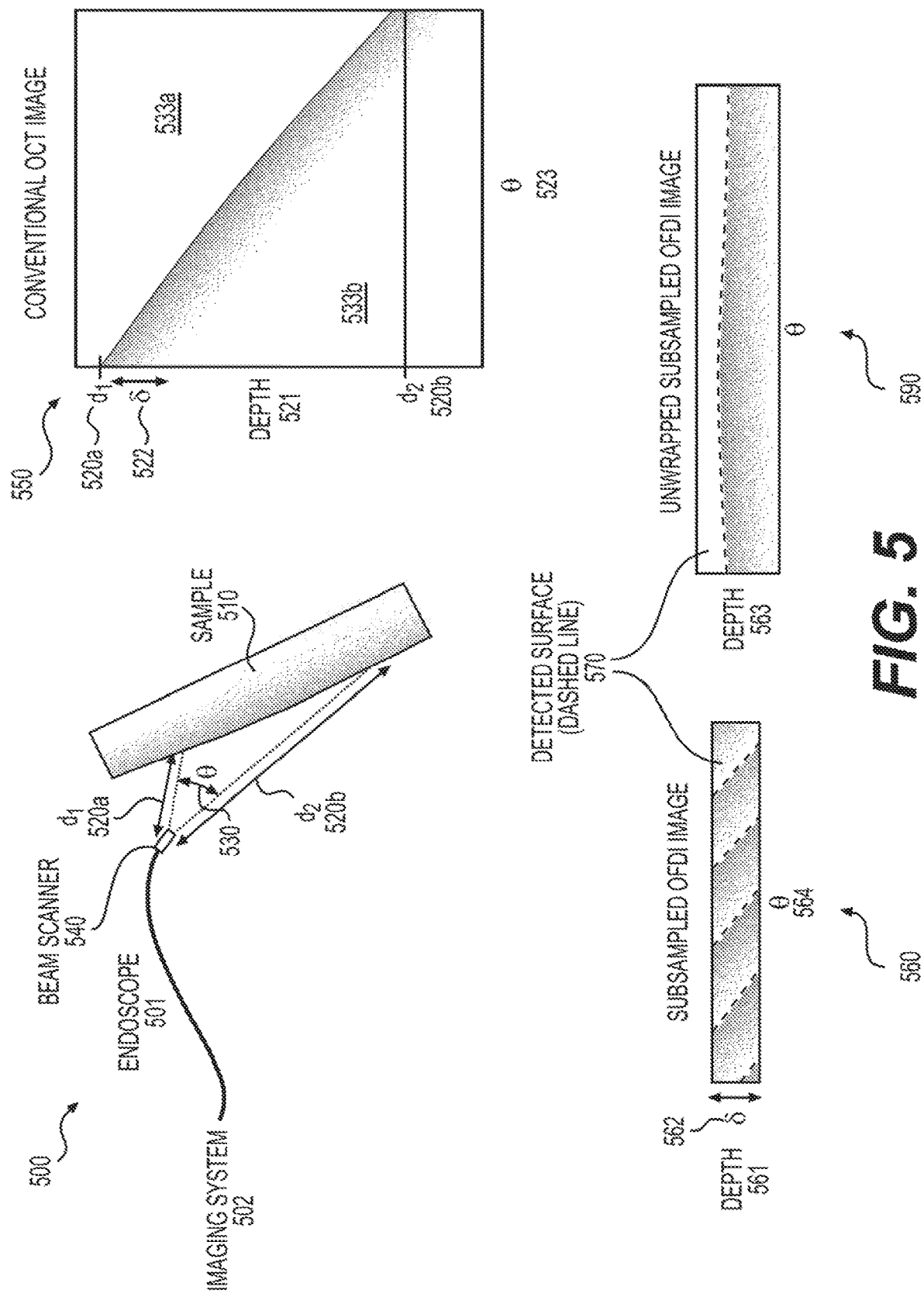
FIG. 5 is a set of illustrations of an imaging probe used in the exemplary OS-OCT system and exemplary images that are obtained for a tilted sample, according to an exemplary embodiment of the present disclosure.

The use of subsampled optical imaging to increase the effective depth range is illustrated in FIG. 5 which shows a set of illustrations of an imaging probe used in the exemplary OS-OCT system and exemplary images that are obtained for a tilted sample, according to an exemplary embodiment of the present disclosure. The imaging instrument 500 can comprise an endoscope 501 that can convey an imaging light or other electro-magnetic radiation from a system 502 to a sample 510, and returns backscattered light or other electro-magnetic radiation to the system 502. The endoscope 501 can be provided by or include using a single bidirectional waveguide such as an optical fiber or alternatively can be provided by using two or more waveguides. One of waveguides can propagate light or other electro-magnetic radiation from the system 502 to the sample 510, and another one of the waveguides can return scattered or reflected light or other electro-magnetic radiation from the sample 510 to the system 502. The endoscope 501 can include, e.g., near its distal tip, a beam scanner 540 that is able to scan the angle 530 of the light exiting the endoscope 501. The beam scanner 540 can be based on a microelectromechanical scanner, as described in Kim, et. al, Opt. Express 15, 18130-18140 (2007). For a sample oriented at an angle to the endoscope, the distance from the beam scanner 540 to the sample surface for one angle can be relatively shorter, for example, d1 520a, while for another angle relatively longer, for example d2 520b.

Using conventional OCT or OFDI techniques, the imaging system 500 can acquire data over the full depth range (d2−d1+δ), where the parameter δ 522 describes the imaging depth into the sample. A conventional OCT or OFDI image 550 provides the image as a function of depth 521 and angle 523. The exemplary image occupies a depth range given by d2−d1+δ. Acquiring data over this large area in a short time requires fast digitization and data transmission capabilities. Such exemplary image can also indicate that the acquisition may be inefficient. This can be because, in that large areas of the acquired image, there is little or no information content either above the tissue surface 533a or a depth greater than δ below the tissue surface 533b. The use of subsampled optical frequency domain imaging or subsampled SD-OCT can facilitate an acquisition of the same information content, and with a greater efficiency. An exemplary subsampled OFDI image 560 is provided as a function of depth 561 and angle 564. The exemplary imaging system 500 can be configured to provide an imaging range of δ 562. This exemplary imaging range does not have to be greater than the imaging penetration depth into the sample, and can alternatively be less if information is desired over a more shallow region. The wrapping properties of an exemplary subsampled imaging procedures can facilitate a capture of information from the superficial depth δ of the sample at all angles. Furthermore, an exemplary imaging acquisition bandwidth is likely not dedicated to the empty space above the tissue surface, or below the imaging penetration into the tissue.

It is possible to locate or otherwise determine the tissue surface 570 using surface finding procedures, including, for example, snake procedures (as described in Yezzi, et. al., IEEE Tran Med Imag 16, 2 199-209 (1997)), and to unwrap the exemplary image to generate an image 590 where the tissue is shown with a surface that is approximately constant in depth.

Exemplary Embodiment of High-Speed OS-OCT Imaging System

Exemplary embodiments of a high-speed optically subsampled imaging system and image display apparatus and methods according to the present disclosure are described herein below, and illustrated in FIGS. 6-16.

Figure 6:
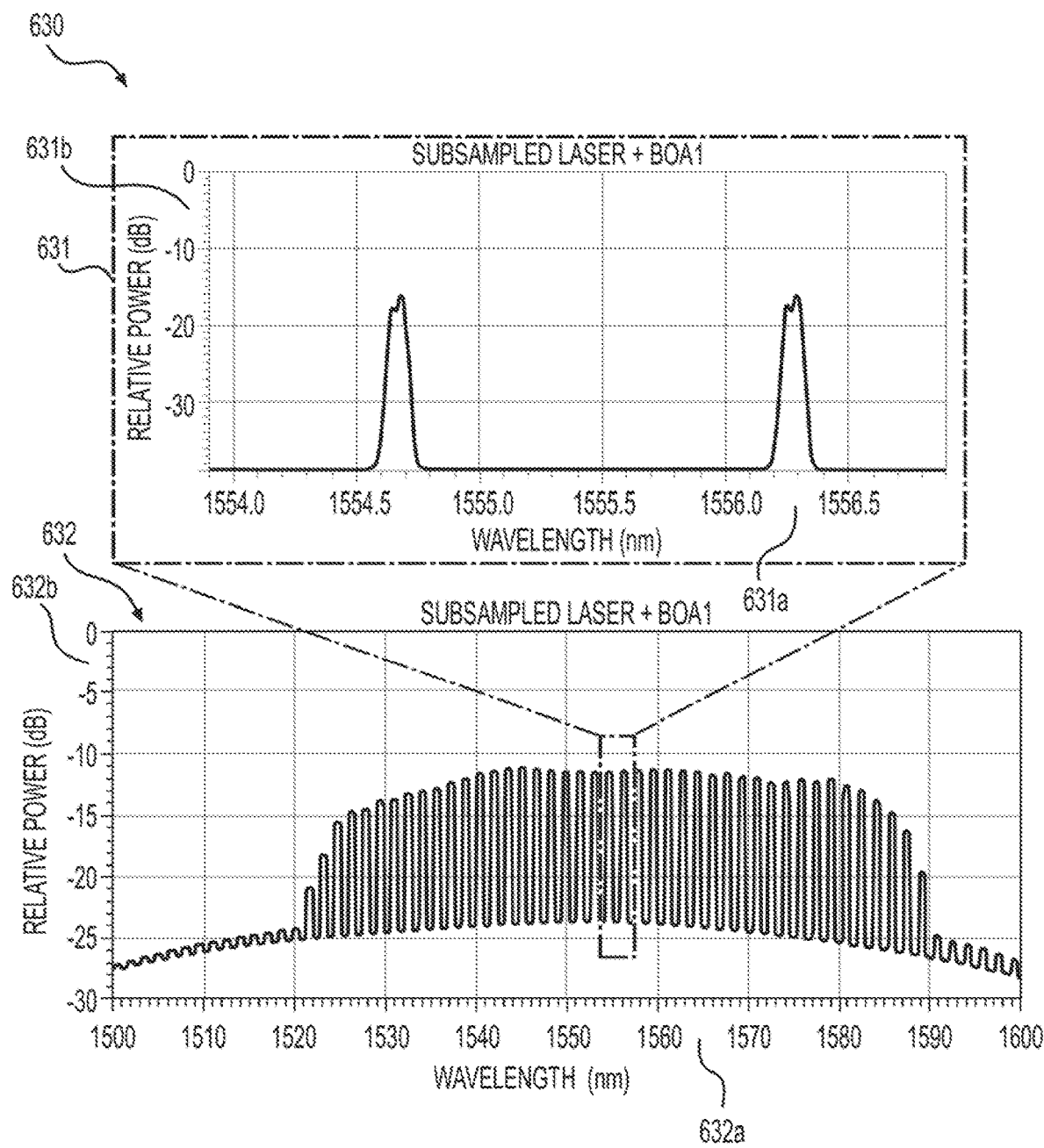
FIG. 6 is a set of illustrations of an exemplary high-speed wavelength stepped source, and graphs of exemplary outs produced thereby according to an exemplary embodiment of the present disclosure.
Figure 6:
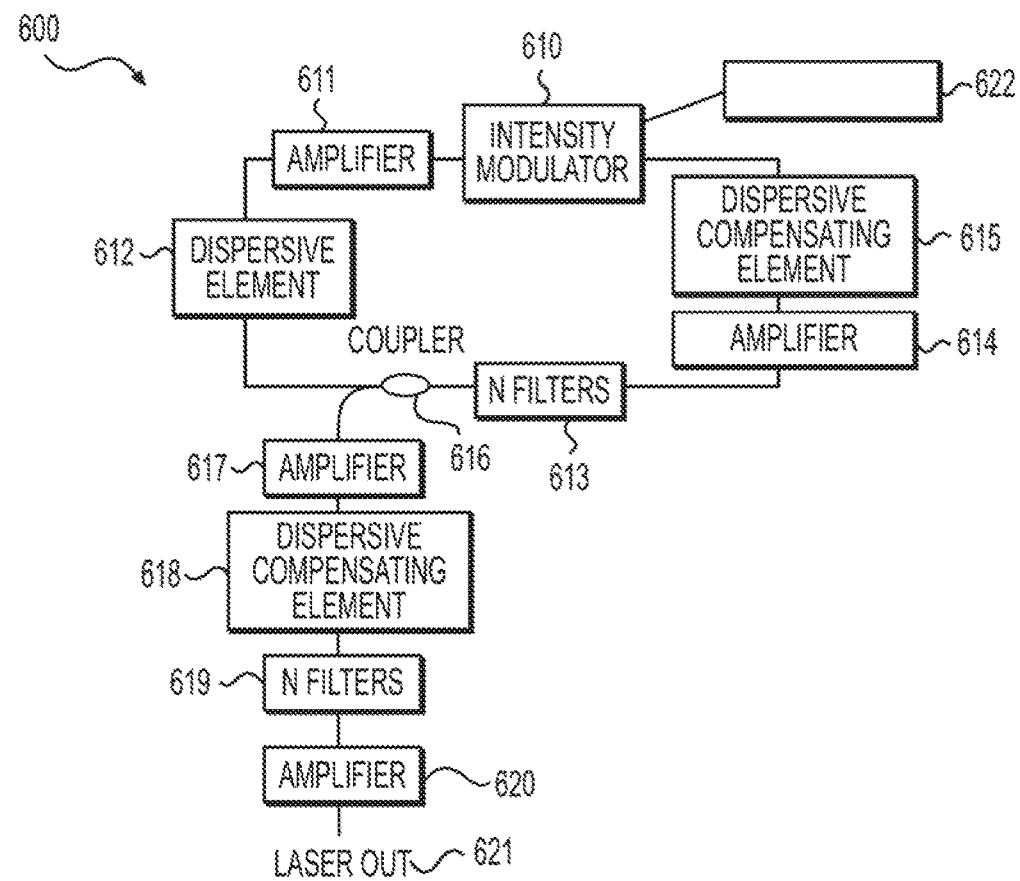
Figure 6:
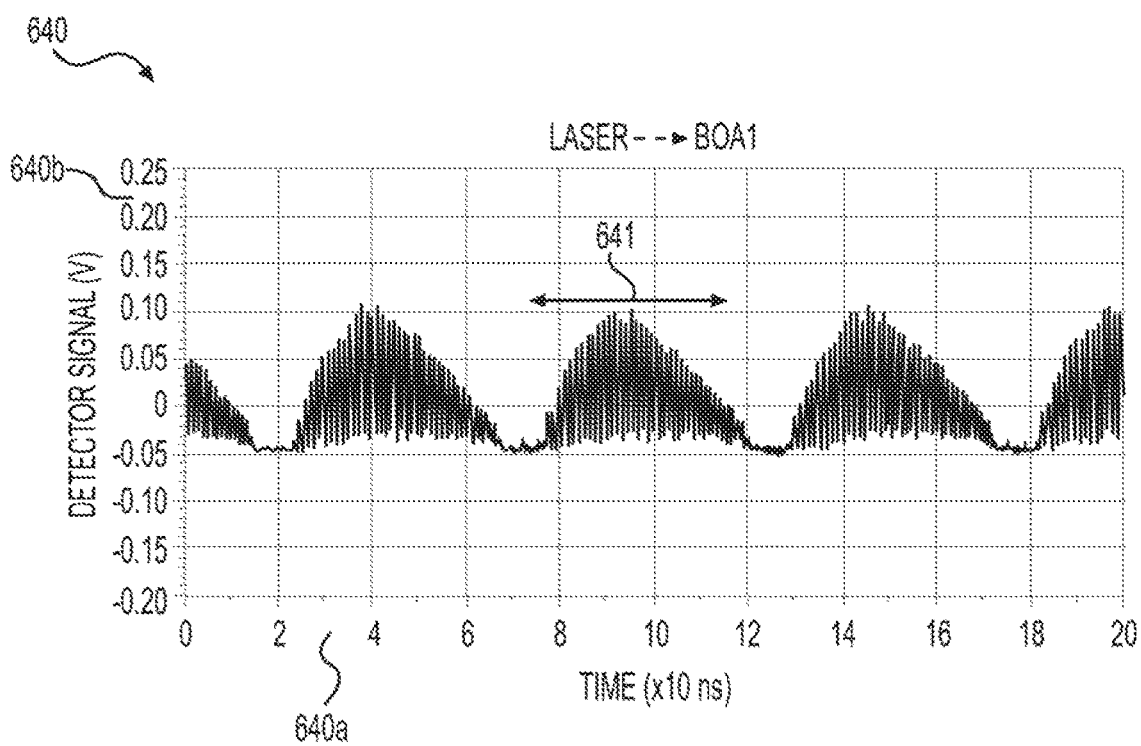

For example, FIG. 6 shows an exemplary embodiment of a high-speed laser source and exemplary outputs provided by one or more components thereof according to the present disclosure. As shown in FIG. 6, the exemplary laser apparatus 600 includes a ring cavity comprising an intensity modulator 610, a set of semiconductor optical amplifiers (611 and 614), a first dispersive fiber 615, a set of wavelength selective filters based on fixed Fabry-Perot etalons 613, an output coupler 616, and a second dispersive fiber 612. A laser light or other electro-magnetic radiation can circulate in the clockwise direction in the laser cavity. A negative dispersion element can be generated or otherwise made from, e.g., a dispersion compensating fiber providing approximately −700 ps/nm total dispersion at 1550 nm. A positive dispersion element can be generated or otherwise made from, e.g., a standard single mode fiber providing +700 ps/nm total dispersion at 1550 nm. Such exemplary standard fiber can be operated in a double-pass configuration with a Faraday rotator mirror to reduce the effect of polarization-mode dispersion. The exemplary laser can operate with a center wavelength o, e.g., approximately 1550 nm and a lasing bandwidth from 1522 nm to 1590 nm 632a. It should be understood that the laser can operate at additional wavelengths and bandwidths.

The light or other electro-magnetic radiation from the dispersion compensating fiber can be amplified by, e.g., a broadband semiconductor optical amplifier (614, 611) that can include optical isolators to prevent light/radiation passage in the counter-clockwise direction. This amplified light is passed through a set of two identical FP etalons with 200

GHz FSR 613. The laser can be operated with one etalon, or a plurality of etalons. The exemplary etalon(s) can transmit light or other electro-magnetic radiation at approximately equally spaced wavenumbers. For example, two FP etalons can be used in one exemplary embodiment to narrow the optical transmission spectrum of the combined filter and to improve noise performance and reduce nonlinear interactions in the amplifiers and fibers. An output coupler 616 can be placed after the filters 613, and directed approximately 20% of the light out of the cavity. The exemplary coupling ratio of the output coupler 616 can be set over a large range. In such exemplary embodiment of the present disclosure, the length of each dispersive element can be selected to substantially match in magnitude, and also have opposite signs across the operating bandwidth.

The intensity modulator 610 can be driven by a pulse generator 622 producing a pulse of a tunable length and a tunable repetition rate. In one exemplary embodiment, the pulse length can be between 0.05 ns and 5 ns, although other ranges of the pulse length are possible. Such exemplary pulse length can provide a temporal window with high optical transmission through the modulator 610. The intensity modulator 610 can also provide a high on-off extension ratio (approximately 30 dB) through optimization of the lithium niobite waveguide properties can be used to limit the transmitted light when in the "off" state. Alternatively or in addition, an electro-optic intensity modulator can be used, or a semiconductor gain element can be current modulated to provide this intensity modulation function. A polarizer can be included prior to the modulator 610 to compensate for a modulator that has polarization-dependent operation, and a polarization controller can be placed between the polarizer and the modulator to align the returned light polarization state to the optimal axis of the modulator. For example, polarization controllers can be included throughout the laser cavity to align light polarization states at each element.

In one exemplary embodiment of the present disclosure, the pulse generator 622 can be driven at, e.g., about 18.9 MHz, which can be the 4336th harmonic of the fundamental cavity frequency given by the inverse of the cavity round trip time. By operating at this exemplary harmonic, the pulses that return to the intensity modulator can be matched to a transmission window and pass through the exemplary modulator. At the modulator, most or all lasing wavelength pulses can be temporary overlapped within a single multi-wavelength pulse. After passing through the dispersive fiber, these pulses can be temporally separated. The second dispersive fiber can then recompress these pulses. Each pulse at the modulator can be stretched to produce a pulse train with each pulse in the pulse train having a separate wavelength. Multiple pulse trains are present in the cavity at any given time.

The laser output can provided from the output coupler 616. This output can be passed through a further optical amplifier to increase power, and/or it can be further filtered by one or several wavelength selective filter, such as, e.g., FP etalons 619 to improve line width and/or reduce ASE light transmission. The output pulse train can be stretched or compressed in time using a dispersion compensating element (or a positive dispersion element) 618 that can be or include, for example, a dispersion compensating fiber or a fiber Bragg grating array operated in reflection mode, or a chirped fiber Bragg grating operated in reflection mode. The external dispersion element 618 can be used to modify the A-line duration and the associated required digitization speed externally without modifying the laser cavity.

Additional amplifiers 617, 620 can be included to increase power and improve line width. These amplifiers can be based on semiconductor optical amplifiers but can constructed for example by doped optical fibers or utilize Raman gain. The use of the filters external to the laser cavity 619 can remove background amplified spontaneous emission light and narrow the line width of each wavelength pulse. The amplification and filtering can be repeated in multiple stages to further increase power and optimize line width.

In one exemplary embodiment of the present disclosure, the laser output can include a pulse train 640 with each pulse having a distinct wavelength corresponding to the transmission pass band of the filters 613, 619. This can be visualized by a high-speed opto-electronic receiver and captured on a high-speed oscilloscope. The length of such exemplary pulse train 641 in the exemplary embodiment according to the present disclosure can be set to approximately 50 ns, although other settings are conceivable within the scope of the present disclosure. Each pulse train denotes an "A-line" in OCT imaging, and can contain distinct pulses each of which can have a unique wavelength that is approximately equally spaced in wavenumber and matches the wavelength selective filter transmission peaks. The optical spectrum of the output laser 630 can be a comb structure with substantially distinct bands of output wavelength 631.

The exemplary spectral output 630 is illustrated in FIG. 6 as a plot of optical power 632b, 631b as a function of wavelength 632a, 631a. A zoomed image of a smaller wavelength range is shown in a graph 631, while a larger range is shown in a graph 632. The temporal output 640 plots the received voltage 640b as a function of time 640a.

The effective A-line rate of the laser can be changed by operating the intensity modulator at different harmonics of the fundamental cavity round trip frequency (or equivalently at different pulse repetition times that are subharmonics of the cavity round trip time). This can facilitate the A-line repetition rate to be changed electronically. The magnitude of the dispersion can be adjusted to modify the A-line length by adjusting the temporal spacing between each wavelength pulse. While these elements are shown in a particular organization and/or order in FIG. 6, it should be clear to those skilled in the art that there are alternative orderings and/or organization that can be used and are within the scope of the present disclosure.

Figure 7:
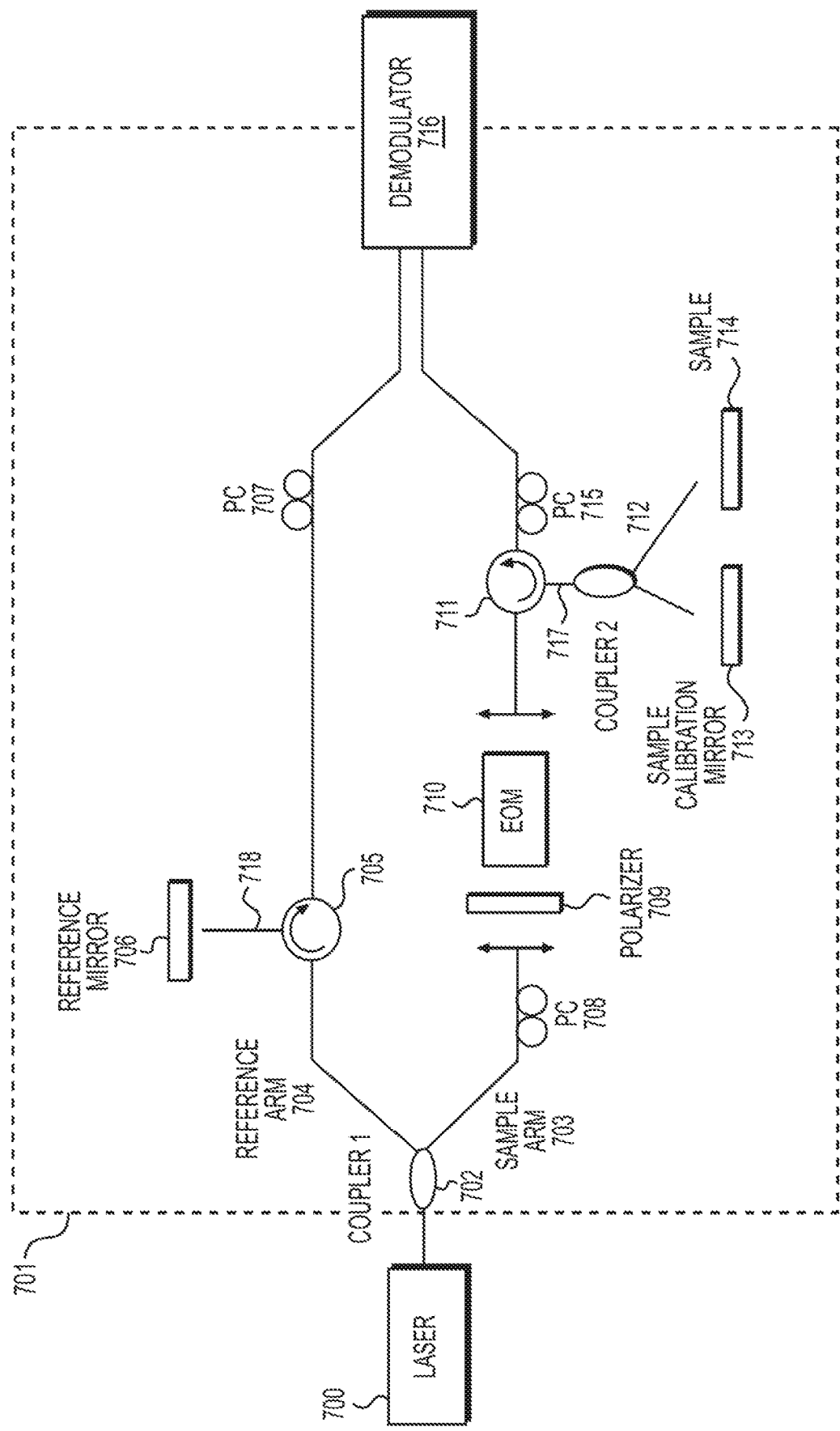
FIG. 7 is a diagram of an exemplary high-speed OS-OCT imaging system according to an exemplary embodiment of the present disclosure.

In an exemplary embodiment of the present disclosure, an output of the high-speed laser source 700 can be directed to the input of an interferometer 701 (as shown in a block diagram of FIG. 7). This interferometer 701 can split or separate an output of the laser source 700 into a sample arm 703 and a reference arm 704. The sample arm 703 can include an electro-optic modulator (EOM) 710 for polarization-modulation that can be used to improve polarization-sensitive imaging. The EOM 710 can be configured to modulate the polarization state of each wavelength pulse, of each A-line, of each imaging frame, of each imaging volume, or of an arbitrary time-block of data. The EOM 710 can be placed in the sample arm 703 before and in an optical path of an optical circulator 711 that can direct light or other electro-magnetic radiation to a double-pass fiber 717 that provide light or other electro-magnetic radiation to the sample 714. Alternatively or in addition, the modulator (e.g., the EOM 710) can be placed before and in an optical path of the coupler 702 to modulate both sample and reference arm lights or other electro-magnetic radiations. Alternatively or in addition, such exemplary modulator can be located in the double-pass fiber 717. This double pass fiber can contain a splitter 712 that directs a fraction of the light to a structure such as a mirror 713 to be used for calibrating the system. The sample arm 703 can also provide light or other electro-magnetic radiation to the sample 714. The reference arm light can be passed through a circulator 705 to a double-pass fiber 718 leading a mirror 706. The position of this mirror 76 can be adjusted to modify the reference arm optical delay. Polarization controllers 707, 708, 715 can be provided within the reference and/or sample arms 703, 704. A polarizer 709 can be provided before and in an optical path of the EOM 710 to set the input polarization state into the modulator. The light or other electro-magnetic radiation provided from the reference and sample arms 703, 704 can be combined at an optical demodulator 716.

Figure 8:
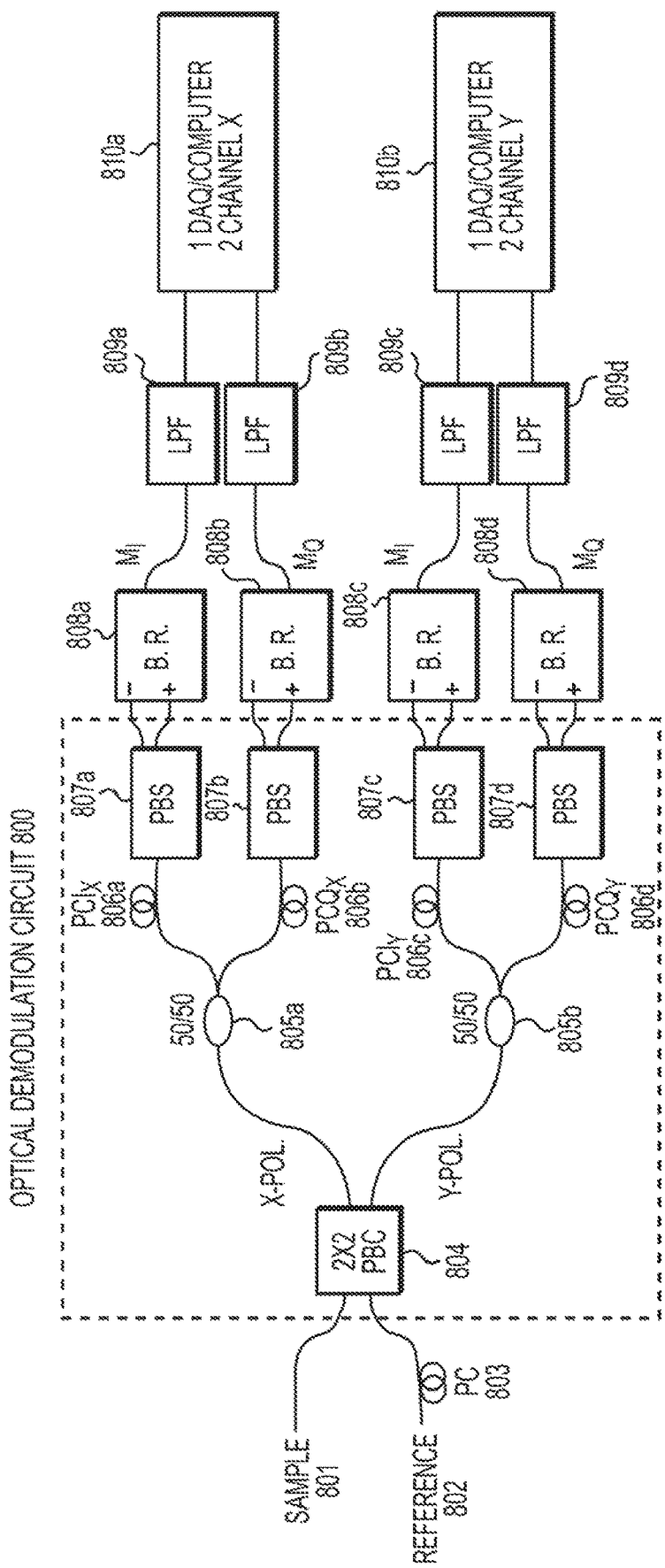
FIG. 8 is a diagram of an exemplary quadrature demodulation system according to an exemplary embodiment of the present disclosure.

FIG. 8 shows a diagram of the optical demodulator 716 of FIG. 7 according to an exemplary embodiment of the present disclosure in greater detail. For example, light(s) or other electro-magnetic radiation from a sample 801 and a reference 802 are provided to a polarization beam combiner (PBC) 804, which splits or otherwise separates the received lights or other electro-magnetic radiation into two orthogonal polarization states. The polarization state of the light or other electro-magnetic radiation from the reference arm 802 can be controlled with a polarization controller 803 which can be configured to split reference arm light, e.g., approximately equally to each of the output ports of the PBC 804 for polarization diverse detection, or primarily in one output port if polarization diverse detection is not used. In each output port of the PBC 804, a system of optical components can be configured to generate a shift in one in-phase channel ($M_I$) detected on a signal 809a for example relative to the other quadrature channel ($M_Q$) detected on a signal 809b. In this exemplary embodiment, polarization controllers 806a, 806b, 806c, 806d can provide different phase delays in the light or other electro-magnetic radiation from the sample arm 801 relative the light or other electro-magnetic radiation from the reference arm 802, and thus induce a controllable phase shift in the interference fringe that is generated by the polarizing beam splitters 807a, 807b, 807c, 807d.

Alternatively or in addition, such exemplary optical circuit can be constructed in free-space using bulk optic splitters and polarization rotators. The outputs of each polarization beam splitters can be passed to opposite signed inputs of balanced receiver 808a, 808b, 808c, 808d for an intensity noise reduction. The signal can be low-pass filtered using filters 809a, 809b, 809c, 809d. The cut-off frequency of these low-pass filters can be set to match the frequency bandwidth of baseband window resulting for optical sub-sampling of the laser which can be approximated as 1/(2*dT) where dT is the temporal spacing of the wavelength pulses from the laser, and/or can be approximated as the minimum temporal spacing of the wavelength pulses from the laser if the temporal spacing is not equal across the A-line. For example, 50/50 optical couplers 805a, 805b can be included in the exemplary system.

When the $M_I$ and $M_Q$ signals are added in quadrature, there can be a reduction in the complex conjugate artifact resulting from conjugate ambiguity in one signal measurement. The amount of reduction, e.g., is the conjugate artifacts correlates with how closely the relationship between $M_I$ and $M_Q$ are to being in perfect quadrature (e.g., about 90 degree phase separation). In order to reduce the number of RF channels, demodulators can be provided that create the information needed to generate $M_I$ and $M_Q$ through sequential phase modulation in the reference or sample arm of the interferometer using for example a lithium niobate phase modulator or an acousto-optic modulator.

Imperfections in the quadrature relationship between the detected interference fringes $M_I$ (e.g., detected on signal 809a) and $M_Q$ (e.g., detected on signal 809b) can result in an imperfect separation of signals from positive and negative delay spaces. In this exemplary embodiment, the measured signals can be modified after acquisition by a digitizer 810a, 810b and transfer of the digitized signals to a computing arrangement (e.g., a computer, a processor and/or a multiple or combination thereof). These exemplary modifications can be used to correct for these errors using known techniques, as described, e.g., in Siddiqui, et. al., Optics Express 23, 5 5508-5520 (2015). Such exemplary corrections can be performed using pre-determined data acquired from a separate sample such as a set of mirror (see the mirror 713 in FIG. 7) signals, and/or can optionally be derived by signals in the sample itself. This correction can remove errors that occur both as a function of measured wavelength (i.e., spectral errors), and errors that occur as a function of RF frequency (i.e., RF errors). RF errors can become significant at high-speed imaging due to the higher RF frequencies involved in the systems. Such exemplary procedure can utilize signals from the sample calibration mirror 713 of FIG. 7 at various depth locations and minimizes residual peaks for all depth locations simultaneously. The exemplary procedure can be used to apply a frequency response function (H(Δ)) in the RF frequency domain to correct frequency-dependent errors. An amplitude and phase error correction can be applied in the RF time domain. These errors can be computed or otherwise determined (e.g., by the computing arrangement) once per system, and applied to all subsequent images provided that the system (e.g., by the computing arrangement) does not significantly change its state. The spectral errors can be computed and applied separately from RF errors (e.g., by the computing arrangement) so that state changes that spectral errors that only affect can be calibrated independently of RF errors.

Figure 9:
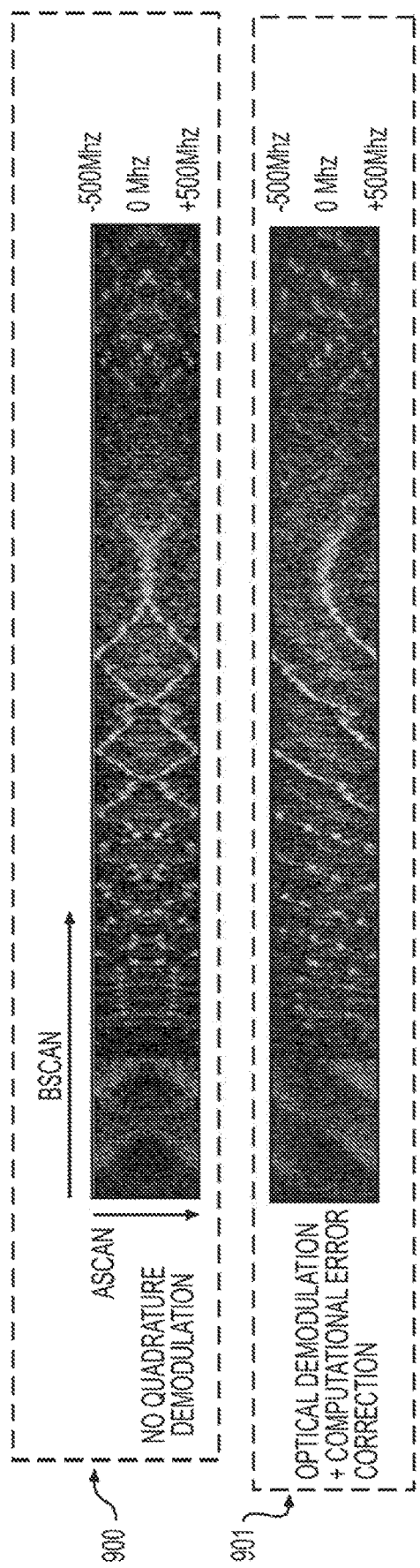
FIG. 9 is a set of exemplary OS-OCT images obtained without and with quadrature demodulation according to an exemplary embodiment of the present disclosure.

An exemplary demodulation circuit can operate on sub-sampled measurements similar to conventional Fourier-Domain measurements, as described in Siddiqui, et. al., Optics Express 23, 5 5508-5520 (2015). In one example shown in FIG. 9, which illustrates a set of exemplary OS-OCT images obtained without and with quadrature demodulation according to an exemplary embodiment of the present disclosure. As shown in FIG. 9, a subsampled image of a finger is provided without quadrature demodulation 900 and illustrates an overlapping of the image and its complex conjugate, causing artifacts in the image. This problem can be solved with demodulation and error correction illustrated in a display 901, as described herein. For example, the exemplary configuration shown in FIG. 8 can be used to generate two phase-shifted interference fringes (e.g., I on the first channel—channel 1) of the digitizer 810a, and Q on the second channel—channel 2) of the digitizer 810a for the X polarization state, and that by using a 1×N splitter instead of the 1×2 splitter 805a, additional phase shifted interference signals can be generated. For example, in one exemplary configuration, a polarization-based demodulation system can provide three phase-shifted interference signals at relative phase shifts of 0 deg, +60 deg, and +120 deg. The exemplary use of three or more phase shifted interference channels can be utilized, for example, to improve quadrature demodulation accuracy, or two reduce the presence of signal artifacts at DC.

Figure 10:
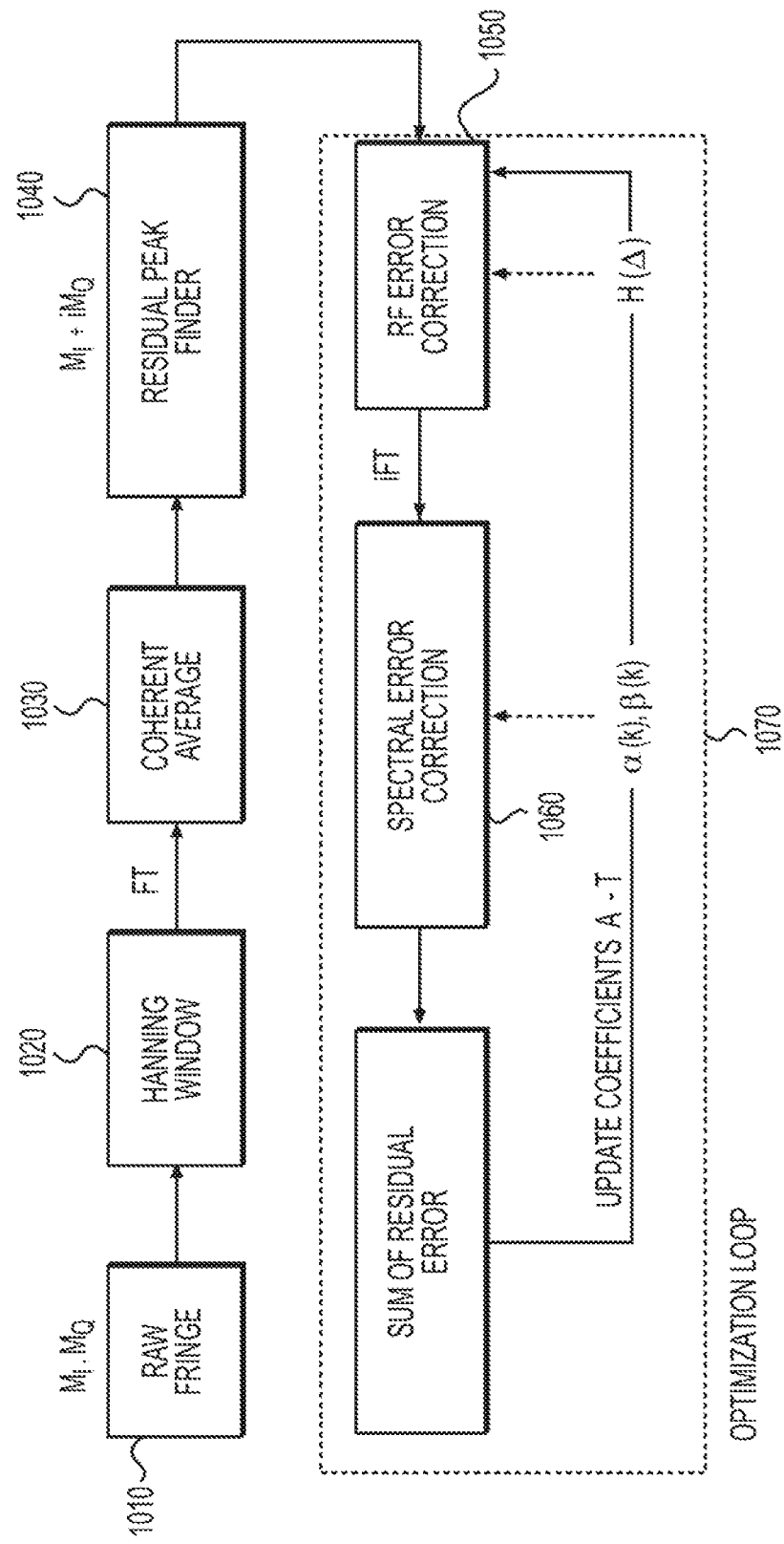
FIG. 10 is a flow diagram of a method providing an exemplary quadrature demodulation and OS-OCT signal processing including techniques to correct for quadrature errors in the optical demodulator according to an exemplary embodiment of the present disclosure.

An exemplary procedure used for processing acquired signals from a mirror structure to derive the post-processing correction factors is described below and shown in FIG. 10, which illustrates a flow diagram of a method providing an exemplary quadrature demodulation and OS-OCT signal processing including techniques to correct for quadrature errors in the optical demodulator according to an exemplary embodiment of the present disclosure. For example, as indicated in FIG. 10, in procedure 1010, the detected signals $M_I$ and $M_Q$ can be obtained, and in procedure 1020 processed with a Hanning window, Fourier transformed (FT), then in procedure 1030 coherently averaged across fringes to improve signal-to-noise ratio (e.g., using a computing arrangement). Next, the signal peak in the Fourier domain can be found in procedure 1040. Thereafter, in procedure 1050, RF error correction can be performed as described in Siddiqui, et. al., Optics Express 23, 5 5508-5520 (2015), followed by spectral error correction in procedure 1060, again as described in Siddiqui, et. al., Optics Express 23, 5 5508-5520 (2015). An error function can be used to update and optimize the correction factors $H(\Delta)$ and $\alpha(k)$ and $\beta(k)$ in procedure 1070 after several iterations through the optimization loop (black dotted box).

Figure 11:
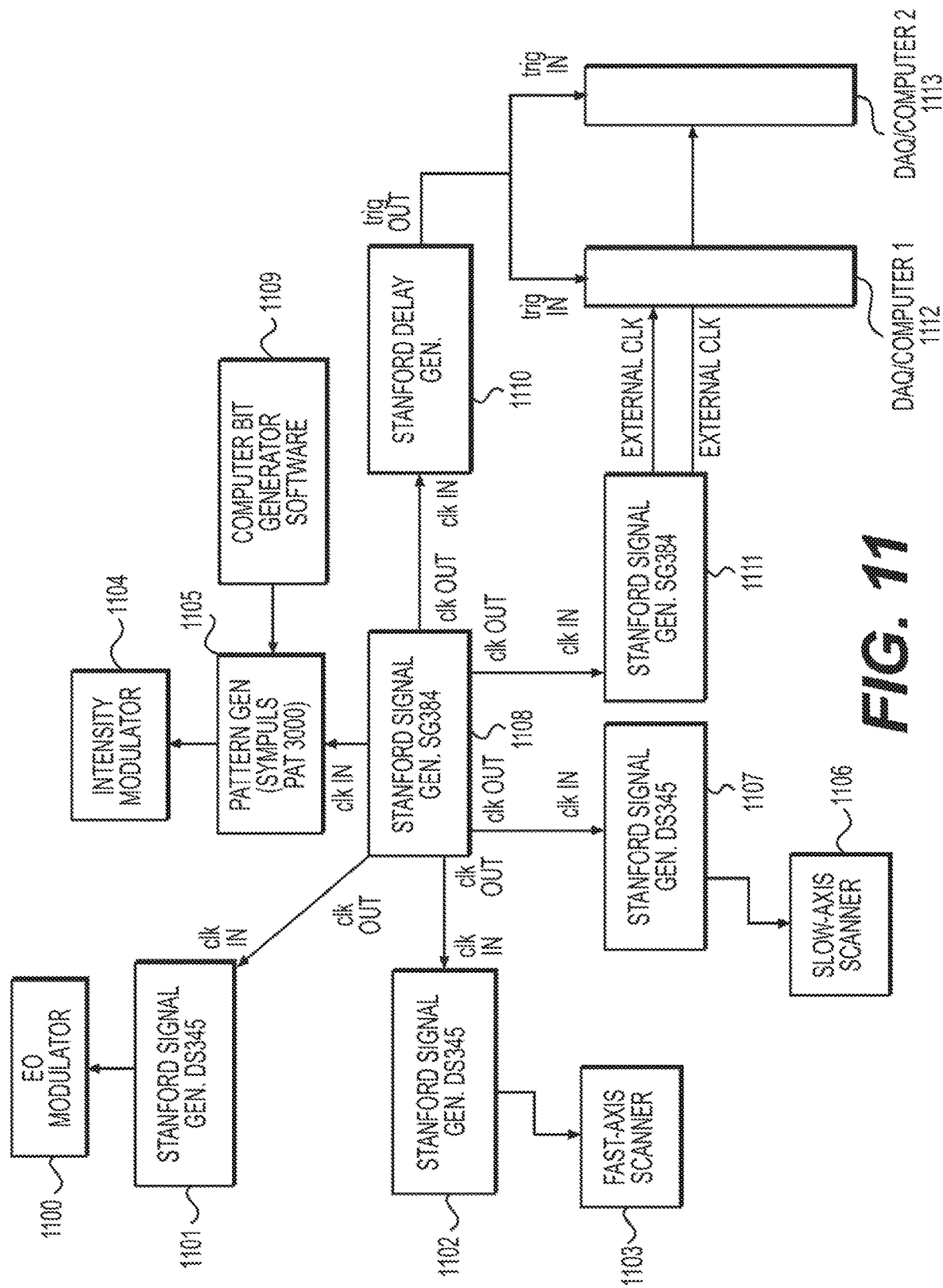
FIG. 11 is a block diagram a system providing an exemplary timing scheme for control electronics in an exemplary OS-OCT imaging system according to an exemplary embodiment of the present disclosure.

An exemplary embodiment of the high-speed optically subsampled OCT system can utilize phase-synchronized clocking systems across many system modules as illustrated in FIG. 11, which shows a block diagram a system providing an exemplary timing scheme for control electronics in an exemplary OS-OCT imaging system according to an exemplary embodiment of the present disclosure. As provided in FIG. 11, a signal generator 1108 can be used as a clock for a pattern/pulse generator 1105 to drive an intensity modulator 1104. The internal clock of this signal generator 1108 can be shared across several electronic subsystems to synchronize and phase-lock the exemplary system, including a first signal generator 1101 controlling an EOM 1100, a second signal generator 1102 controlling a fast-axis beam scanner 1103, a third signal generator 1107 controlling a slow-axis beam scanner 1106, and a fourth signal generator 1111 controlling the acquisition clocks of the high-speed digitizers 1112, 1113 for acquiring interferometer fringe data. The pattern/pulse generator 1105 can utilize a binary data pattern that can be set by a computer arrangement 1109. A trigger output signal from the signal generator 1108 can be passed to a delay generator 1110 to generate trigger signals for the high-speed digitizers 1112, 1113. It should be understood that the above exemplary embodiment is merely exemplary, and that multiple organizations of clocking electronics and signal paths can be understood by one skilled in the art to achieve a similar effect within the scope of the present disclosure. This exemplary timing configuration has been configured to facilitate highly phase stable measurements across A-lines with short or long time separations.

The clock frequency for the exemplary digitizers 1112, 1113 can be configured to be an integer multiple of the laser A-line rate that resulted an integer number of digitized samples for each A-line. This can facilitate multiple A-lines to be averaged directly, i.e., in the measured fringe domain or after FFT as a complex A-line, without needing to account for A-line phase shifts. For example, in this exemplary system, the pattern/pulse generator 1105 can be driven by, e.g., a 3.64437734 GHz signal by the signal generator 1108; the pattern generator 1105 was set by the computer 1109 to produce 192 bits at this frequency and remain "on" for one bit out of this 192 bit sequence, yielding an Aline rate of 3.64437734 GHz/192=18.9811319791667 MHz. The digitizer clock was set to, e.g., 1.23377357865 GHz by an external clock 1111 to provide, e.g., exactly 65 measurements per A-line. For example, a set of continuous acquisitions can be combined to generate a coherently averaged A-line with an improved SNR and an addition of fringe signals. This exemplary coherent averaging of A-lines can be performed using a processor that is on the digitizer board such as a field programmable gate array (FPGA) or using the computer arrangement.

Figure 12:
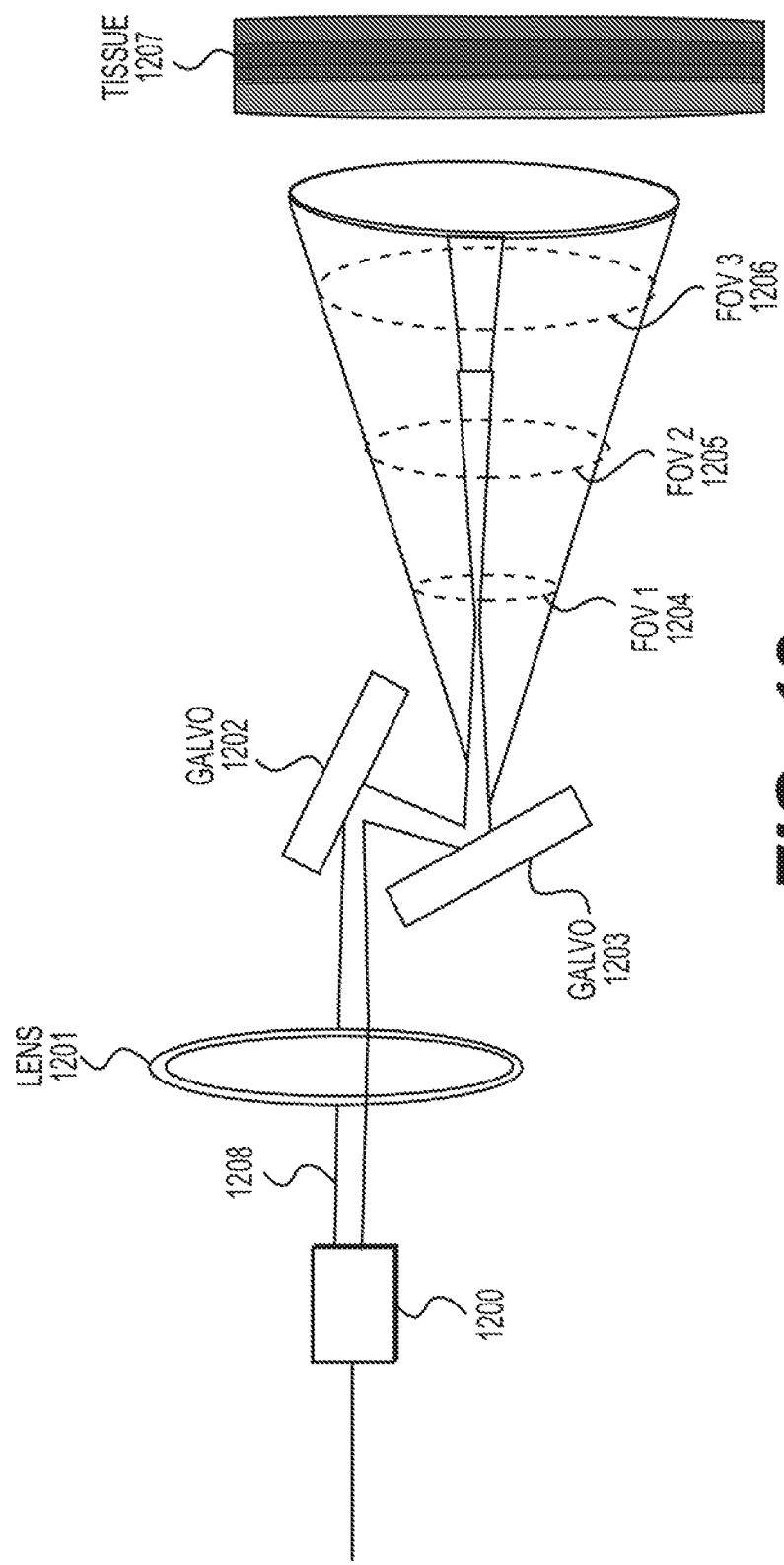
FIG. 12 is a diagram of an imaging microscope used in the exemplary OS-OCT system according to an exemplary embodiment of the present disclosure.

FIG. 12 shows a diagram of an imaging microscope used in the exemplary OS-OCT system according to an exemplary embodiment of the present disclosure. In this exemplary embodiment of the imaging system of FIG. 12 can include a scanned beam probe that incorporates large-angle galvanometric mirrors 1202, 1203 that can scan the beam across the x and y dimensions, respectively. A collimator 1200 can create a collimated beam 1208 that can be directed to the beam scanners 1202, 1203 (e.g., approximate beam size of 7 mm) and a focusing lens 1201 with, e.g., a 250 mm focal length that can be placed before and in an optical path of the scanners 1202, 1203 to create a fan-beam imaging geometry. The exemplary system can facilitate a wide-field depth-resolved images of a sample, for example, of the human face at fields of view 1204,1205,1206 that expanded as a sample 1207 was moved away from the exemplary probe.

Figure 13:
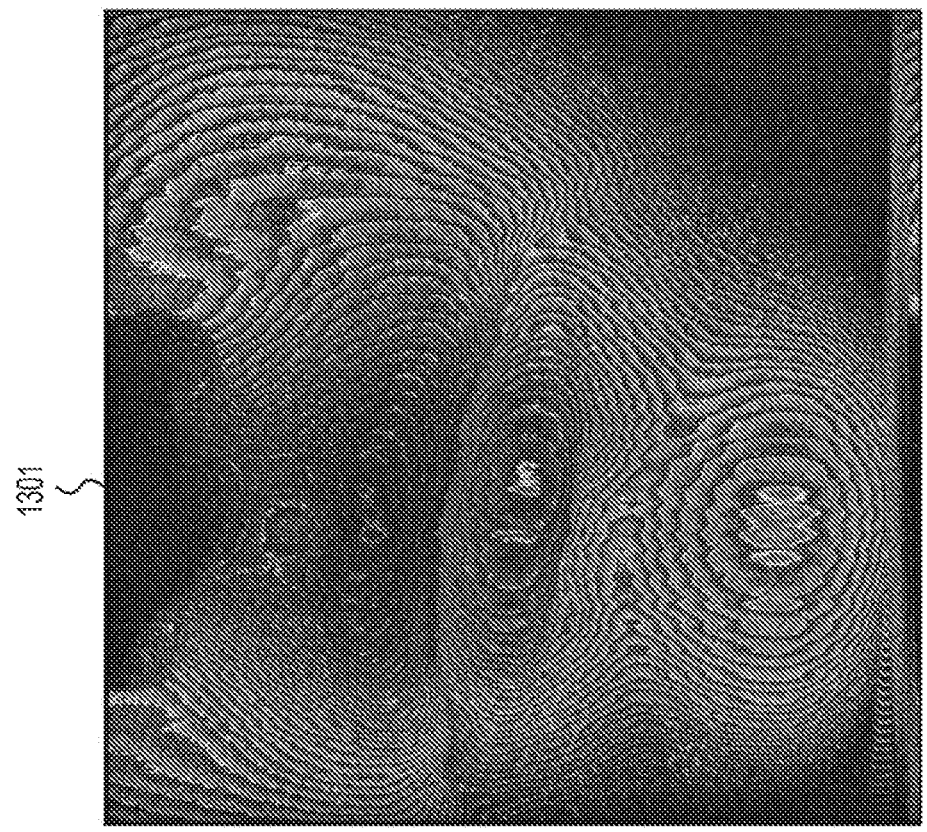
FIG. 13 is an exemplary set of wide-field OS-OCT images according to an exemplary embodiment of the present disclosure.
Figure 13:
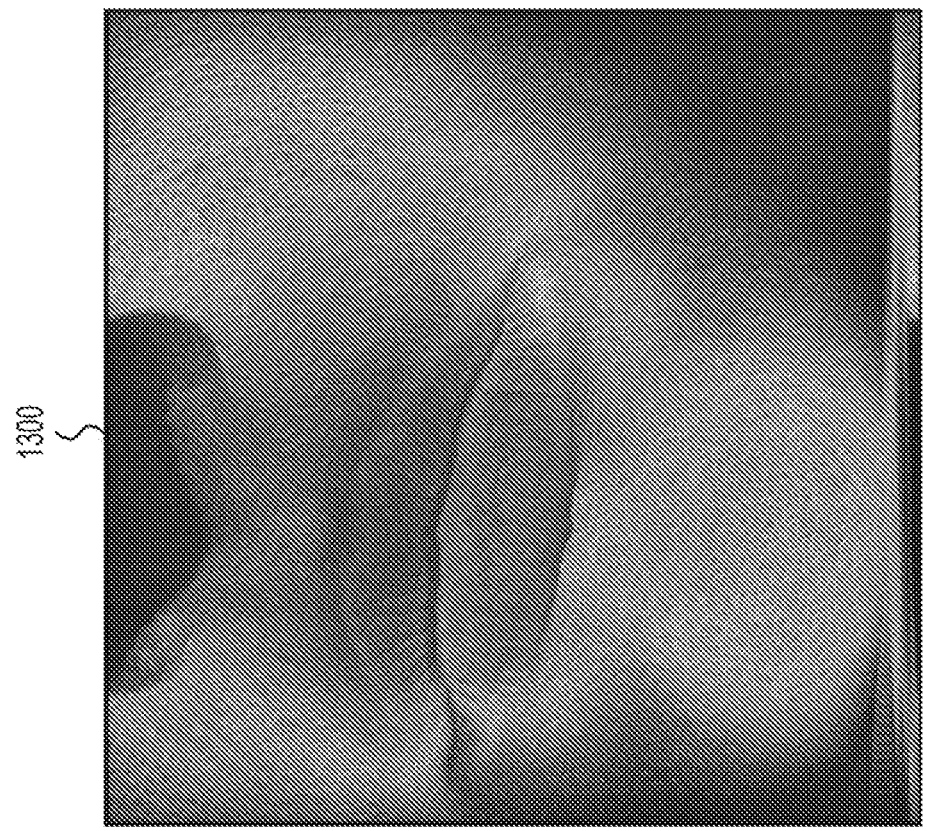

FIG. 13 illustrates an exemplary set of wide-field OS-OCT images according to an exemplary embodiment of the present disclosure. For example, the three-dimensional dataset can be visualized by examining a single depth plane of an exemplary image 1301, an average intensity projection across depth of an exemplary image 1300, or a single cross-sectional image, among other display modes. The exemplary images 1300 and 1301 demonstrate the large depth-field and wide-field capabilities of the exemplary system. In these exemplary images 1300, 1301, a depth of field of more than 3 centimeters can be obtained. In acquiring this image, the exemplary laser was operated at an approximate 18.9 MHz Aline rate, the image displays 2000× 2000 transverse pixels (spanning a 9 cm×9 cm region), measured with a fast-axis scanner operating at 16.5925 Hz and a slow-axis scanner operating at 0.008296 Hz, and using a 250 mm focusing lens. Because of the speed of such exemplary laser far exceeded the scanning speed, it was possible to average adjacent A-lines in a single frame, between two frames, or between volumes in order to improve the SNR of the exemplary image.

Figure 14:
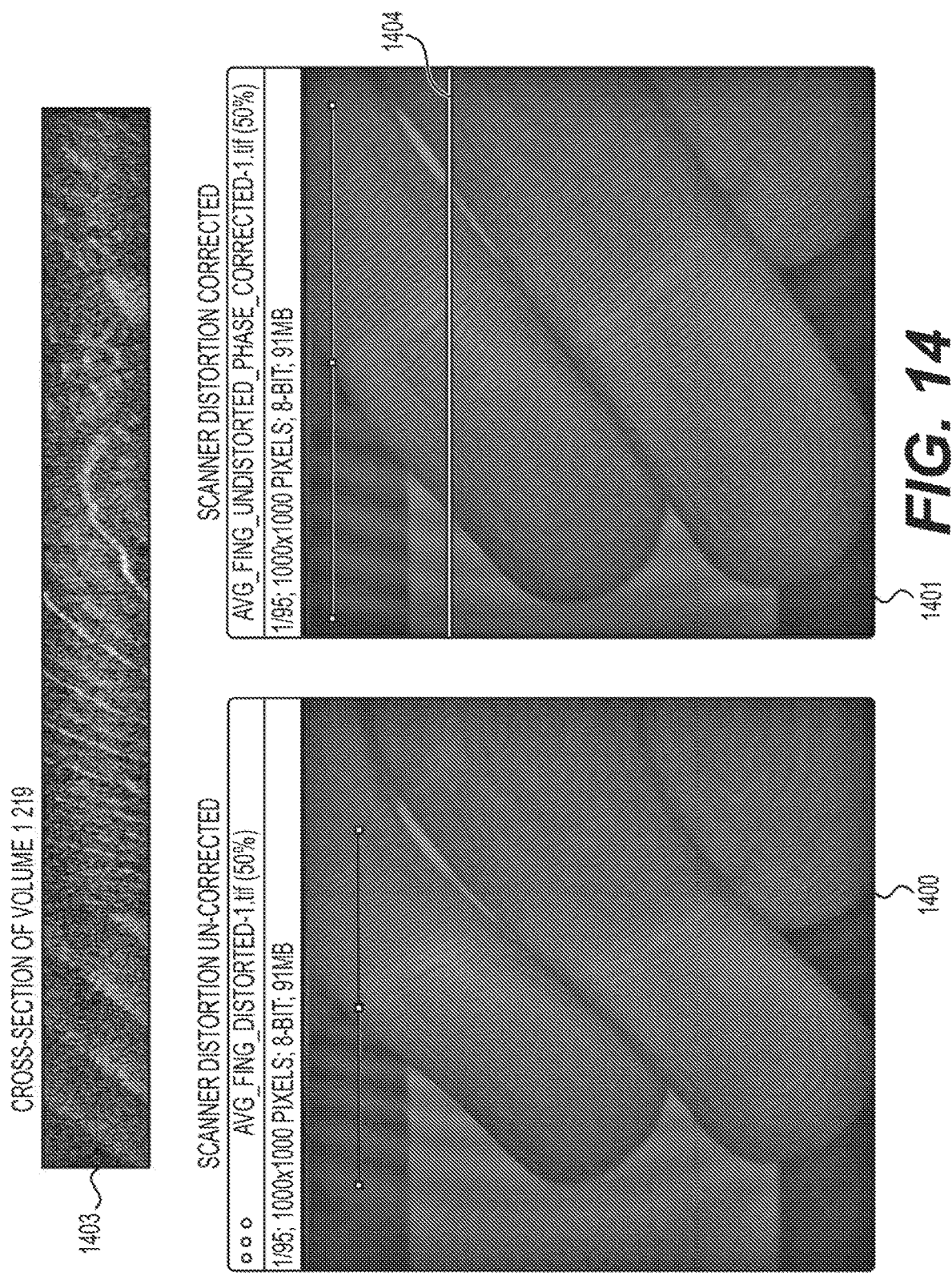
FIG. 14 is an exemplary set of images of a high-speed OS-OCT system.

A further exemplary imaging microscope can also be provided by using, e.g., a 3.9 kHz resonant beam scanner along with a slower galvanometric scanner. It is possible to utilize a 250 mm focusing lens. With the exemplary 3.9 kHz resonant fast-scanner, it is possible to obtain approximately 8 volumes per second while measuring ~2428 pixels in the fast frame and 1000 pixels in the slow frame. This procedure and arrangement facilitated volumetric imaging of samples with each volume acquired at video rate, e.g., at 8 volumes per second. The exemplary volume acquisition rate can be increased significantly by reducing the number of A-lines in the fast frame direction, the slow frame direction, and by increasing the speed of the scanner. This imaging was performed with the 18.9 MHz A-line rate source. Because of the sinusoidal nature of the resonant scanner, as shown in FIG. 14, it was possible to perform a sinusoidal interpolation in the processing to remove this spatial disruption from the original image 1400 in the horizontal direction to create an undistorted image 1401. The $219^{th}$ cross-sectional image 1403 of the first volume at the location 1404 in the exemplary undistorted image 1401 is shown in FIG. 14, and demonstrates how sub-surface features appear in the recorded baseband window. For example, the baseband window size can be changed by changing the FSR of the intra-cavity/external-cavity filters. The images 1400 and 1401 are exemplary average intensity projection images across the depth axis.

In another exemplary embodiment of the system according to the present disclosure, the polarization-diverse volumetric tissue imaging was used to measure the optical birefringence and optical axis of that birefringence within a tissue field, and these volumetric measurements were acquired with the video-rate microscope, allowing video-rate birefringence imaging of a surgical field. In such exemplary embodiment, the four digitizer channels (e.g., digitizer channels 810a, 810b of FIG. 8) were used providing the I/Q measurements of each of the X and Y polarization diverse detection channels. The trigger output of a first digitizer board 810a can be used to trigger the start of acquisition on second digitizer board 810b. The lengths of the optical paths and electrical cables after the interfering PBC 804 were maximally equalized to avoid differential delays that can induce modulation or PS errors. For the polarization sensitive (PS) measurements, for example, a frequency dependent phase shift between the X and Y channels can produce an artifactual birefringence measurement by causing the Y-channel phase to apparently increase relative to the X-channel with depth. This artifact was further removed by delaying the X-channel signals relative to the Y-channel signals in the post-processing performed in the computer arrangements 810a,810b.

Figure 15:
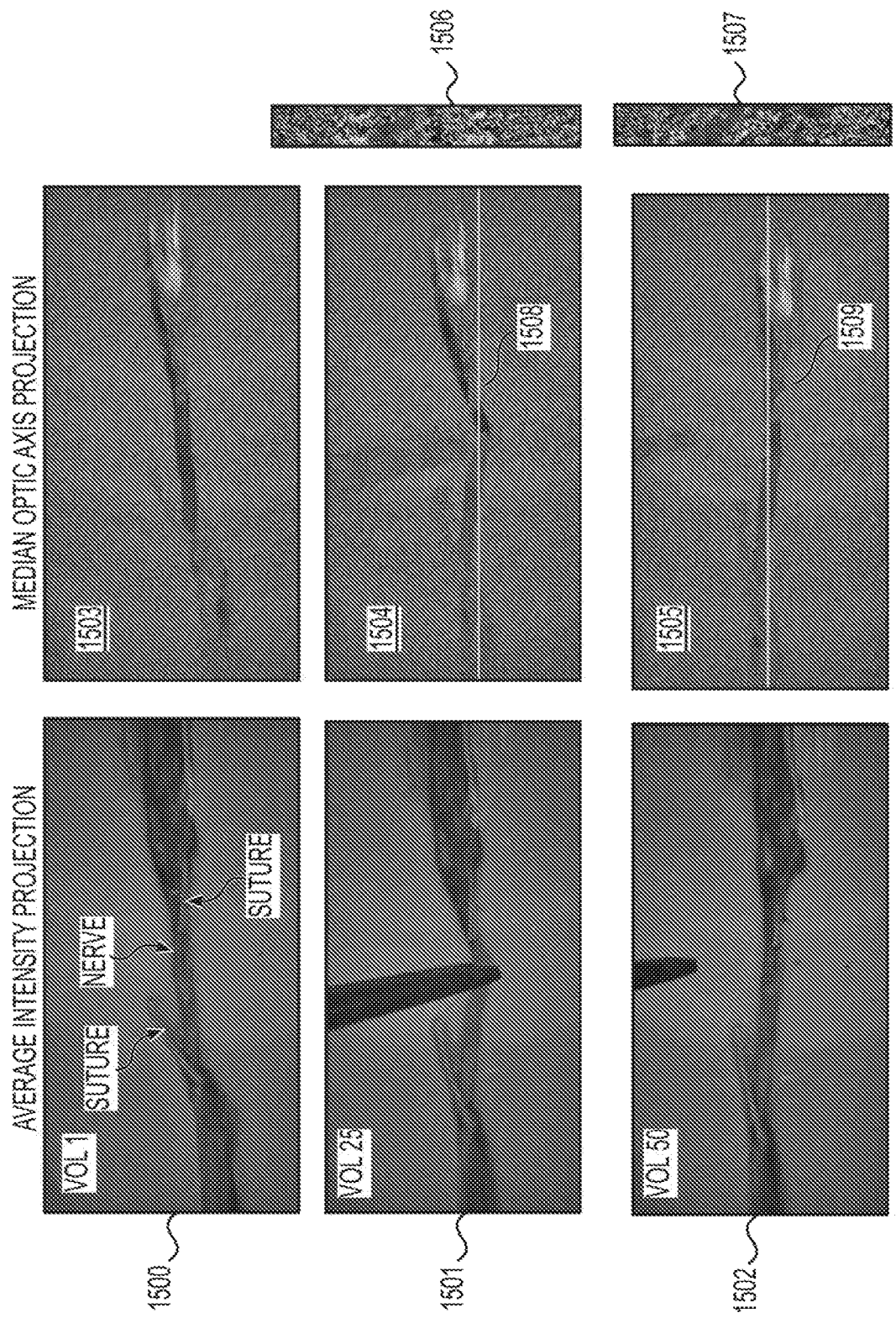
FIG. 15 is an exemplary set of images from a video sequence acquired from an exemplary high-speed OS-OCT system according to an exemplary embodiment of the present disclosure.

FIG. 15 shows an exemplary set of images from a video sequence acquired from an exemplary high-speed OS-OCT system according to an exemplary embodiment of the present disclosure, including snapshots of a video acquired with the exemplary embodiments of the system according to the present disclosure. The exemplary images provided in FIG. 15 illustrate a mouse sciatic nerve resting on a silicon phantom at three time-points (1500, 1501, 1502) using an average intensity projection across depth. During this exemplary time, the nerve was crushed with a pair of forceps. The optical birefringence axis was extracted using known procedures and a median optic-axis projection was performed to generate optical axis images 1503, 1504, 1505. The cross-sectional images of optical axis data 1506 and 1507 are presented at the lines 1508 and 1509, respectively. The optical axis data is displayed where the angle of the optic axis is mapped to color in the images 1503, 1504, 1505, 1506, 1507. In this exemplary dataset, recording lasted for approximately 9 seconds and contained 54 full volumes.

In this example, the fast scanner was operating at 3.945 kHz, and a modulation was performed between input polarization 1 during the forward scan and input polarization 2 during the backward scan (e.g., EOM modulation speed was 3.945 kHz). The slow axis scanner had a speed of 6.514083 Hz, and was driven with a ramp waveform therefore providing 600 transverse forward (fast-axis) scans and 600 backward (fast-axis) scans in a volume. A transverse field of 1.2 cm×1 cm was measured. The depth range of the exemplary subsampled OCT system was approximately 5 centimeters. Such exemplary data was acquired with a 200 GHz output wavenumber spacing yielding a baseband imaging window depth of approximately 500 m in tissue.

In an exemplary embodiment, the polarimetric data can be displayed by mapping the three optical axis parameters of a Stokes representation of polarization to red, green and blue color scales, and then median projecting these color volumetric images across depth to generate a two-dimensional map of tissue optical birefringence 1503, 1504, 1505,1506, 1507.

Figure 16:
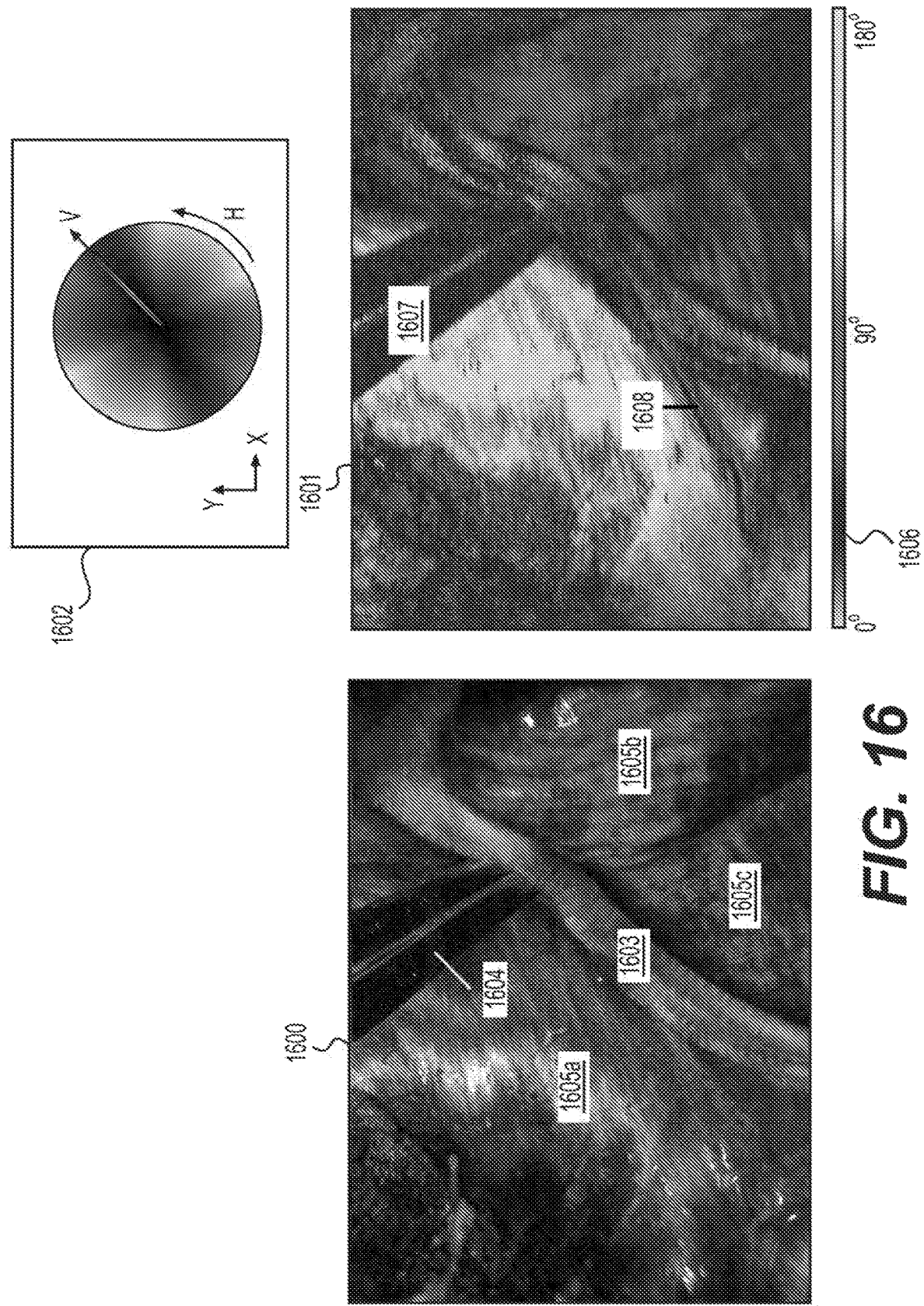
FIG. 16 is a further exemplary set of images provided from an exemplary video sequence generated by an exemplary high-speed OS-OCT system showing polarization-dependent image contrast according to an exemplary embodiment of the present disclosure.

Alternatively, as shown in FIG. 16, exemplary embodiments of the system and method according to the present disclosure can be utilized to display average structural (intensity) projections 1600, or weighted projections with optic axis, retardance, and/or depolarization information 1601. This exemplary image illustrates a surgically exposed rat sciatic nerve 1603 that is being manipulated by forceps 1604 in a field of surrounding muscle 1605a,b,c. The exemplary birefringence projected image 1601 shows optic axis angle mapped onto a circular colormap 1602 wherein the color/hue denotes the optical axis angle in the linear plane orthogonal to the imaging beam propagation direction 1606. Here the value of the hue/color is weighted by intensity and retardance values across depth. This single en face projection is a single capture within a video acquisition with similar acquisition parameters as described for the mouse sciatic nerve image shown in FIG. 15. Samples with low birefringence display with low value (such as, e.g., forceps 1607) and those of high birefringence can be displayed with high value color. Embedded nerves/tissue features, such as 1608, can be visualized in such 3D to 2D projections. In should be understood that there are a multitude of methods for displaying three-dimensional data, and for translating/transferring such exemplary three-dimensional data to a two-dimensional image.

Additional Light Sources Embodiments

The exemplary laser source shown in FIG. 6 and described herein above is directed to one exemplary embodiment of the present disclosure. In further exemplary embodiments, the laser source can include and optical gain based on an optical fiber amplifier, a parametric amplifier, a nonlinear amplifier, and/or a Raman amplifier, among others.

Figure 17:
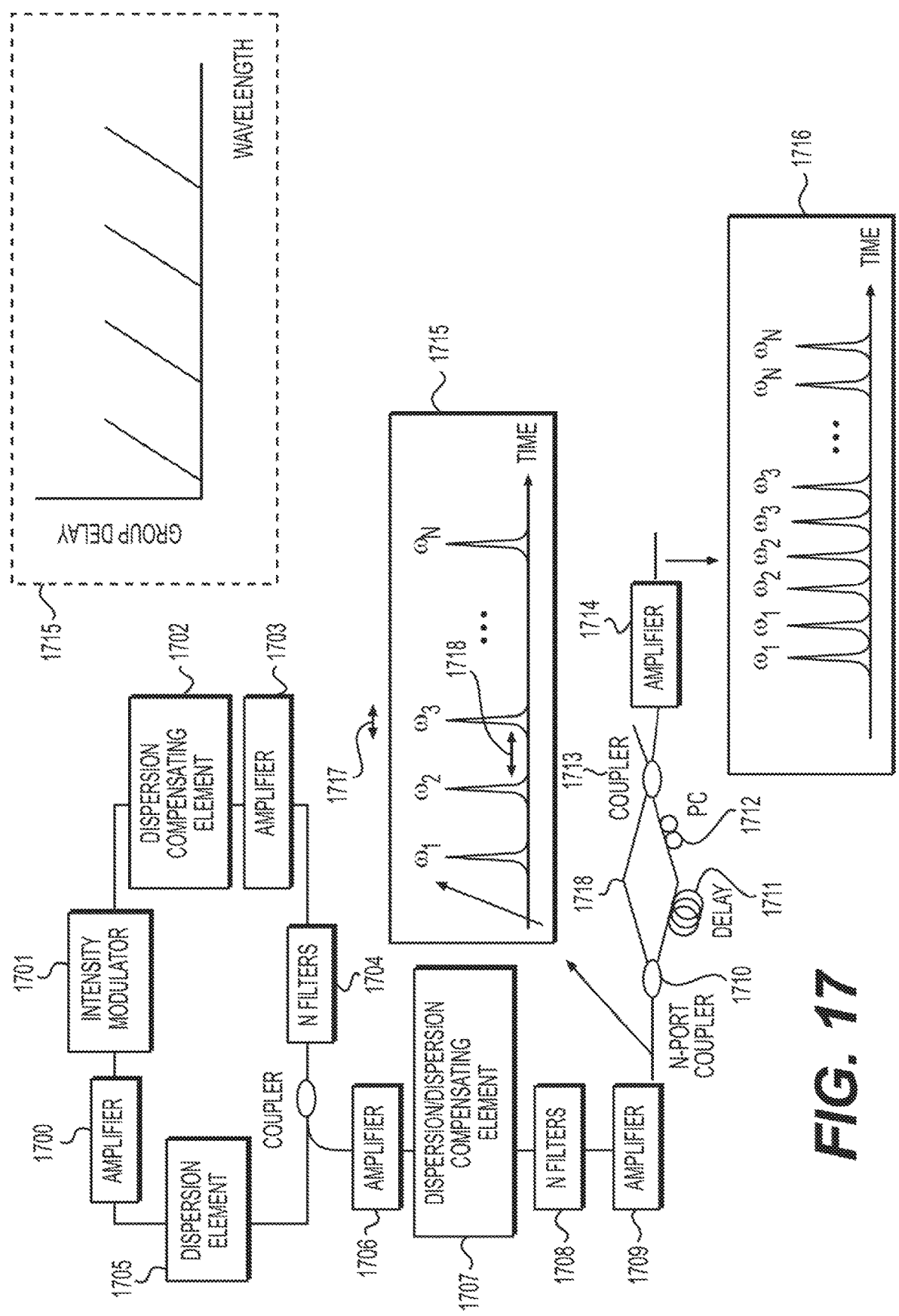
FIG. 17 is a block diagram of an apparatus to interleave laser output pulses from neighboring A-lines to fill temporal gaps in the laser output, and illustrations of exemplary outputs from various components according to an exemplary embodiment of the present disclosure.

FIG. 17 shows a block diagram of an apparatus to interleave laser output pulses from neighboring A-lines to fill temporal gaps in the laser output, and illustrations of exemplary outputs from various components according to an exemplary, embodiment of the present disclosure. In this exemplary embodiment which includes a laser source, the temporal duration of the each wavelength pulse 1717 can be configured by controlling the signal to the intensity modulator to be less than the temporal spacing of the pulses after stretching by the dispersive element in the cavity. This can be performed to limit the overlap of different wavelength pulses in the amplifier or other laser cavity elements, which can also cause a lower laser duty cycle by creating off times 1718 between pulses. Because of these off times, the power of the laser can be concentrated in short pulses 1715, creating higher instantaneous powers that can be disadvantageous by generating nonlinear effects or saturating booster amplifiers. In one exemplary embodiment, such exemplary low-duty cycle pulse trains can be passed through a multi-path optical circuit comprising a coupler 1710, a first arm 1718, a delay 1711 including delay fiber and a polarization controller 1712, and can be recombined using for example a coupler 1713. The delay 1711 can be configured to be, e.g., approximately equal to the A-line repetition rate plus half of the temporal spacing between pulses. This exemplary configuration can interleave adjacent A-lines together without temporally overlapping the pulses 1716.

Alternatively or in addition, a repetitive dispersive element can be used to temporally disperse each of the wavelength pulses without affecting the temporal separation of the pulses. For example, a Gires-Tournois etalon with a FSR matched to that of the wavelength-selective filter or at an integer multiple of the wavelength-selective filter of the laser can be utilized at the laser output to create a large dispersion within the limited bandwidth of each pulse leading to pulse stretching. The exemplary group delay response of this filter can be periodic 1715 such that each pulse is temporally broadened (or compressed if configured in such exemplary manner) without inducing a significant modification of the pulse-to-pulse spacing. The exemplary laser as shown in FIG. 6 can include amplifiers 1700, 1703, 1706, 1709, dispersion elements 1705, 1702, 1707, spectral filters 1704, 1708 and an intensity modulator 1701 illustrated in FIG. 17.

In another exemplary embodiment of the present disclosure, the wavelength selective filter can be constructed from an air-cavity Fabry-Perot etalon which has the advantage of not using a dispersive media in the etalon and maintaining a constant free spectral range across a large bandwidth. Alternative wavelength filter configuration can include fiber-based Fabry-Perot etalons, virtually imaged phase array gratings, fiber-Bragg gratings or other waveguide Bragg gratings, arrayed waveguide gratings, cyclic arrayed waveguide gratings, or optical interleavers and deinterleavers, among others.

Figure 18:
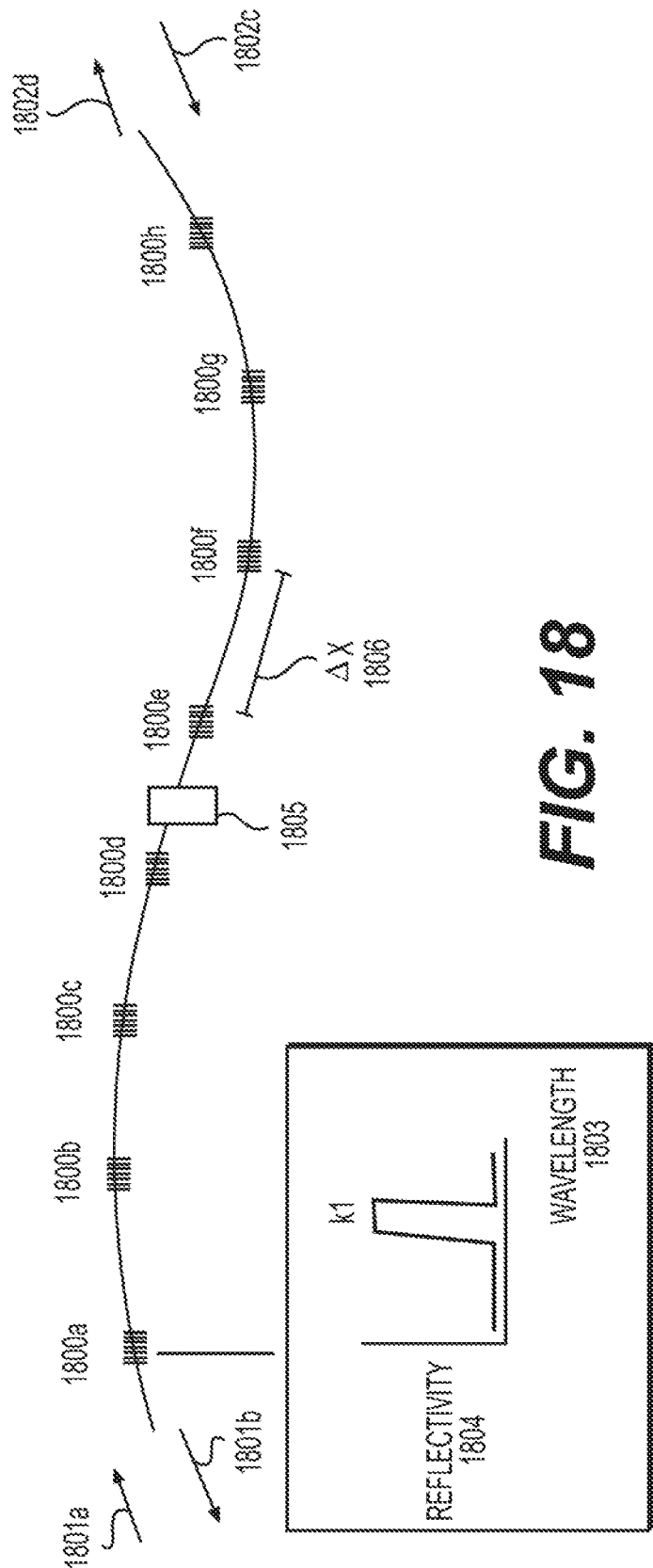
FIG. 18 is an exemplary illustration of a fiber-Bragg grating array, and an exemplary graph of an output provided from one of the components thereof according to an exemplary embodiment of the present disclosure.

According to yet another exemplary embodiment, the dispersive elements within the laser cavity (shown in FIG. 6 as components 612, 615) can be based on fiber Bragg grating (FBG) arrays or a long chirped fiber Bragg grating. For example, the dispersion is created by the different spatial location of reflection of each wavelength. FIG. 18 illustrates an exemplary illustration of a fiber-Bragg grating array, and an exemplary graph of an output provided from one of the components thereof according to an exemplary embodiment of the present disclosure. In an exemplary FBG array configuration shown in FIG. 18, a set of individual FBGs 1800a-1800h can be located along a fiber separated by a distance Δx 1806 such that reflected pulses from each sequential grating are separated in time by $(c/(2n\ \Delta x))^{\wedge}-1$, where c is the speed of light and n is the index of refraction of the fiber. For example, the individual FBGs 1800a-h can serve as the wavelengths selective filter such that a FP etalon or a similar periodic filter is not required, and the FBG reflection wavelengths define the lasing wavelengths. Alternatively or in addition, the spectral location of the FBG reflectivities can be aligned to the wavelengths passed by the wavelength selective filter such as an intra-cavity FP etalon. H The exemplary reflection bandwidth of the FBGs can be broad such that the laser line width is determined by the etalon line width. A variable optical attenuator 1805 can be included in the array to, e.g., limit the number of reflected pulses to reduce the number of lasing wavelengths. The input light from one side 1801a can be reflected and thereby creates an output light 1801b with each wavelength providing a different group delay based on the location of the FBG that aligns to its wavelength, or to the first FBG encountered by the light that matches to its wavelength. The exemplary FBG array configuration can also be used from both sides, with light launched form the other end 1802c reflecting off the same gratings and returning 1802d and can have the opposite dispersion as that achieved in the reflected light 1801b due to the input light 1802a seeing the FBGs in the reverse order. Alternatively or in addition, a second FBG array can be used to create an opposite dispersion with the order of the gratings in this array reversed. The FBG reflectivity 1804 versus wavelength 1803 can be tailored by the grating writing process to configure its line width, reflectivity, phase response, and center wavelength as shown in the graph of FIG. 18.

In a further exemplary embodiment, a chirped FBG can be used that provides continuous wavelength reflectivity along the fiber length. For example, a wavelength selective filter in the cavity can define the lasing wavelength and the chirped FBG can create the positive and negative dispersion(s). As with the exemplary FBG array, the same chirped FBG can be used to create positive and negative dispersion(s) by launching from opposite sides. The reflectivity of the chirped FBG can be designed to induce a specific laser output profile and/or to compensate for wavelength-dependent loss or gain in the cavity. The exemplary laser can be configured without a wavelength selective filter in the cavity to, for example, generate a continuous wavelength-swept output providing a laser source for high-speed conventional FD-OCT.

The spacing of the exemplary FBGs in a FBG array can be, for example, about 5 cm (Δx=5 cm) in fiber, thereby producing a 0.5 ns temporal displacement between reflections of light at wavelengths corresponding to adjacent FBGs. For example, FBGs can be placed closer to shorten this time separation, and further to lengthen it. FBG arrays of tens of centimeters through hundreds of meters can be provided.

To reduce or otherwise minimize the transmission of light through a FBG array or a continuously chirped FBG dispersive element, the reflectivity of the grating can be made close to 100%, limiting significantly the transmission. This can be done, for example, to prevent a lasing path within the laser cavity that by-passes the intensity modulator.

Figure 19:
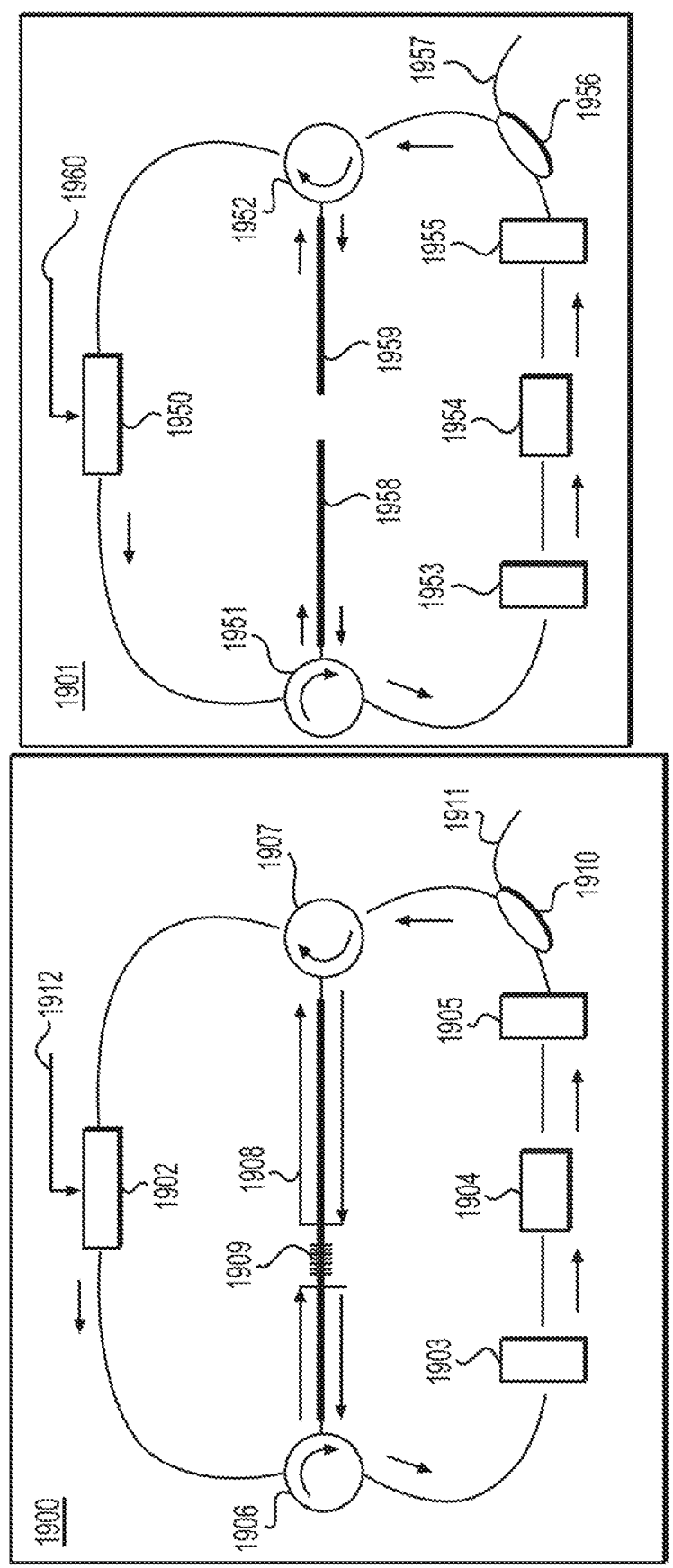
FIG. 19 is a set of diagrams of an exemplary laser source utilizing fiber Bragg gratings according to an exemplary embodiment of the present disclosure.

FIG. 19 shows a set of diagrams of an exemplary laser source utilizing fiber Bragg gratings according to an exemplary embodiment of the present disclosure. In particular, the exemplary embodiments of the laser containing a single FBG array or continuously chirped FBG and the exemplary embodiment providing a pair of FBG arrays or continuously chirped FBGs are illustrated in FIG. 19. For example, in the single FBG array/continuously chirped FBG configuration 1900, an intensity modulator 1902, circulators 1906, 1907, optional wavelength selective filters 1903, 1905, and an optical amplifier 1904 and output coupler 1910 are shown in FIG. 19. For example, light or other electro-magnetic radiation is/are output on port 1911. The wavelength selective filters can be or include, for example, a Fabry-Perot etalon or other periodic spectral filter. A positive dispersion can be generated by light entering the FBG array and/or continuously chirped FBG 1908 from the left, and compensating negative dispersion is created by light entering the FBG array or continuously chirped FBG 1908 from the right. Alternatively or in addition, the exemplary FBG device/configuration 1900 can be configured to generate negative dispersion on light entering from the left and positive dispersion on light entering from the right. An exemplary single FBG 1909 is provided within an FBG array, and providing the light reflection path from the left side and the right side. It should be understood that this can be one of many FBGs that can be located in the fiber 1908, as shown in FIG. 18.

In an alternative exemplary embodiment of the present disclosure of a exemplary configuration 1901 shown in FIG. 19, the exemplary laser can include the same intensity modulator 1950, circulators 1951,1952, wavelength selective filters (optional) 1953,1955, optical amplifier 1954, and output coupler 1956 with light or other electro-magnetic radiation exiting on fiber 1957. For example, gratings 1958, 1959 can be used and there is likely no transmissive path from the grating 1958 to the grating 1959. The grating 1958 can be configured or structured to create positive dispersion, the grating 1959 can be configured or structured to create negative dispersion matched in magnitude to the positive dispersion grating 1958, for example, or vice versa. Drive signals 1912, 1960 can be used to actuate the intensity modulators 1902, 1950, respectively. These drive signals can be generated from a pulse generator or a computing arrangement. Such exemplary embodiments and further described exemplary embodiments of the laser system according to the present disclosure can include more or fewer wavelength selective filters and gain medium, and the exemplary components could be organized in a different configuration or manner within such exemplary cavity.

Figure 20:
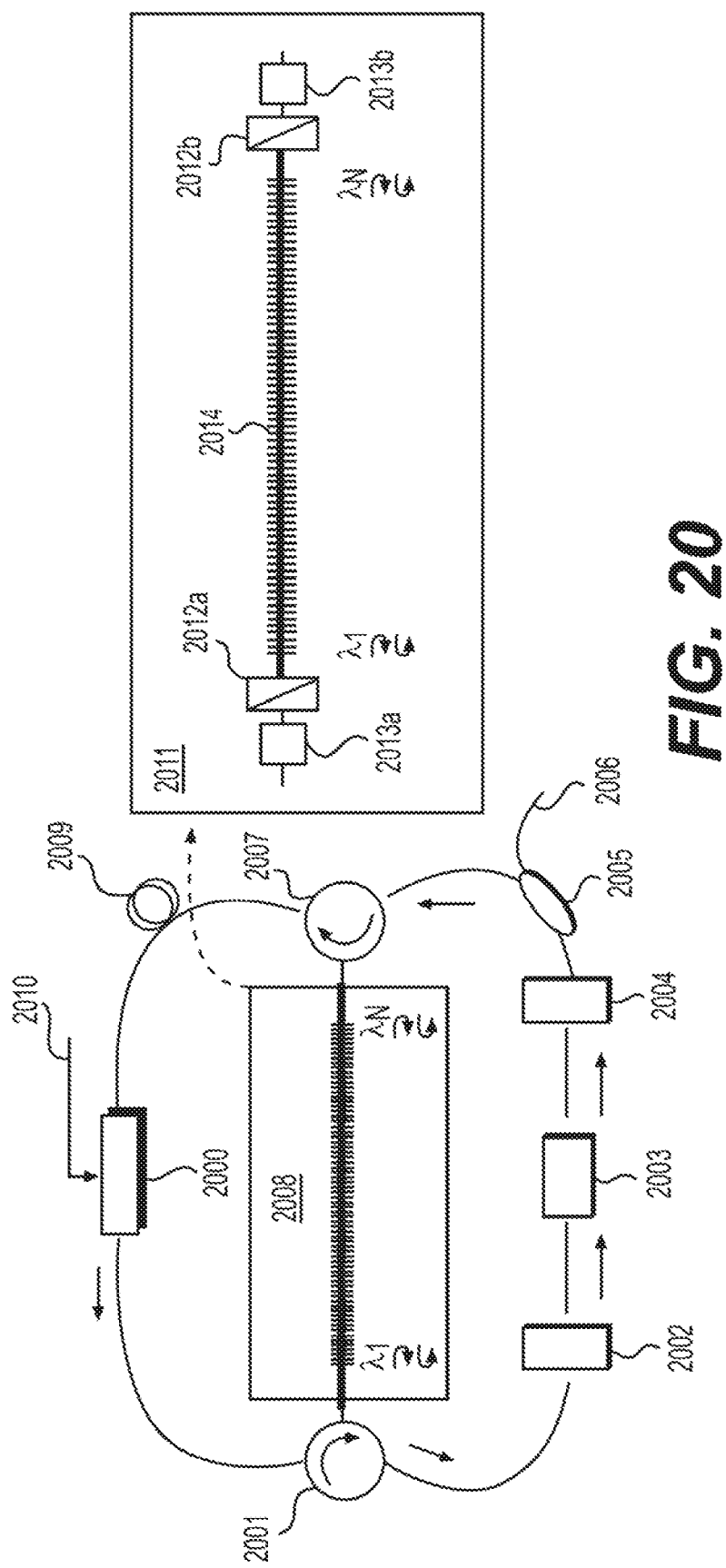
FIG. 20 is a set of diagrams of an exemplary laser source utilizing a continuously chirped fiber Bragg grating according to an exemplary embodiment of the present disclosure.

In the exemplary embodiment of the laser system shown in FIG. 20, the exemplary laser can utilize a continuously chirped FBG 2008, as well as an intensity modulator 2000 driven by a drive signal 2010, circulators 2001,2007, wavelength selective filters (optical) 2002, 2004, an optical amplifier 2003, and an output coupler 2005. Light or other electro-magnetic radiation can be output on a fiber 2006. A dispersion compensating element/configuration 2009 can be provided to correct for mismatched dispersion created from the exemplary FBG system 2008.

In a further exemplary embodiment, an FBG array or continuously chirped FBG can be provided from a polarization-maintaining fiber to ensure that reflected light or other electro-magnetic radiation from all wavelengths is in approximately the same polarization state. The exemplary FBG array or continuously chirped FBG can additionally be provided in reduced cladding mode fiber to remove sidemodes in the FBG reflectivity.

In another exemplary configuration, an FBG array or continuously chirped FBG can be based on polarization-maintaining (PM) fiber and the light or other electro-magnetic radiation entering from one side can be launched along a fast axis, and the light launched from the other side can be launched along the slow axis. In this exemplary configuration that uses a FBG array, the shift in the reflectivity of each grating in the fast and slow axis can be configured to match the wavelength spacing of the laser. Using such exemplary embodiment, it is possible to prevent lasing due to light transmission through the grating by for example placing polarizers one or both sides of the grating 2011. For example, polarizers 2012a, 2012b can be used with polarization controllers 2013a, 2013b. Light or other electromagnetic radiation launched in the fast axis from the left through polarizer 2012a and that is transmitted through the grating 2014 can be blocked by the polarizer 2012b. The reflectivity of the FBGs can be configured to induce a specific laser output profile or to compensate for wavelength-dependent loss or gain in the cavity.

In a still further exemplary embodiment, the WSF element can be omitted from the cavity and the FBG array can define the lasing wavelengths and the line width of each lasing wavelength depends on the bandwidth of the reflectivity of each FBG. Alternatively or additionally, a continuously chirped FBG array can be used as dispersive elements without additional wavelength selective elements and creating a continuously swept wavelength source.

Figure 21:
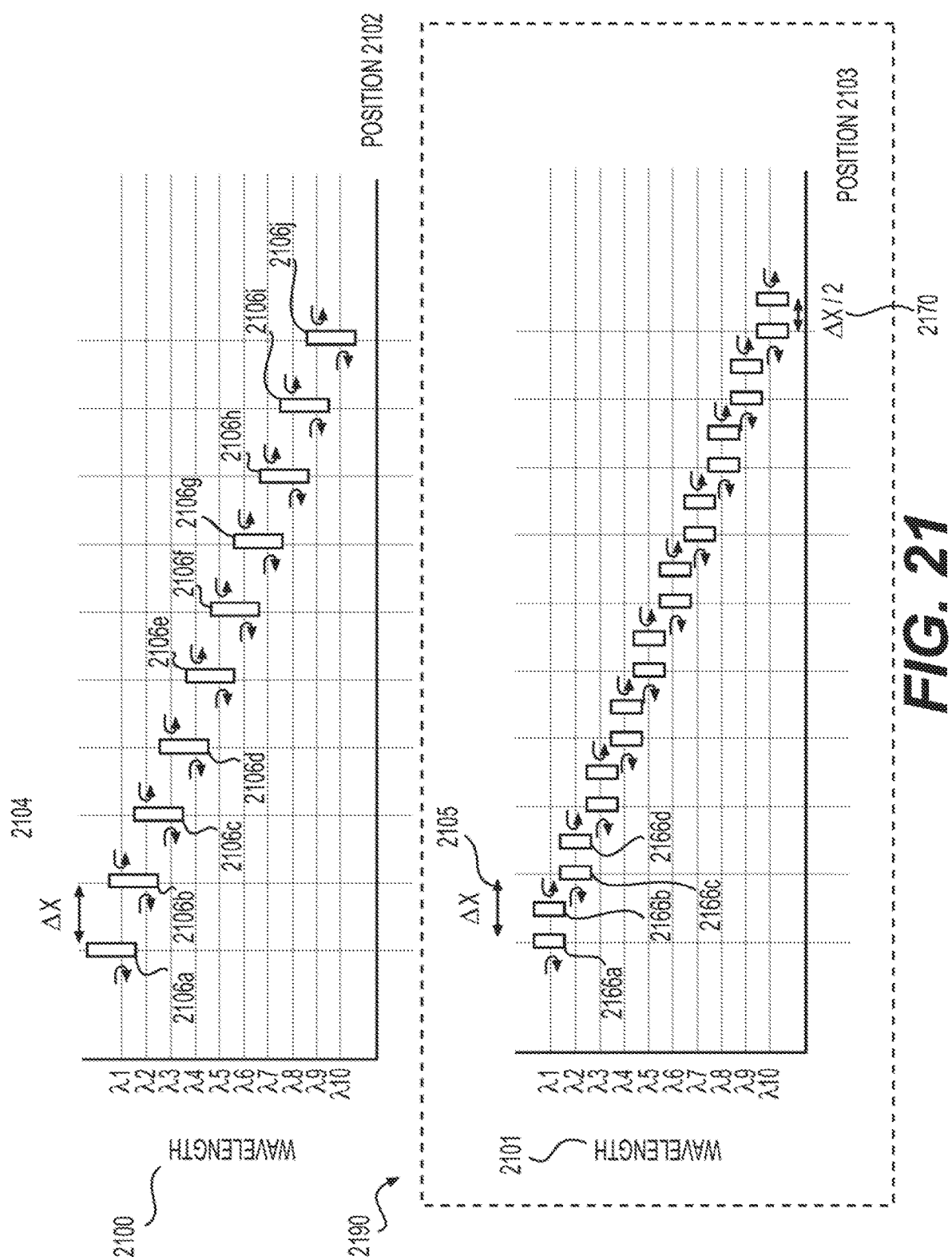
FIG. 21 is an exemplary illustration of an exemplary grating design arrangement in a fiber Bragg grating array used in a laser source according to an exemplary embodiment of the present disclosure.

In another exemplary embodiment, an FBG array can be used and configured to limit the transmission through the array which can be used to prevent light circulation in an unintended path. For example, FIG. 21 shows an exemplary illustration of an exemplary grating design arrangement in a fiber Bragg grating array used in a laser source according to an exemplary embodiment of the present disclosure. As shown in FIG. 21, the individual FBGs 2106a-2106j can be located along the position axis 2102 as a function of their reflection wavelength 2100, such that each grating reflection profile can occupy two laser wavelengths $\lambda 1$-$\lambda 10$. For example, the grating 2106b reflects light at $\lambda 2$ and $\lambda 1$. However, light at $\lambda 1$ from the left is largely reflected by the prior grating 2106a. Thus, the grating 2106b can provide the primary reflection point for light at $\lambda 2$ and serves to reduce the transmission of light at $\lambda 1$ that is transmitted through grating 2106a. From the right side, 2106b can provide the primary reflection of light at $\lambda 1$, and 2106a reduces transmission of light at $\lambda 1$. Because light from the left and right are primarily reflected from different gratings, the grating positions can be spaced by a consistent spacing $\Delta x$ 2104 such that the total cavity group delay experienced by each wavelength is approximately the same.

In an alternative exemplary embodiment, the FBG array used to create dispersion can include two or more gratings at each wavelength 2101 and position 2103 as shown in panel 2190 of FIG. 21. For example, a first grating 2166a reflects light at $\lambda 1$ from the left, and a second grating 2166b suppressed the transmission by reflecting the small light transmitted through 2166a. The spacing of the grating pairs 2166a, 2166b and 2166c, 2166d and others can be, for example, half of the spacing of the gratings 2166a, 2166c, e.g., $\Delta x/2$ 2170 compared to $\Delta x$ 2105. For example, $\Delta x$ can be 5 cm. In these examples, if each grating has a 90% reflectivity, approximately 10% of the light is transmitted. Thus, the second grating 2166b further reduces transmission by about 10%, yielding approximately 1% transmission.

Figure 22:
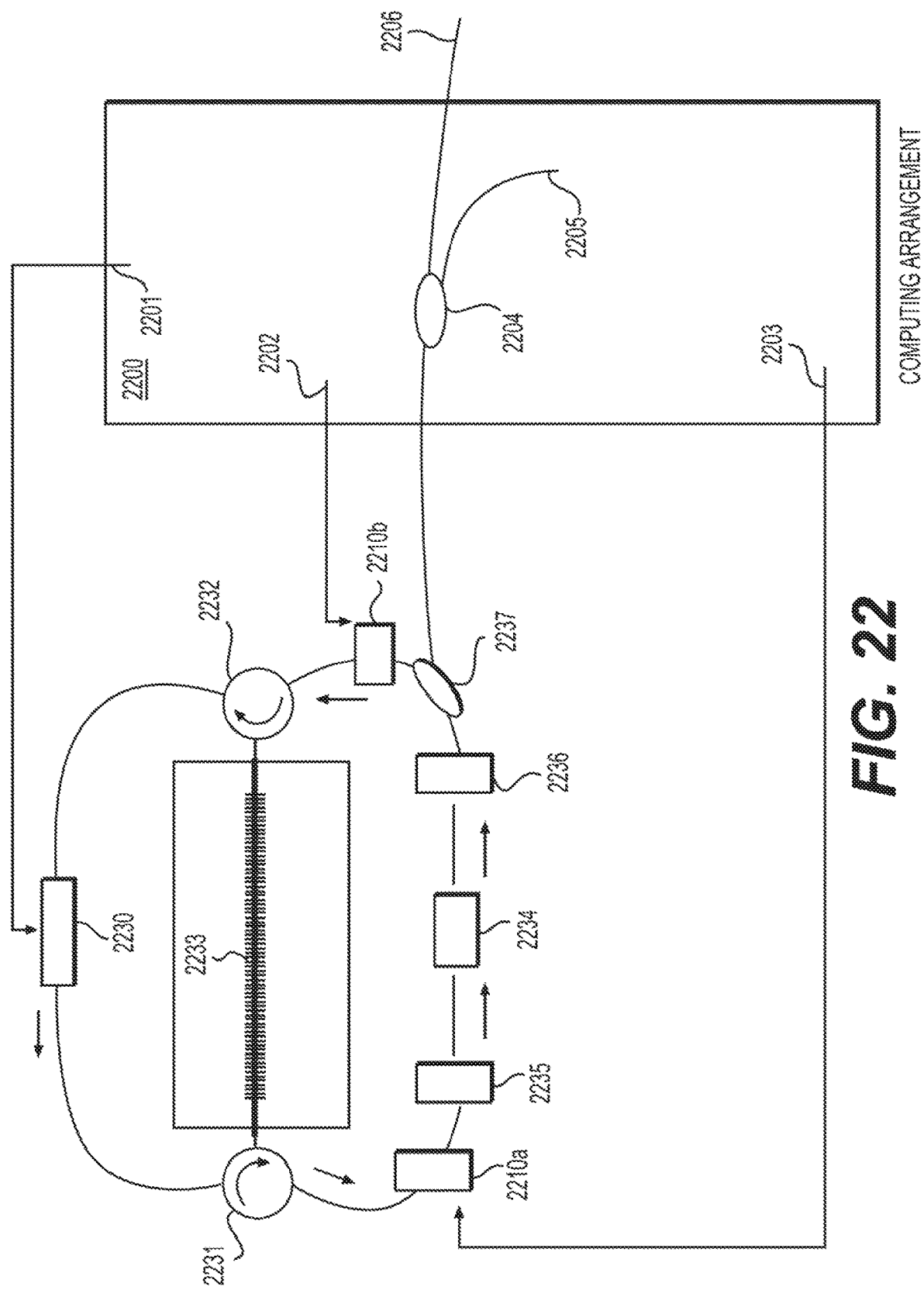
FIG. 22 is a diagram of an exemplary laser source utilizing an active polarization control according to an exemplary embodiment of the present disclosure.

FIG. 22 illustrates a diagram of an exemplary laser source utilizing an active polarization control according to an exemplary embodiment of the present disclosure. In this exemplary embodiment, the exemplary configuration is provided to minimize the effect of polarization rotation at each wavelength in a FBG configuration. As shown in FIG. 22, a laser cavity comprises an intensity modulator 2230, circulators 2231, 2232, a FBG dispersive element 2233, a wavelength selective filter (optional) 2235, 2236, an optical amplifier 2234 also incorporates active polarization modulators 2210a, 2210b. These modulators 2210a, 2210b can be used to align the polarization state of each wavelength pulse to a predetermined state using control signals 2203, 2202 respectively. The laser output from a coupler 2237 can be directed to a computing/controller arrangement 2200 that can include a tap coupler 2204 to direct laser output power to a detector 2205 and to a further optical output 2206, and can adjust the polarization drive signal for each pulse by for example maximizing the output power. This exemplary optimization can be performed on a pulse-by-pulse bases, providing an exemplary correction waveform that can be communicated to the polarization modulators 2210a, 2210b. For example, such exemplary computing arrangement 2200 can be the same arrangement used to generate the drive signal 2201 for the intensity modulator 2230.

Figure 23:
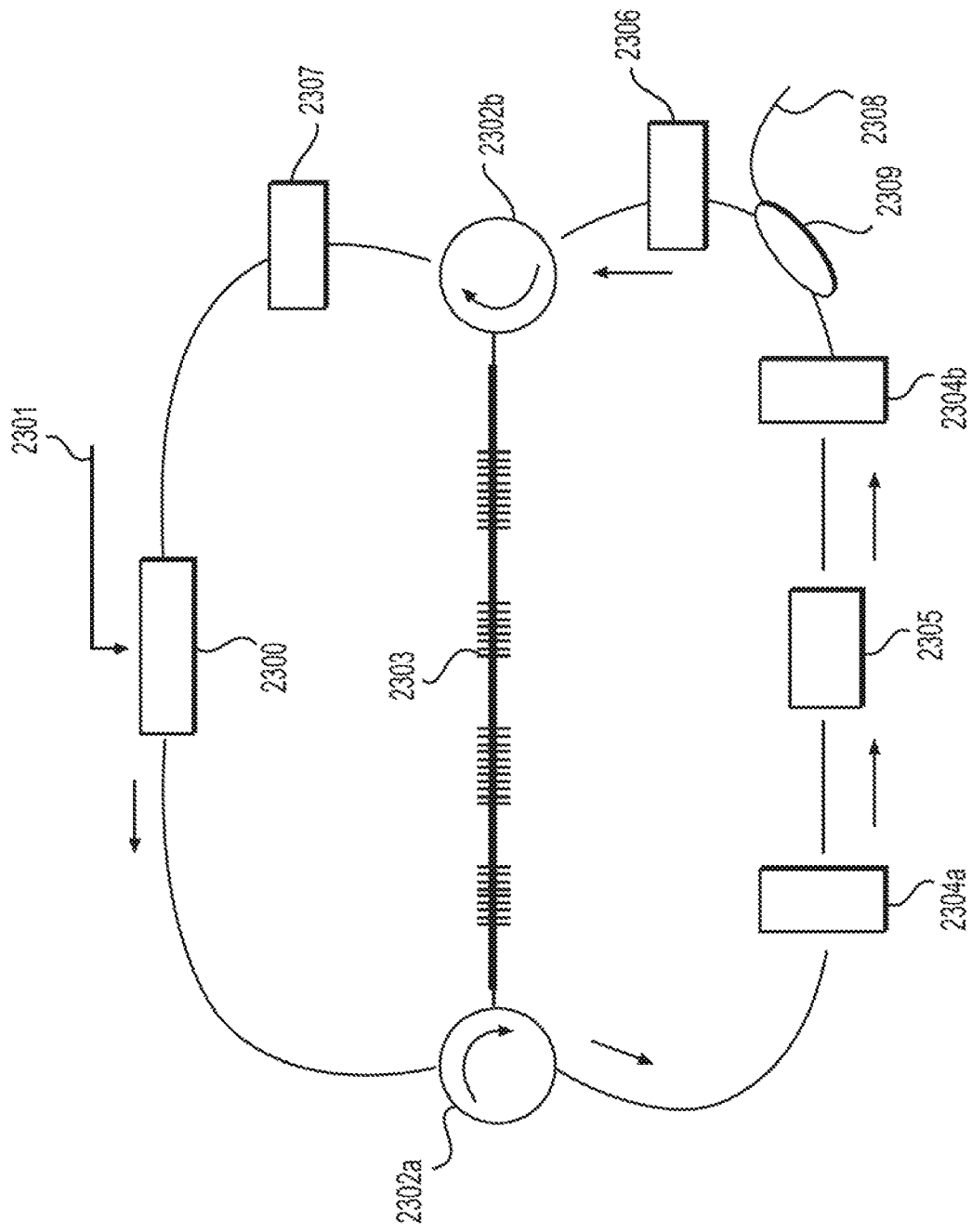
FIG. 23 is a diagram of an exemplary laser source incorporating frequency or phase shifters to limit light circulation in a specific path according to an exemplary embodiment of the present-disclosure.

FIG. 23 shows a diagram of yet another exemplary laser source incorporating frequency or phase shifters to limit light circulation in a specific path according to an exemplary embodiment of the present disclosure. As shown in FIG. 23, a laser cavity is provided which comprises an intensity modulator 2300 (driven by a signal 2301 from a computing arrangement or a pulse generator), circulators 2302a, 2302b, wavelength selective filters 2304a, 2304b, an optical amplifier 2305, an output coupler 2307, and a bi-directional dispersion element 2303, such as, e.g., a FBG array or a continuously chirped FBG, and can also include optical frequency shifters 2306, 2307 that can be used to suppress light or radiation propagation in the path from 2302b through the bi-directional dispersion element 2303 to the circulator 2302a to the optical amplifier 2305 and back to the circulator 2302b (bypassing the modulator 2300). The first frequency shifter 2306 can induce a frequency shift +F, and the second frequency shifter can induce a frequency shift of −F.

The light/radiation that passes through the first and second frequency shifters 2306, 2307 therefore likely have no net frequency shift. However, light/radiation that circulates without seeing the intensity modulator are continuously upshifted by +F per round trip. +F can be for example 1 GHz and the line width of the wavelength selective filters 2304a,b can be for example 1 GHz. This can cause the light/radiation to walk-off from the pass band of the wavelength selective filters and suppress light circulation in this path. In the exemplary case of an FBG array, the line width of the bi-directional dispersion element 2303 can be configured to be sufficiently wide-band to reflect light that is upshifted once +F by the frequency shifter 2306. The frequency shifters 2306, 2307 can be constructed, for example, using acousto-optic frequency shifters or electro-optic modulators, and can additionally be or include phase modulators. In another exemplary embodiment configured to use phase modulators, the second phase modulator 2307 can induce a phase modulation that is opposite to that induced by the first phase modulator 2306. In this exemplary manner, the first phase modulator can spectrally broaden the light, while the second phase modulator compensates for this broadening and allows the light to pass through the wavelength selective filter pass band. The laser output 2308 is provided by the output coupler 2309.

Figure 34:
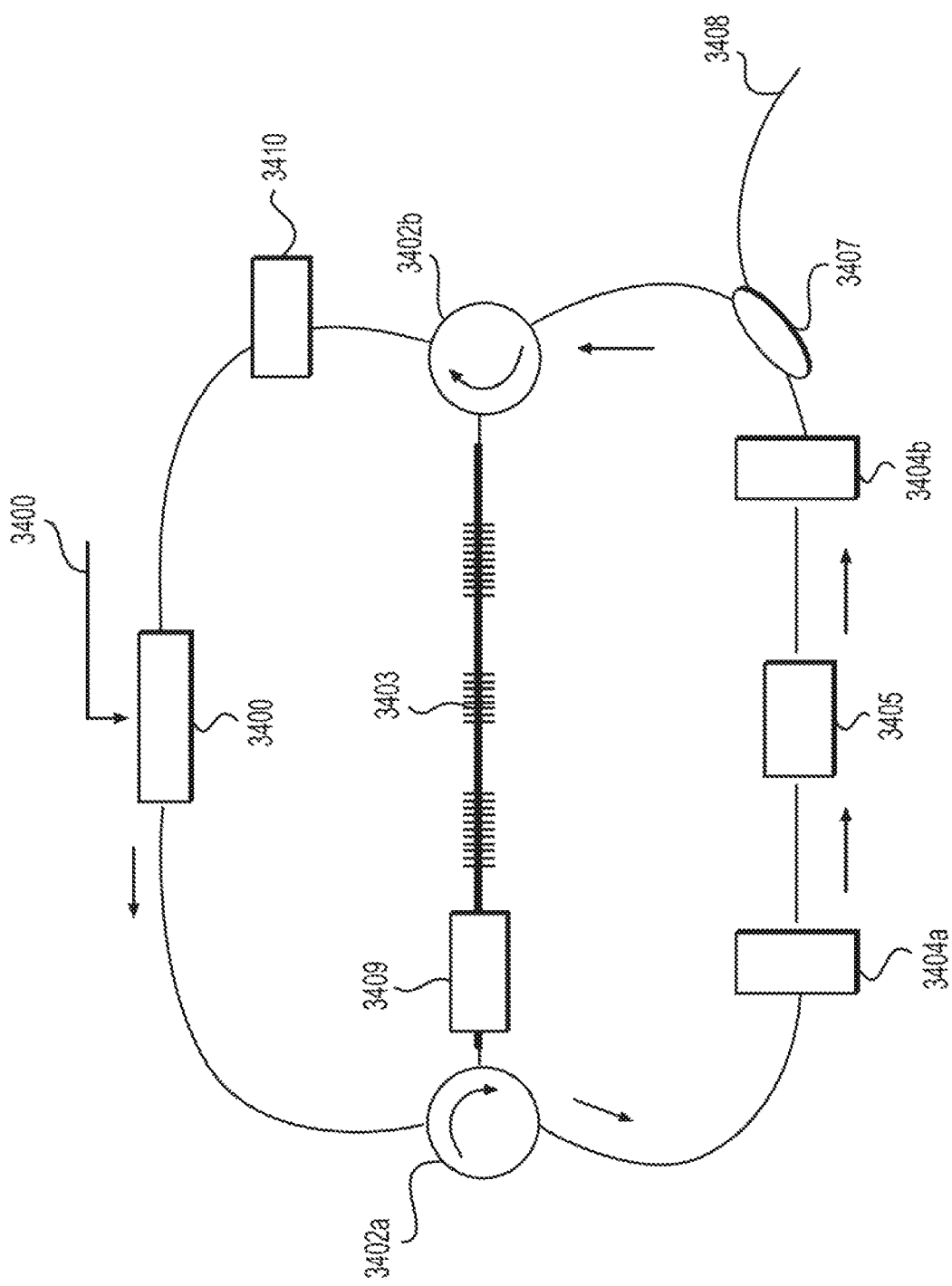
FIG. 34 is a diagram of an exemplary OS-OCT laser including optical gain within a reflective dispersion element according to an exemplary embodiment of the present disclosure.

In a similar exemplary embodiment illustrated in FIG. 34, a frequency shifter can be placed in the path of a circulator 3402a that is not placed in the path of another circulator 3402b. A frequency shifter 3409 can induce a shift of +F during each pass through it. When light passes in the preferred cavity (through an intensity modulator 3400), a double pass through the frequency shifter 3409 can cause a shift of +2F, which will be aligned with the pass-band of the wavelength selective filters 3404a,b. The bi-directional dispersion element will have reflections aligned to the pass-bands of wavelength selective filters 3404a, 3404b plus +F. A second frequency shifter 3410 can induce a shift of −2F, thus the light/radiation directed toward the intensity modulator 3400 can have a zero net frequency shift. The path from the circulator 3402b through a bi-directional dispersion element 3403 to the circulator 3402a to an optical amplifier 3405 and back to the circulator 3402b, however, can have a +F shift through every roundtrip of this path, and can induce a walk-off from the wavelength selective filter 3404a, 2404b pass band. As show in in FIG. 34, this exemplary system can include the optical amplifier 3405, an output coupler 3407 providing optical output 3408, and the modulator 3400 can be driven by a drive signal 3401.

Figure 35:
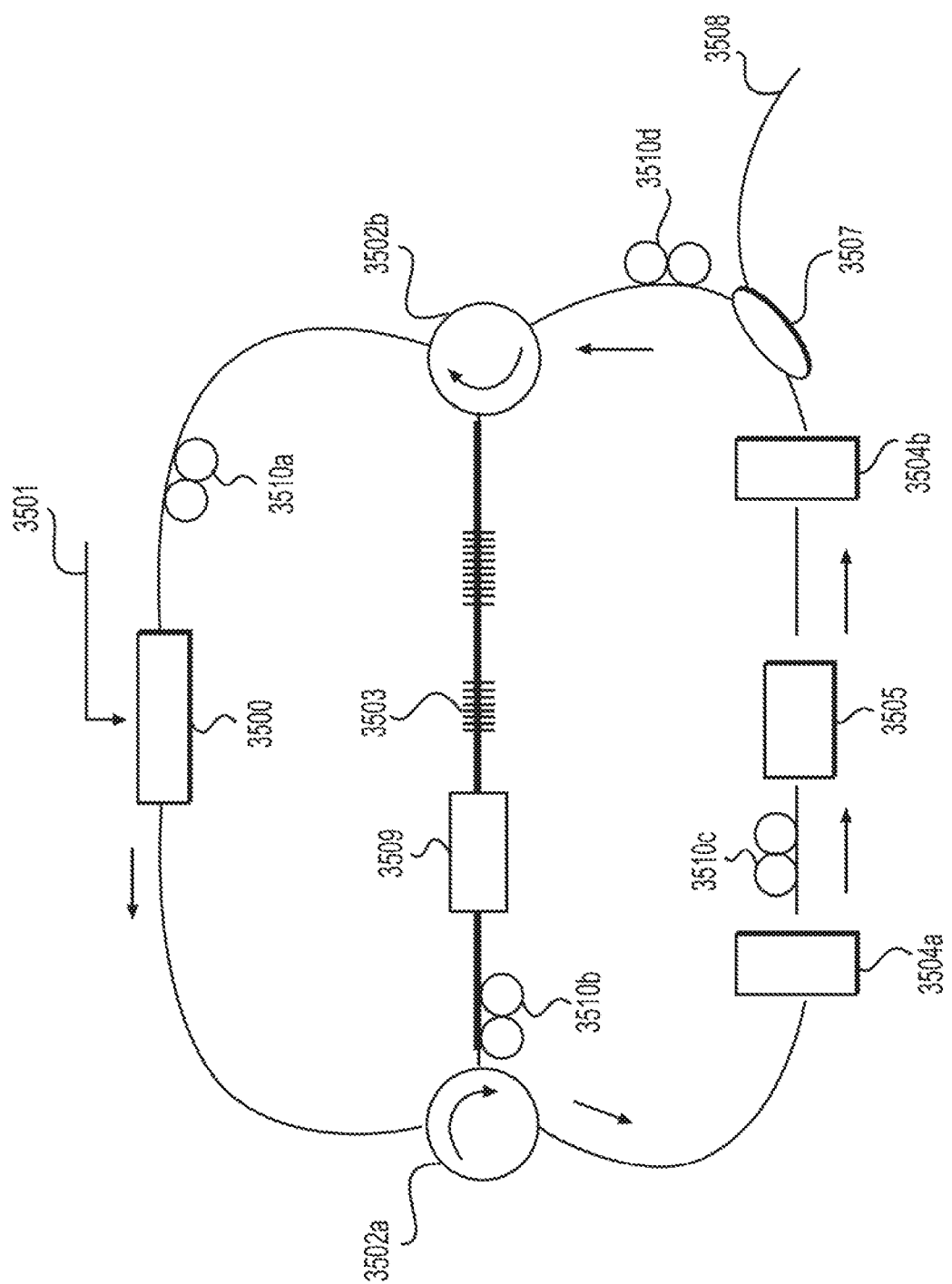
FIG. 35 is a diagram of an exemplary OS-OCT laser including a polarizer and configured by polarization controllers to suppress light circulation in specific sub-cavity according to an exemplary embodiment of the present disclosure.

FIG. 35 shows a diagram of an exemplary OS-OCT laser including a polarizer and configured by polarization controllers to suppress light circulation in specific sub-cavity according to an exemplary embodiment of the present disclosure. For example, such exemplary system can be configured to limit light circulation in an unintended path, a component 3509 is placed in the path of the circulator 3502a that is not placed in the path of 3502b (FIG. 35). The preferred cavity traveling through the intensity modulator 3500 will travel double-pass through this component while light/radiation traveling though the unintended path (bypassing an intensity modulator 3500) and via a single pass. For example, an exemplary laser cavity shown in FIG. 35 comprise an intensity modulator 3500 (driven by a signal 3501 from a computing arrangement or a pulse generator), circulators 3502a, 3502b, wavelength selective filters 3504a, 3504b, an optical amplifier 3505, an output coupler 3507, and a bi-directional dispersion element 3503, such as a FBG array or a continuously chirped FBG that can also include a non-isolated gain medium 3509 that is placed in the double pass path of the circulator 3502a. The gain of the cavity that travels through the intensity modulator 3500 in a cavity path 3500 can exceed the gain of the path from the circulator 3502b through a bi-directional dispersion element 3503 to the circulator 3502a to an optical amplifier 3505 and back to the circulator 3502b, which passes through the gain medium 3509, e.g., once instead of twice. Polarization controllers 3510a-3510d can be placed at various locations within the cavity to maximize/minimize transmission or gain through components within the cavity.

In another exemplary embodiment, the exemplary system can be provided to limit light/radiation circulation in an unintended path, and thus the component 3509 can be a polarizer. The light/radiation traveling in this path can be set to X polarization state by polarization controller 3510b and the polarizer 3509 can be set to pass this polarization state. Light/radiation reflecting from the bi-directional dispersion element 3503 can be configured using polarization controllers to return in the X polarization state, and pass through the polarizer 3509. In particular, the light/radiation that is transmitting through the bi-directional dispersion element 3503 can be configured using polarization controllers to have an orthogonal Y polarization state (as set by a polarization controller 3510d) and can be attenuated by the polarizer 3509. This polarizer 3509 can be placed anywhere in the path connecting components 3502a, 3505, 3502b, and 3503. For example, the optical amplifier 3505 can serve as a polarizer because of its polarization-dependent gain.

Figure 24:
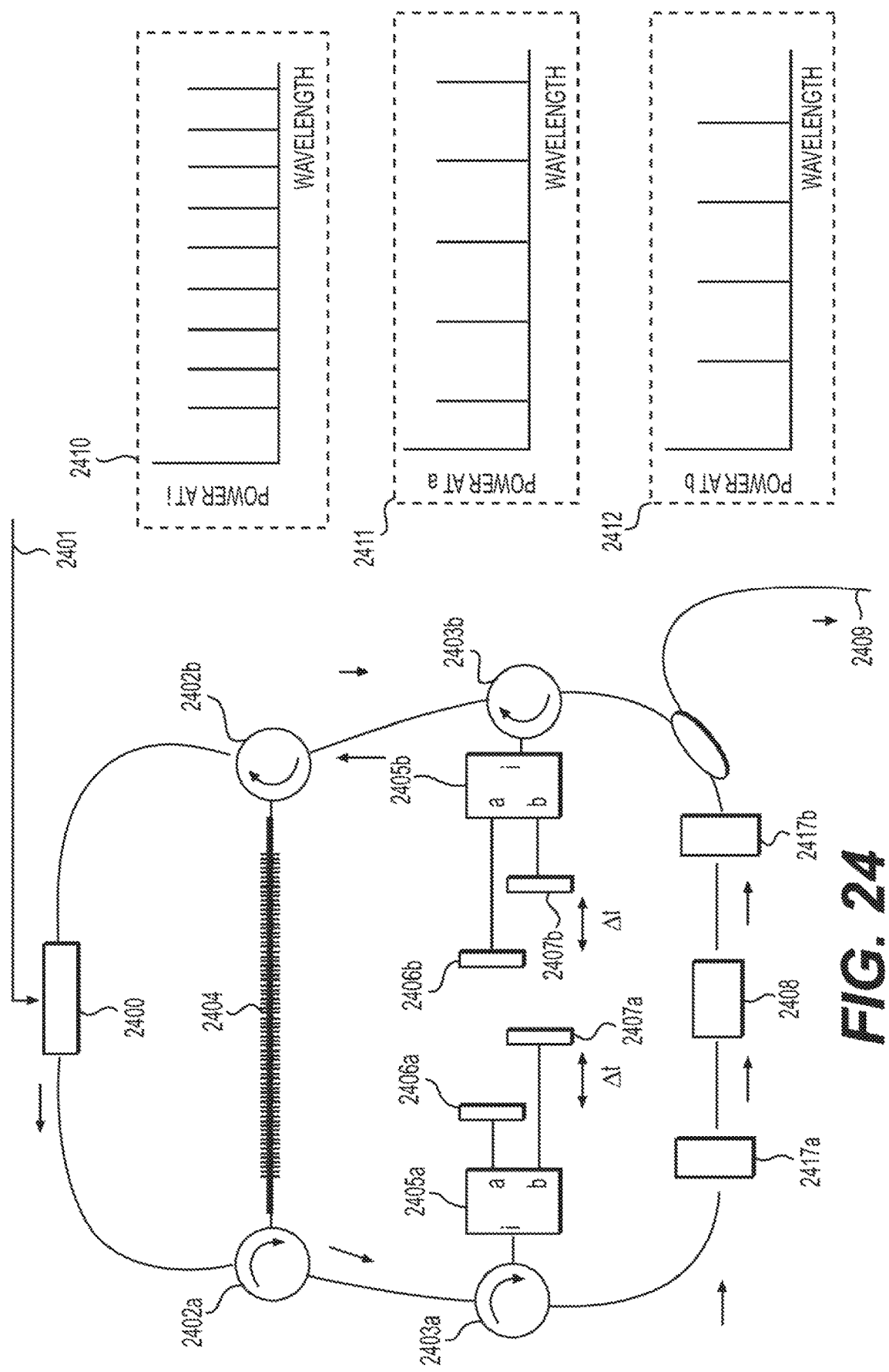
FIG. 24 is a diagram of an exemplary laser source that incorporates optical interleaves and deinterleavers to generate different group delay across wavelength channels (with exemplary power graphs) according to an exemplary embodiment of the present disclosure.

In a further exemplary embodiment, additional dispersion is generated using optical interleaver/de-interleavers. In particular, FIG. 24 illustrates a diagram of an exemplary laser source that incorporates optical interleaves and deinterleavers to generate different group delay across wavelength channels (with exemplary power graphs) according to an exemplary embodiment of the present disclosure. In particular, as shown in FIG. 24, an exemplary laser cavity can be provided comprising an intensity modulator 2400 driven by a drive signal 2401, circulators 2402a, 2402b, a dispersion element 2404, wavelength selective filters 2417a, 2417b, an optical amplifier 2408, and an output fiber 2409. The laser additionally includes circulators 2403a, 2403b and optical interleaves 2405a, 2405b. The interleaves 2403a, 2405b can separate even and odd channels input on i onto ports a (odd) and b (even). For example, if the filters 2417a, 2417b create a set of wavelengths ($\lambda 1, \lambda 2, \lambda 3, \ldots$), the odd wavelength set ($\lambda 1, \lambda 3, \lambda 5, \ldots$) can be transmitted on port a and the even wavelength set ($\lambda 2, \lambda 4, \lambda 5, \ldots$) on port b. In this exemplary way, the pulses at even wavelengths can be temporally separated from those of odd wavelengths by adjusting the length difference of the fiber-mirror path 2406a relative to port 2407a. This temporal displacement of even and odd wavelengths can be compensated for by interleaver 2405b by reversing the length difference in output ports 2406b, 2407b.

Figure 25:
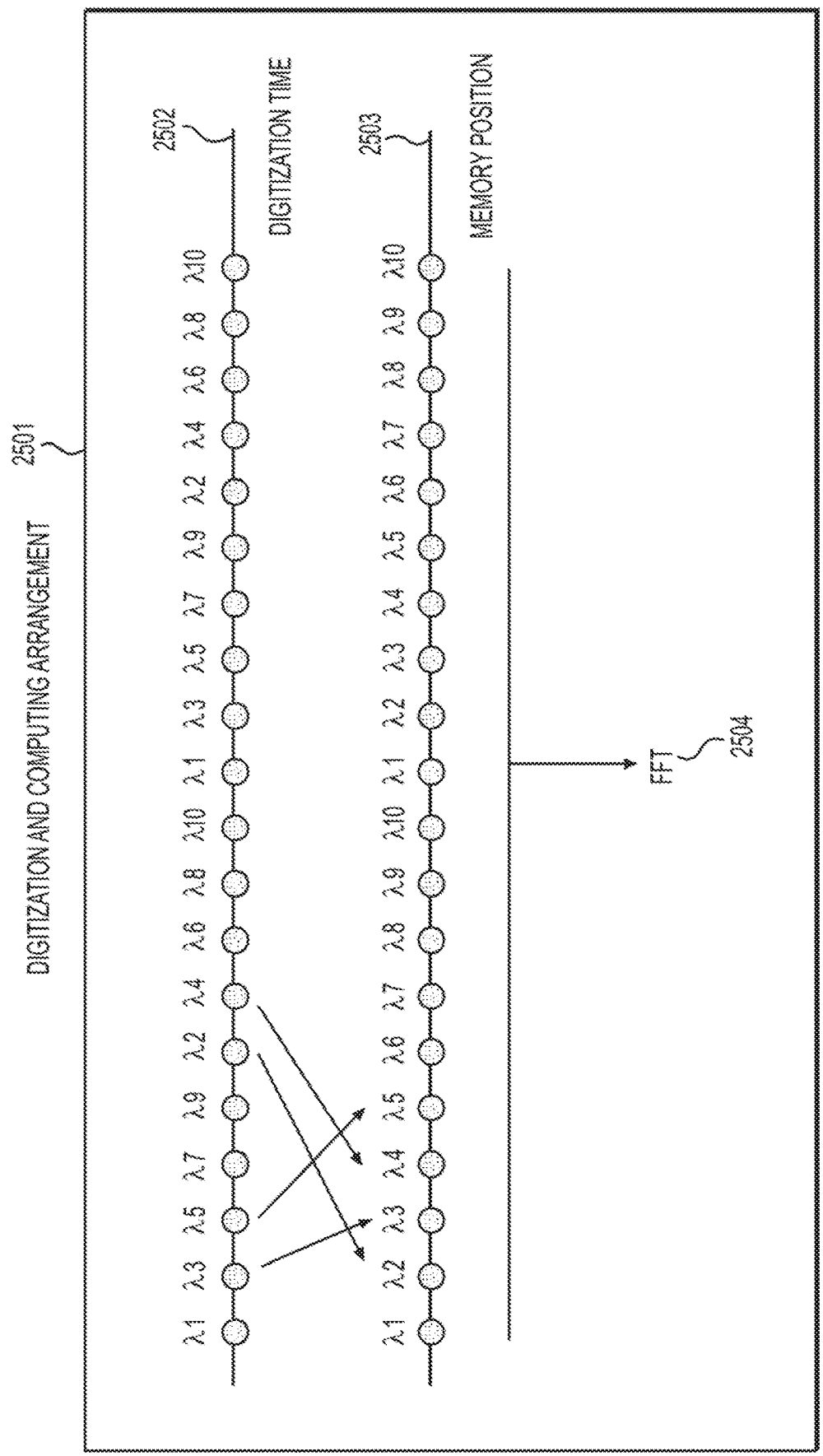
FIG. 25 is an illustration of an exemplary time-domain detection scheme of wavelength signals that are non-monotonic and their reorganization in a computing arrangement prior to Fast Fourier Transform (FFT) according to an exemplary embodiment of the present disclosure.

In this exemplary embodiment, the dispersion used by the element 2404 can be reduced to that sufficient to separate even wavelengths or odd wavelengths on their own, and the interleaves 2405a, 2405b can be used to displace the even/odd wavelength sets. The input power at the interlayer 2405a,b can be for example shown in 2410, and the output power on ports a is shown on 2411, while the output power on ports b is shown on 2412. The optical interleaved channel spacing can be designed to match that spacing of the laser that is set by the wavelength selective filter 2417a, 1417b. According to such exemplary configuration, the laser output does not proceed monotonically in wavelength and instead proceeds first through the odd wavelengths and then proceeds through the even wavelengths, for example, in the order: [λ1, λ3, λ5, λ7, λ9, λ2, λ4, λ6, λ8, λ10] for a ten-wavelength laser. An exemplary OS-OCT imaging system using such exemplary digitizer and computer arrangement 2501 can acquire these signals temporally 2502, and reorganize the measurements in memory 2503 prior to processing by, for example, Fourier transformation 2404, as illustrated in FIG. 25.

In a further exemplary embodiment, the source dispersion properties can be configured to generate an output pulse train that is substantially uniformly spaced in time by for example controlling the dispersion profile in the intracavity dispersion elements.

Figure 26:
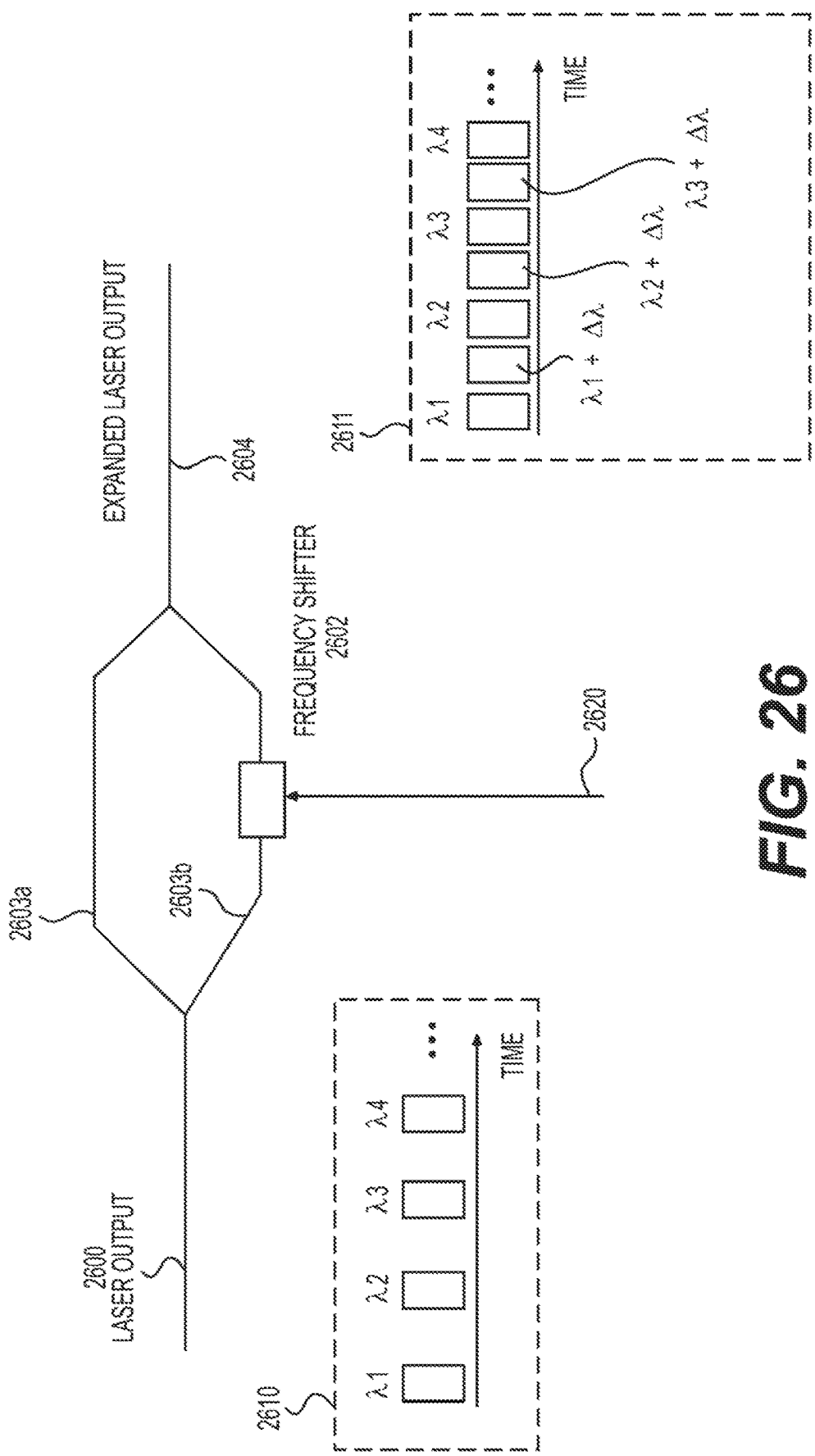
FIG. 26 is a diagram of an exemplary system to generate additional optical frequencies from an input set of frequencies using frequency shifting (and exemplary illustrations of wavelengths) according to an exemplary embodiment of the present disclosure.

FIG. 26 illustrates a diagram of an exemplary system to generate additional optical frequencies from an input set of frequencies using frequency shifting (and exemplary illustrations of wavelengths) according to an exemplary embodiment of the present disclosure. In this exemplary embodiment, the output pulse train of the laser 2600 at a first wavelength set 2610 (for example [λ1, λ2, λ3, λ4, . . . ]) can be divided into optical paths 2603a and 2603b, and one path can be passed through an optical frequency shifter 2602. The light/radiation from these paths can also be delayed by for example using fiber length and the two paths are recombined such that pulses do not overlap. The combined light/radiation 2604 can contain a new wavelength set 2611 including, for example, the set [λ1, λ1+Δλ, λ2, λ2+Δλ, λ3, λ3+Δλ, λ4, λ4+Δλ, . . . ]. This exemplary configuration can be used to expand the number of wavelengths provided by the source. The optical frequency shifter can be, for example, an acousto-optic frequency shifter and/or a phase modulator that can be driven with a periodic linear phase ramp that is aligned to the pulse arrival at the modulator. A drive signal 2620 can control the frequency shifter 2602, and can be connected, for example, to a computer arrangement that can additionally control the exemplary laser and imaging system.

In a further exemplary embodiment, the exemplary laser source can be configured to include the source polarization modulating between two state of polarizations (SOPs). For example, the output of the wavelength stepped laser can be split into two paths and the polarization is rotated in one path and the two beam are recombined to create a dual polarization-state source.

Figure 27:
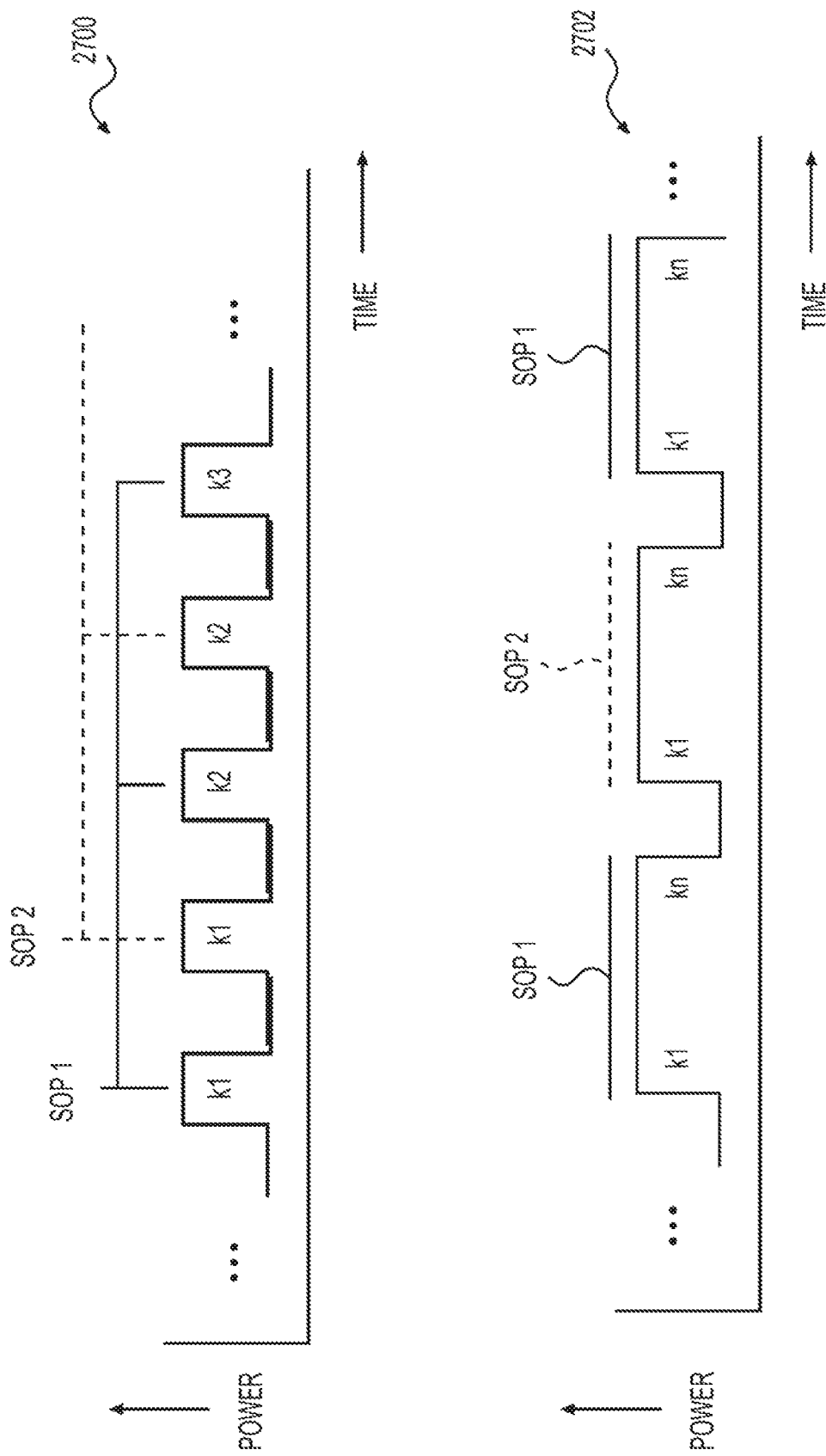
FIG. 27 is a set of graphs illustrating an exemplary polarization-modulated source output according to an exemplary embodiment of the present disclosure.

FIG. 27 shows a set of graphs illustrating an exemplary polarization-modulated source output according to an exemplary embodiment of the present disclosure. As shown in FIG. 27, the light/radiation in one path can be delayed relative to the light/radiation in the second path to avoid overlap, and such delay can be, for example, half the spacing between the input pulses to yield an output that cycles SOPs with every pulse 2700. In another exemplary configuration, the SOP modulation can be performed in adjacent A-lines 2702. In yet another exemplary configuration the SOP modulation can be performed between an arbitrary number of adjacent A-lines; for example, between the number of A-lines in a single B-scan frame or an entire C-scan. In a still another exemplary configuration, the laser output polarization can be actively modulated using, for example, an electro-optic modulator, a waveguide modulator and/or an acousto-optic frequency shifter arrangement.

Figure 28:
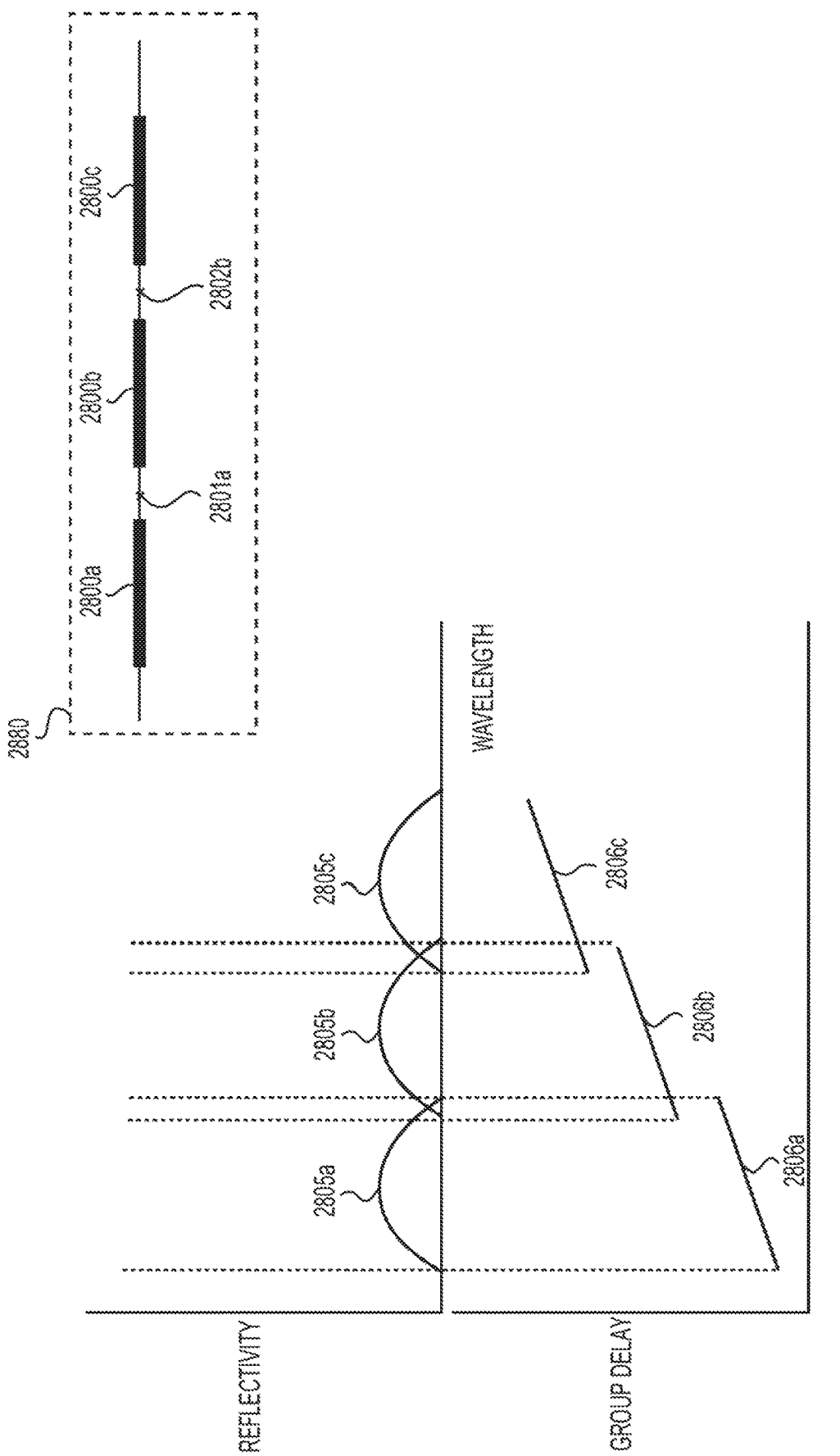
FIG. 28 is an exemplary illustration of a dispersive element provided by combining a set of continuously chirped fiber Bragg gratings according to an exemplary embodiment of the present disclosure.

FIG. 28 illustrates an exemplary illustration of a dispersive element provided by combining a set of continuously chirped fiber Bragg gratings according to an exemplary embodiment of the present disclosure. As shown in FIG. 28, an exemplary laser source can use a dispersive element constructed by concatenating a series of chirped FBGs 2880. For example, a first chirped FBG 2800a can be spliced into a spliced arrangement 2801a to a second chirped FBG 2800b, and can include a grating-free fiber between the chirped FBGs. A third chirped FBG 2800c can be spliced a spliced arrangement 2802b to the second grating 2800b. Each of the gratings 2800a-2800c can be configured to reflect a limited bandwidth. For example, the first grating 2800a can have a reflectivity profile 2805a, the second grating 2800b can have a reflectivity profile 2805b, and the third grating 2800c can have a reflectivity profile 2805c. The exemplary reflectivity profiles of the gratings 2800a-2800c can overlap. The group delay profiled by gratings 2800a-2800c can be given by the delay profiles 2806a-2806c respectively.

Figure 32:
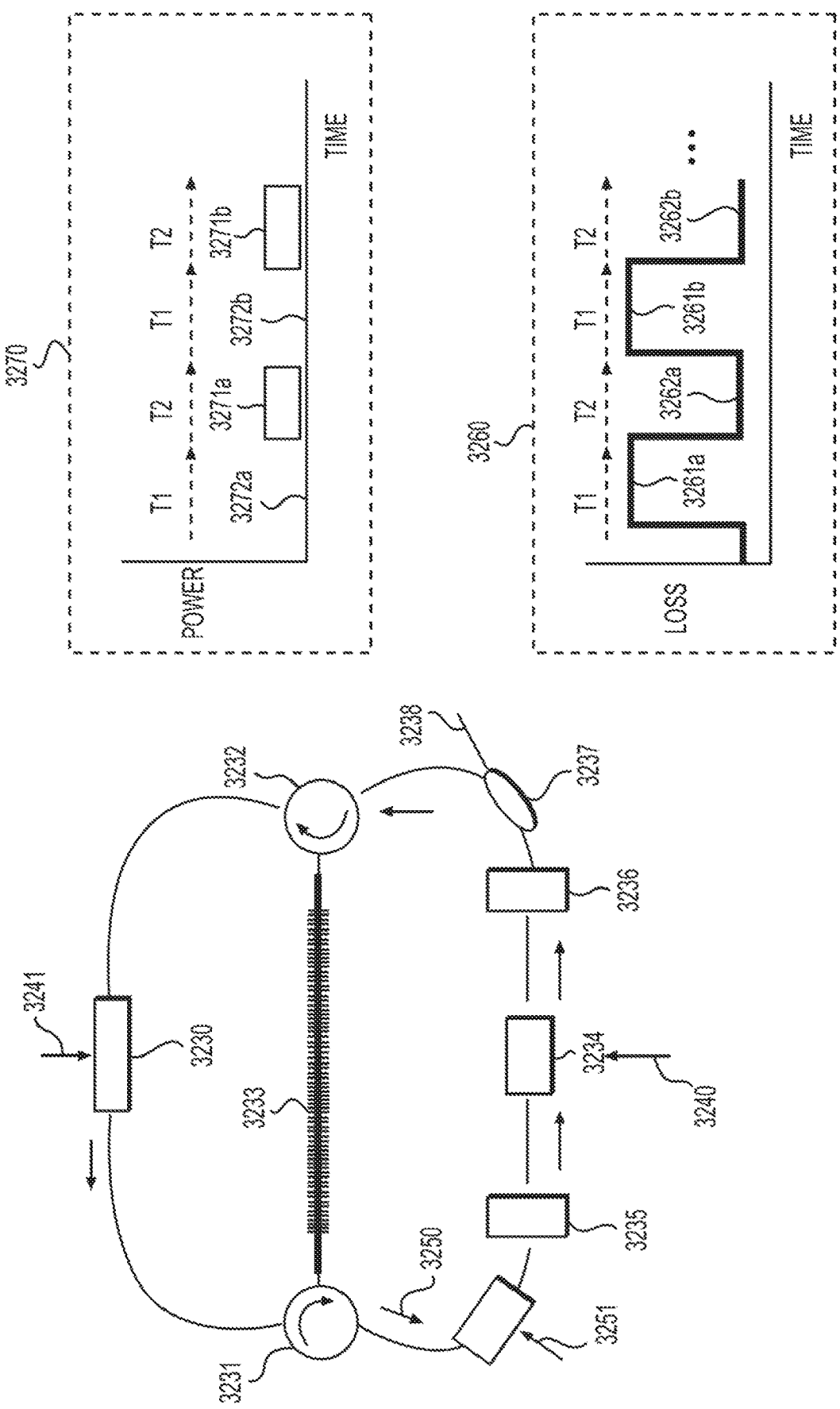
FIG. 32 is a diagram of an exemplary laser source providing modulation in the cavity that is configured to suppress light circulation in an specific path (and exemplary graphs providing outputs thereof) according to an exemplary embodiment of the present disclosure.

FIG. 32 shows a diagram of an exemplary laser source providing modulation in the cavity that is configured to suppress light circulation in an specific path (and exemplary graphs providing outputs thereof) according to an exemplary embodiment of the present disclosure, in which the exemplary laser can be configured to avoid the circulation of light in an unwanted path by use of a modulator. In particular, the exemplary laser can be configured to include a modulator 3230, circulators 3231, 3232, a reflective-dispersive arrangement 3233, an additional modulatable loss or gain element 3251, an optical set of wavelength selective filters 3235, 3236, an optical amplifier 3234, and an output coupler 3237 creating optical output 3238. For example, the exemplary laser can be configured to preferentially lase in the cavity path A defined by light passing through components in the order: 3230-3231-3233-3231-3250-3235-3234-3236-3237-3232-3233-3230, and is further configured to not lase in the cavity path B defined by light passing through components in the order: 3234-3236-3237-3232-3233-3231-3250-3235-3234.

The exemplary system shown in FIG. 32 can be configured to provide lower gain in cavity path B by for example modulating the loss in this path using, for example, a modulator 3250, or by modulating the gain of the optical amplifier 3234 using drive signal 3240. The modulation of this loss/gain can be periodic in a graph 3260 with a timing frequency (T1+T2). The circulation of the light through path B can be configured to be (N+0.5)*(T1+T2), where N is an integer. As indicated in the graph 3260, the light/radiation circulating in path B can successively encounter times with low loss (or high gain) 3262a, 3262b, followed by times with high loss (or low gain) 3261a, 3261b. This can increase the overall loss of the path across multiple circulations and reduce the build-up of light. The circulation time of path A can be set separately from that of path B by for example adding fiber to the modulator 3230. This exemplary timing can be configured to be N*(T1+T2) where N is an integer. For example, light/radiation circulating in path B can provide a consistent state of low loss (or high gain) that produces lasing, or can experience a state of high loss (or low gain) with a suppress lasing. The drive signal 3241 to the modulator can be configured to provide a laser duty cycle of 50% or less than 50% and aligned to the timing of the low loss (or high gain) cycle. In this exemplary manner, the exemplary laser can be configured to output light/radiation 3238 with periods of lasing output (3271a, 3271b) separated by periods of limited light/radiation output (3272a, 3272b) as shown in a graph 3270.

In this exemplary configuration, light/radiation from path B can be suppressed. The time T2 can for example be equal to T1, or can be smaller than T1. In can be understood that the modulation pattern in 3260 can for example be a smoothed modulation such as a sinusoidal modulation. The dispersive element 3233 can be configured to produce wavelengths at the gain peak during the times when cavity path A has the lowest overall gain such as at the edges of the time windows 3262*a*, 3262*b*, and produces wavelengths at the edges of the gain peak during times when the gain is highest, such as in the central region of the time windows 3262*a*, 3262*b*. The modulation of loss and gain can be performed for example by modulating the current 3240 used in a semiconductor optical amplifier 3234, and/or by insertion of an additional modulator or gain element 3250 controlled by signal 3251. For example, the control signals 3240 and 3251 can be for example synchronized with the drive signal 3241. The duty cycle of the output light 3238 can be increased by splitting the light into two paths and delaying one path relative to the other by approximately the length of one A-line and recombining. In this second path, the light/radiation can, for example, polarization rotated to create adjacent A-lines with different polarizations, as shown in FIG. 27.

Figure 36:
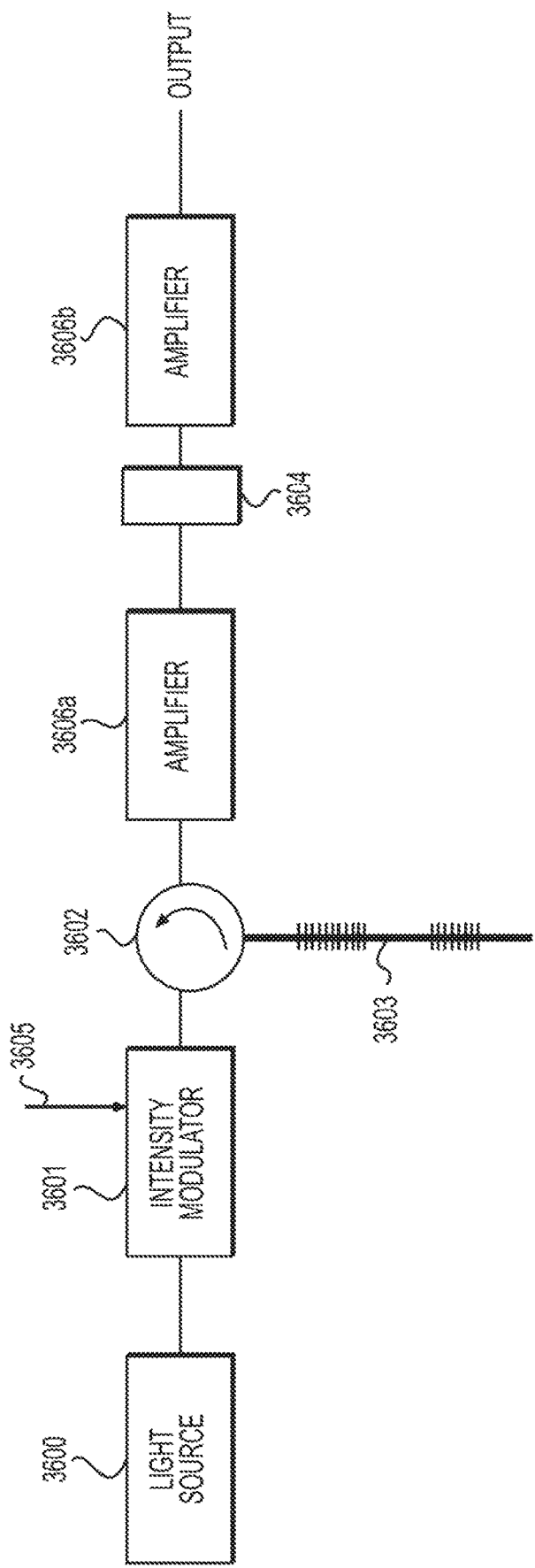
FIG. 36 is a diagram of an exemplary OS-OCT source provided by dispersing a pulsed broadband laser source according to an exemplary embodiment of the present disclosure.

FIG. 36 shows a diagram of an exemplary OS-OCT source provided by dispersing a pulsed broadband laser source according to an exemplary embodiment of the present disclosure. In addition to a laser cavity, the exemplary source can have a non-cavity configuration. In this exemplary embodiment, the light/radiation from a broadband light source 3600 can be pulsed in time by an intensity modulator 3601 (e.g., driven by a signal 3605 from a computing arrangement or a pulse generator). The light/radiation can enter a circulator 3602 which directs such light/radiation toward a dispersion element 3603, such as a FBG array or a continuously chirped FBG. The dispersed light/radiation returns from the dispersion element 3603, and travels through a wavelength selective filter 3604 (e.g., the number of filters in this path range from zero to multiple). Light/radiation can be amplified at several stages by optical amplifiers 3606*a*, 3606*b*. The output of the exemplary laser can be wavelength-stepped if a wavelength selective comb filter 3604 is used, or if a FBG array is used as the dispersion element 3603. If a continuously chirped FBG 3603 is used without a wavelength selective filter 3604, the output of the laser can be wavelength-swept. These exemplary components can be arranged in different orders to achieve the same output.

Additional Interferometer Embodiments

Figure 29:
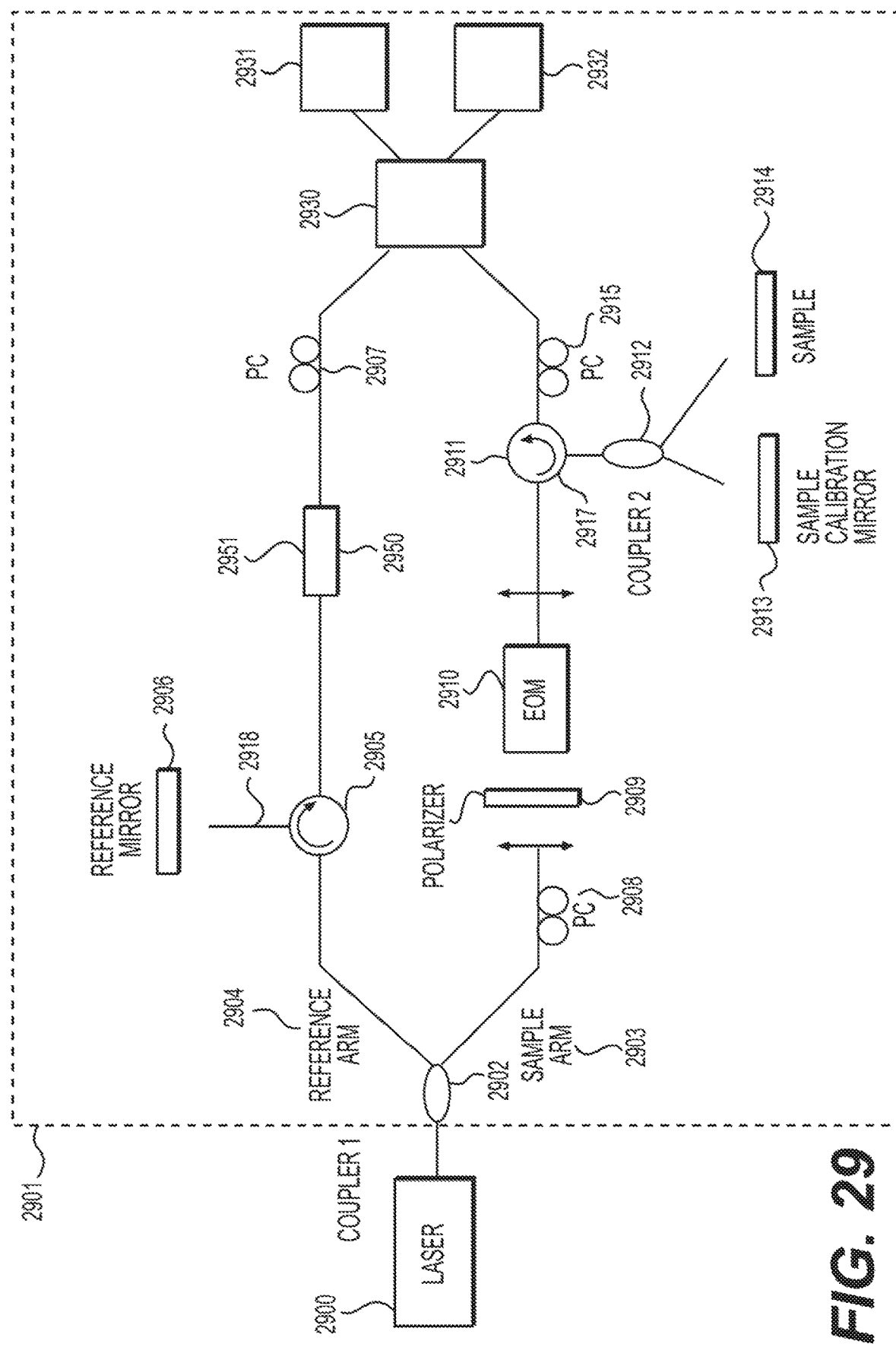
FIG. 29 is a diagram of an exemplary imaging interferometer that uses phase modulation to perform quadrature demodulation according to an exemplary embodiment of the present disclosure.

FIG. 29 illustrates a diagram of an exemplary imaging interferometer that uses phase modulation to perform quadrature demodulation according to an exemplary embodiment of the present disclosure. In this exemplary embodiment, the exemplary OS-OCT system can be configured to perform complex demodulation of fringes by phase modulating the light in the reference arm or sample arm. As shown in FIG. 29, a laser source 2900 can transmit light/radiation to an interferometer 2901 which comprises a sample arm 2903 and a reference arm 2904 created by an optical coupler 2902. The light/radiation in the reference arm 2904 can passes through a phase modulator 2950 that can be driven by a signal 2951 generated synchronously with the laser 2900 by a computer arrangement. This phase modulator 2950 can be constructed using an electro-optic modulator, an acousto-optic frequency shifter, and/or other arrangement for modulating the phase of the beam. The light/radiations from the reference and sample arms 2903, 2904 can be combined at an interfering coupler 2930, and the output signals can be detected by digitizer and computer arrangements 2931 and 2932. The reference arm phase shift can be configured to facilitate a detection of the in-phase (I) and quadrature (Q) components of the interference fringes, and to allow complex conjugate ambiguity removal. The reference can contain a circulator 2905 that directs and receives light from a reference mirror 2906 through an optical fiber path 2918. The sample arm 2903 can include an electrooptic modulator 2910 to control the light polarization and a polarizer 2909. A circulator 2911 can direct light/radiation to a sample calibration mirror 2913 and a sample 2914 through an optical coupler 2912, and receive reflected light/radiation from these paths along an optical fiber 2917. Polarization controllers 2907, 2915, 2908 can be provided to control polarization states of light/radiation.

Figure 30:
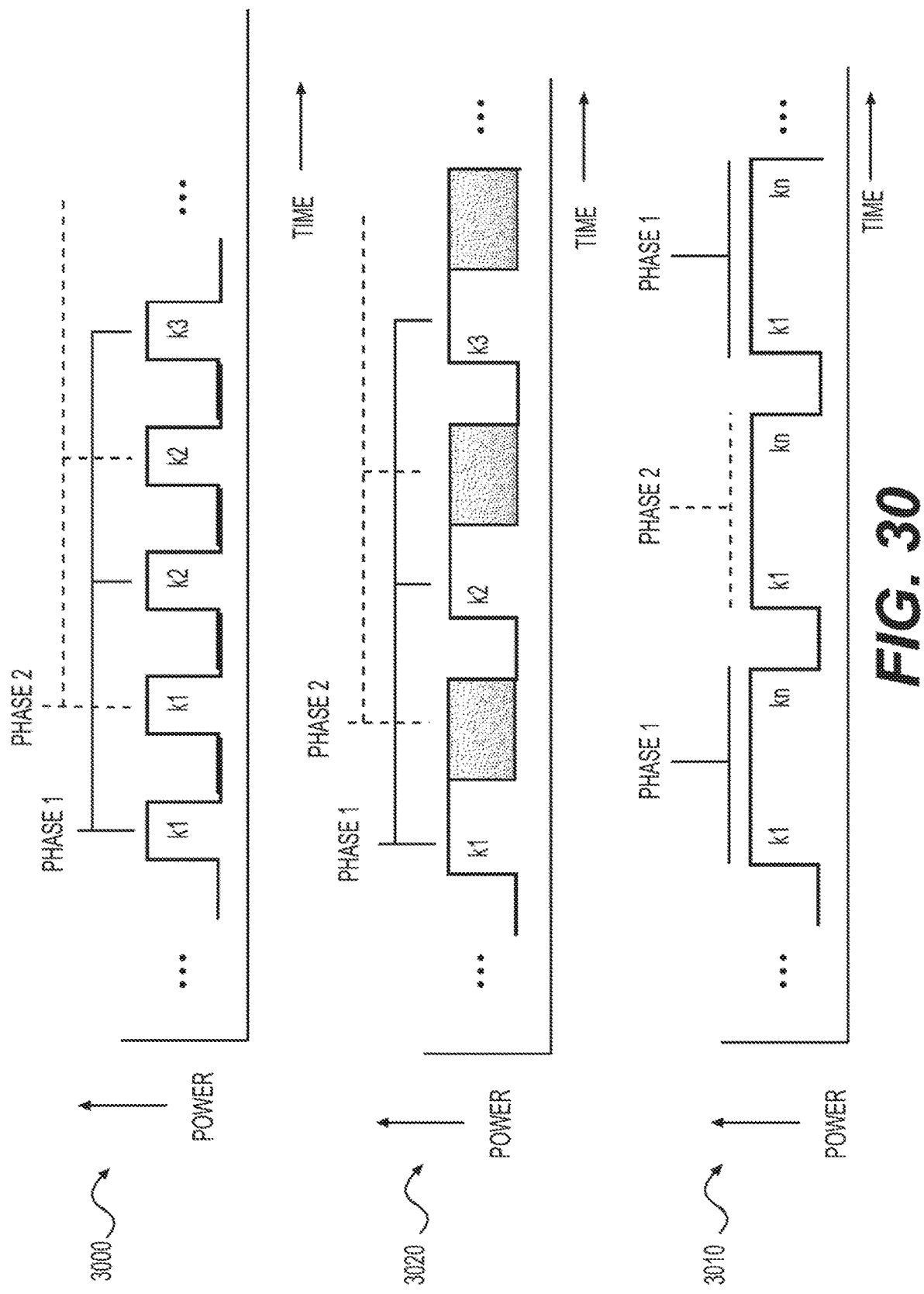
FIG. 30 is a set of exemplary graphs providing exemplary schemes for phase shifting light as a function of time and wavenumber to perform quadrature demodulation according to an exemplary embodiment of the present disclosure.

The phase shifting that can be performed by the modulator 2950 can be configured to phase shift adjacent optical pulses from the exemplary source, as shown in a graph 3000 of FIG. 30, for example applying phase 1 to a first pulse at wavenumber k1 and a second phase 2 for a second pulse at wavenumber k1, and repeating this for subsequent pulses. Alternatively or additionally, the phase state can be modulated between A-lines (3010). Alternatively, the phase modulator can operate within a pulse to generate one phase shift at the front of the pulse and a second phase shift on the later half (3020). While a two-state phases shifting device is described that nominally provide 0 degree and 90 degree phase states, multiple phase states can be generated by a phase modulator such that, for example, a three-state configuration is used providing phases of 0 deg, +60 deg, and +120 deg. Alternatively or in addition, quadrature or phase shifted signals for complex conjugate removal can be created using established techniques based on acousto-optic frequency shifters or N×N interfering couplers (where, e.g., N is not equal to 2).

Figure 33:
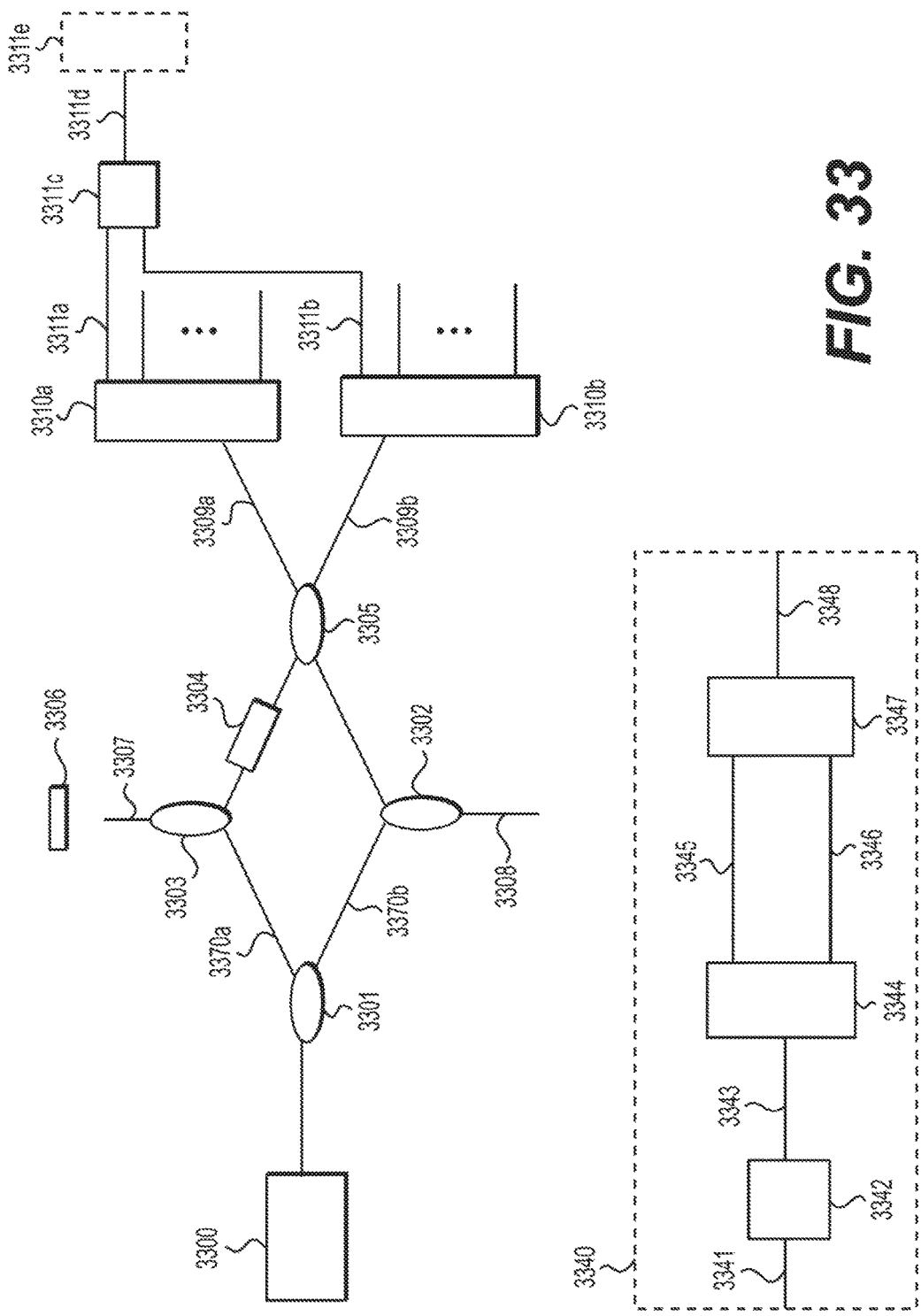
FIG. 33 is a diagram of an exemplary OS-OCT system that uses a comb source comprising multiple wavelengths and a wavelength demultiplexer to spatially separate each wavelength signal prior to detection according to an exemplary embodiment of the present disclosure.

FIG. 33 shows a diagram of an exemplary OS-OCT system that uses a comb source comprising multiple wavelengths and a wavelength demultiplexer to spatially separate each wavelength signal prior to detection according to another exemplary embodiment of the present disclosure. As shown in FIG. 33, a comb source 3300 can be used that can provide continuous or nearly continuous light/radiation output at a set of wavelengths λ1 through λn. Such exemplary source 3300 can be input into an interferometer comprising a splitting coupler 3301 that separates light/radiation into a reference arm 3370*a* and a sample arm 3370*b*. The reference arm 3370*b* can use a coupler 3303 to direct light to a fiber 3307 that can be couple to a mirror 3306. Reflected light/radiation returns to the coupler 3303, and can be transmitted to a phase modulator or an acousto-optic frequency shifter 3304. Sample arm light/radiation can be directed to a coupler 3302 that further directs light/radiation to a fiber 3308 that forwards the light/radiation to the sample, and reflected light/radiation can be returned to an interfering coupler 3305. Interference fringes appear on output ports 3309*a* and 3309*b*. The interference fringes at wavelength λ1 can be isolated using a demultiplexer 3310*a* and 3310*b* which can be or include, for example, a grating or an arrayed waveguide grating (AWG). The optical signal at λ1 can be directed to an output 3311*a*. A similar output for demultiplexer 3310*b* can be directed to output 3311*b* and the signals 3311*a*, 3311*b* can be input to a balanced photoreceiver to perform intensity noise subtraction.

The detected signal 3311*d* can then be transmitted or otherwise provided to a computing arrangement 3311*e* shown in detail as a computer arrangement 3340. For example, the signal 3341 can be digitized by an analog-to-digital converter 3342 provided in the computer arrangement 3340, and such signal information 3343 can be separated into the I 3345 and Q 3346 components using, for example, a demodulator 3344. Such exemplary demodulator 3344 can be or include an I/Q demodulator based on frequency mixing using known techniques when the device 3304 is, e.g., a frequency shifter, such as an acousto-optic frequency shifter. The signals 3345, 3346 can define the complex interference signal at λ1, and can be one portion of an input into a Fourier transform engine 3347 that can be used (along with information from other wavelengths) to calculate or otherwise determine the depth-resolved scattering signal 3348 using known Fourier-domain OCT processing. The additional wavelength signals cam be analyzed in a similar manner using the additional output ports of the demultiplexers 3310a, 3310b using a similar exemplary embodiment of the system and method that is described herein for λ1.

Optical Receiver, Digitizer, and Computer Embodiments

Figure 31:
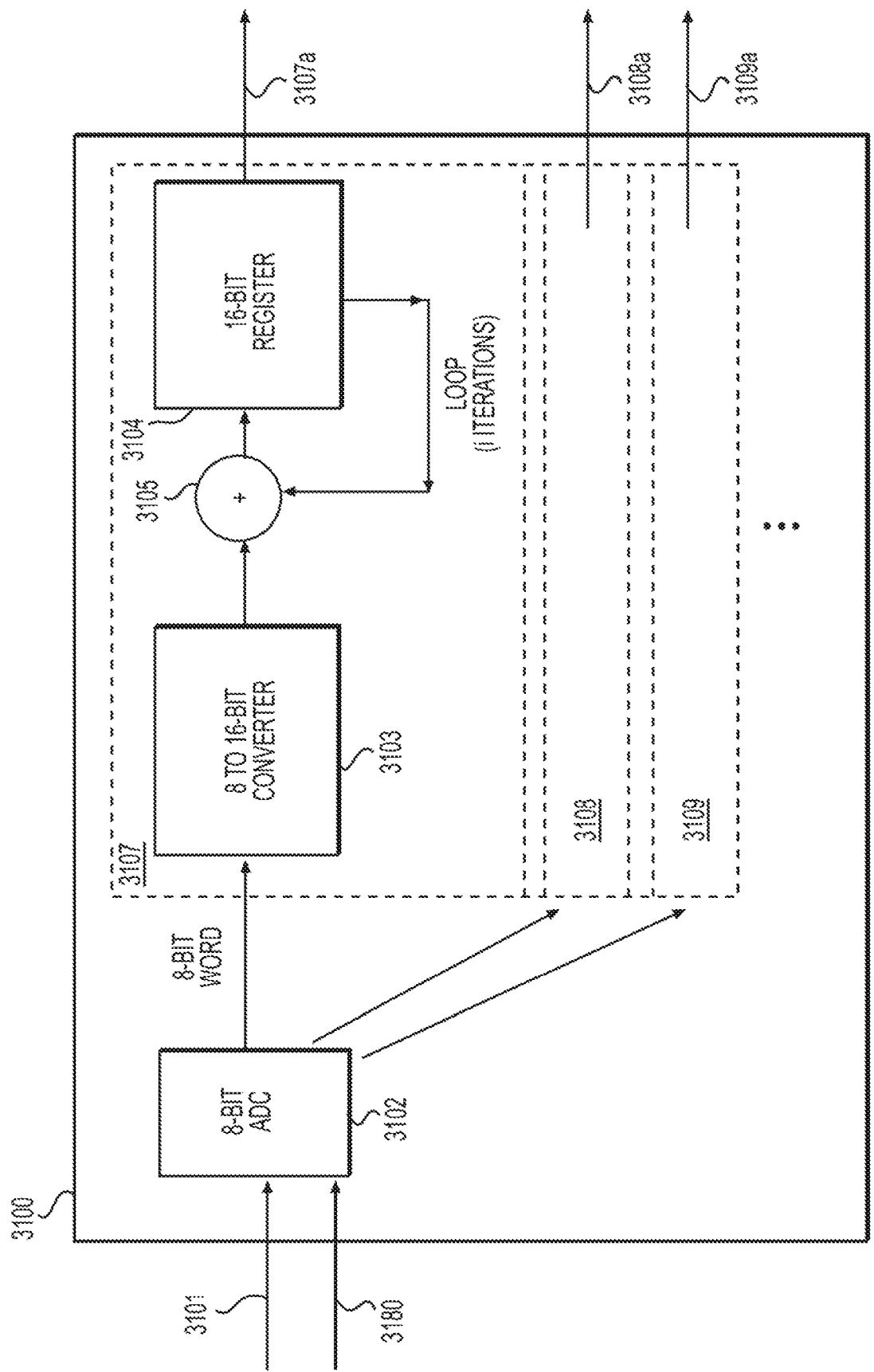
FIG. 31 is a diagram of an exemplary system and an exemplary acquisition of signals using 8-bit digitizers and fringe averaging to a register with a larger big depth according to an exemplary embodiment of the present disclosure.

FIG. 31 shows a diagram of an exemplary system and an exemplary acquisition of signals using 8-bit digitizers and fringe averaging to a register with a larger big depth according to an exemplary embodiment of the present disclosure. For example, the OS-OCT system can include a digitizer 3100 for acquiring interferometric fringe signals that can be configured to perform on-board averaging of fringes. As shown in FIG. 31, the digitizer 3100 can digitize the analog signal 3101 using an 8-bit analog to digital converter 3102. The 8-bit digital word from sample 1 can then be passed to an averaging engine 3107 that can first convert the word to 16-bits 3103, and then add this word 3105 with an existing value in a register 3104. Such exemplary procedure can be repeated for sample 2 in a separate averaging engine 3108.

In one exemplary configuration for N points in a A-line/fringe, there can be N averaging engines. The N+1 sample can then be returned to the first averaging engine 3107. Such exemplary procedure can be repeated for i iterations, and the value after i iterations can be output 3107a from the averaging engine 3107 as a 16-bit word. The set of 16-bit words 3107a, 3108a, 3109a, etc. can define an averaged fringe, where 3108a can be generated by an averaging engine 3108 and 3109a is generated by an averaging engine 3109. Here we note that the digitizer 3102 can be operated at a higher bit-depth. This digitizer arrangement 3100 allows a lower-bit depth digitizer to be used while improving dynamic range and signal fidelity through fringe averaging. This exemplary digitizer system can be performed in part on a computer or a field programmable gate array. For example, the digitizer clock input 3180 can be synchronized to the laser such that the digitizer clock, laser A-lines, and resulting fringes remain highly synchronized. This on-board processor can also perform core signal processing such as the FFT. This can facilitate the optically subsampled system to perform real-time processing and image display. Additionally, the digitizer can be configured to continuously stream the acquired data to a computing arrangement allowing for continuous imaging or real-time continuous imaging. The signal can be digitized at a bit depth other than 8 bit such as 10 bits and can be converted to another bit depth than 16 bit such as 12 or 14 bit.

In another exemplary embodiment of the present disclosure, the digitizer can utilize a sample, and hold or an integrate and hold functionality that accumulates the signal across the pulse duration and return the accumulated measurement, as an alternative to conventional digitizers used with low-pass filters. In another exemplary embodiment, the signal roll-off that occurs as frequencies near the Nyquist edge of the subsampled baseband image can be offset by amplifying the signals as a function of depth, and selecting such amplification to match the roll-off of the OS-OCT system.

Alternative Embodiments of Imaging Probes

In a further exemplary embodiment of the present disclosure, the optically subsampled imaging system can be operated with a small scanned beam probe that can be used to image internal sites. This exemplary scanning probe can be based on a fiber-scanning architecture, on a small MEMs based mirror, on a rotating prism or rotating probe design. In addition, this probe can be configured to provide forward and side imaging. For example, the microscope can be configured to include optical elements needed to dynamically adjust the focal plane to the sample position. This can be performed by, e.g., mechanically moving lens positions, and/or by using a variable optical lens such as a voltage controlled liquid lens technology. In addition or alternatively, such exemplary probe or microscope system can include non-Gaussian imaging beam profiles that feature extended depths of focus. Such exemplary beam profile can be, e.g., a Bessel beam that can be generated for example by using a donut aperture or by an axicon lens.

Exemplary Embodiments of Design and Demonstration of Further Light Source

Figure 37:
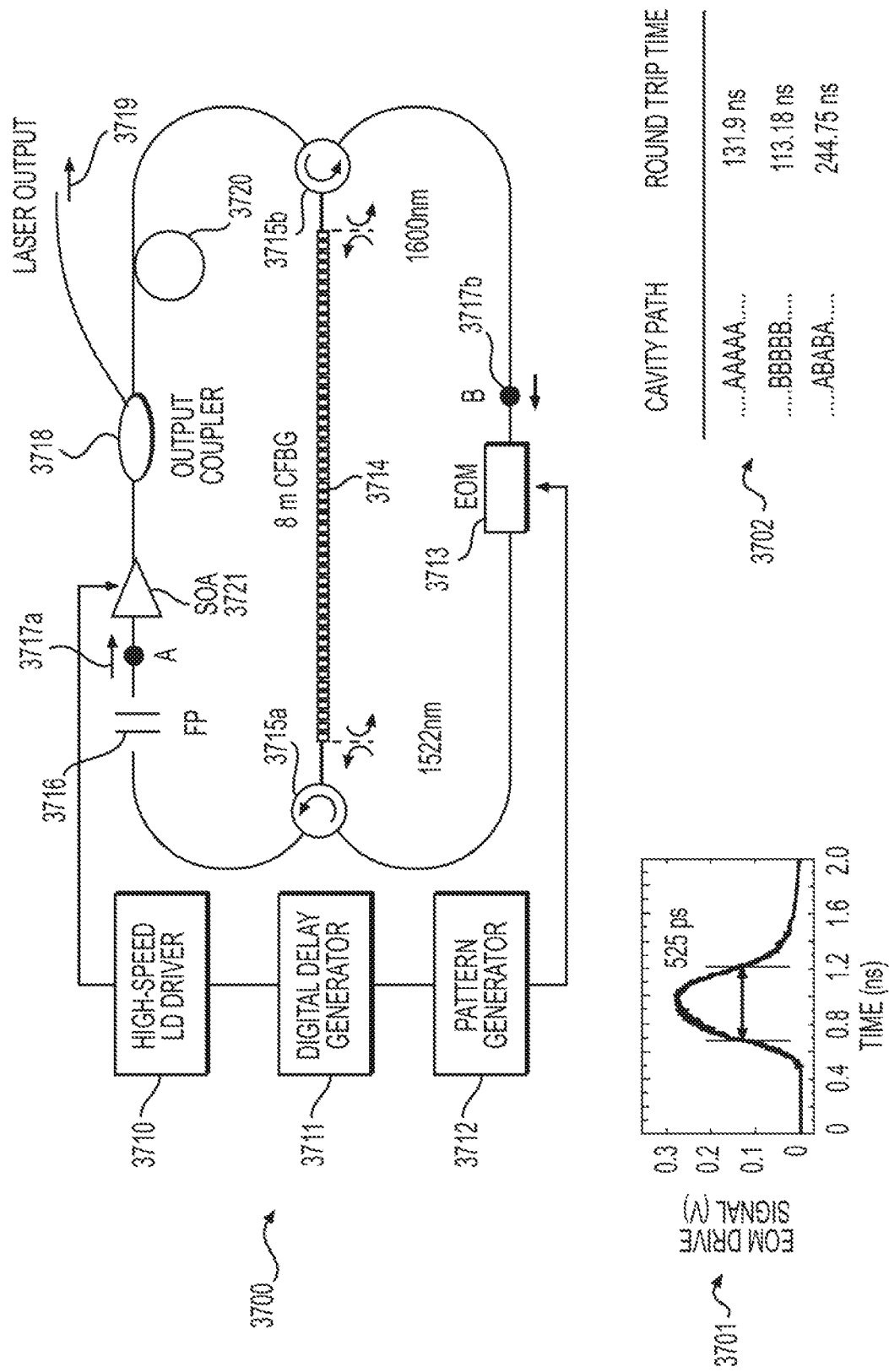
FIG. 37 is a set of exemplary illustrations of an exemplary configuration, operation/functionality, and timing of an exemplary OS-OCT source according to an exemplary embodiment of the present disclosure.
Figure 37:
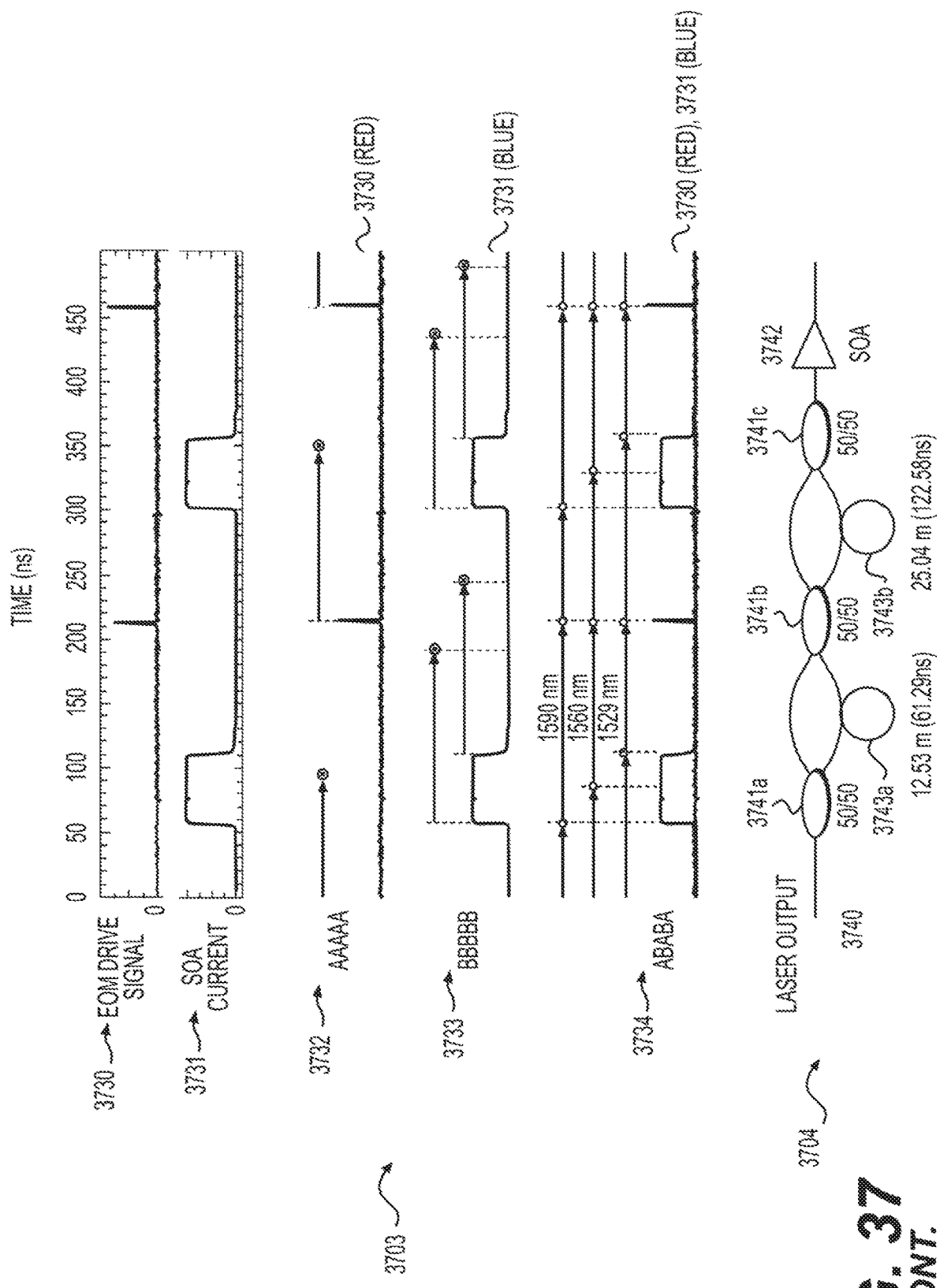

FIG. 37 illustrates a set of exemplary illustrations of an exemplary configuration, operation/functionality, and timing of an exemplary OS-OCT source 3700 according to an exemplary embodiment of the present disclosure. For example, an approximately 525 ps electric pulse 3701 from a pattern generator 3712 can drive an electro-optic lithium niobate intensity modulator 3713, and repeated at a resonance of the cavity round trip time. The gain medium can be or include a semiconductor optical amplifier (SOA) 3721 with 3-dB bandwidth of 102 nm. The continuously chirped fiber Bragg grating 3714 can be placed between two circulators 3715a, 3715b to facilitate access to both positive and negative dispersion. The grating can be, e.g., 8.3 m in length with a continuous reflection bandwidth from 1522 nm to 1605 nm. The grating can be designed to produce a linear group delay with respect to optical frequency, e.g., yielding a dispersion at 1550 nm of +/−930 ps/nm. The same grating can be used for both positive and negative dispersion. The insertion loss of the grating used in reflection mode was 1.36 dB for the near-side reflected wavelength and 1.71 dB for the wavelength that reflects from the far end of the grating. In order to have higher stability and lower level of noise, the chromatic dispersion in the laser cavity induced by single mode fibers can be matched by inserting a 9 m dispersion compensating fiber (DCF) 3720 with a dispersion parameter of −38.5 ps/nm/km at λ=1550 nm. Further, 20% of the light in the laser cavity can be tapped out via an 80/20 output optical coupler 3718 to generate an optical output 3719. A digital delay generator 3711 can be used to modulate an SOA current drive 3710. The delay generator can be driven by the pattern generator 3712.

Because the fiber Bragg grating can be partially transmitting, there can be three separate cavities in the laser. These cavities can be labeled by order in which the circulating light passes through points A 3717a and B 3717b. The longest cavity that provides the desired lasing can pass through both points (cavity ABABA). Two short cavities are also created by the non-zero transmission of the CFBG (cavity AAAAA, cavity BBBBB). Within the CFBG pass band, approximately 30% of the light can be reflected. In addition, wavelengths outside the grating reflection bandwidth are transmitted through the grating with nearly 100% efficiency. Because cavity BBBBB has no optical gain, it is likely not a lasing cavity but can create reflections. Cavity AAAAA can contain the SOA, and can lase which can impact the lasing in cavity ABABA.

Lasing in cavity AAAAA can be suppressed by modulating the SOA and controlling the round trip time of each of the cavities ABABA, AAAAA, and BBBBB. In this exemplary configuration, the round rip time of cavity ABABA can be approximately twice that of cavity AAAAA and cavity BBBBB (see 3702). The exemplary modulation of the SOA 3731 and EOM 3730 can be a suppressed light circulation in these short cavities as shown in graphs 3703. Light/radiation circulating in cavity AAAAA can be blocked by the EOM 3732. Light/radiation circulating in cavity BBBBB can be blocked a all wavelengths of the CFBG by the SOA modulation 3733. Light/radiation circulating in the cavity ABABA can pass through the EOM to the SOA while current is high and then returns to pass through the EOM 3734.

To generate a wavelength-stepped (frequency comb) output, a fixed fused silica FP etalon 3716 with 80 GHz FSR (~0.64 nm) and low finesse (~5) can be provided. In one exemplary embodiment, etalons with a FSR between 25 GHz and 400 GHz can be used. When this FP is removed, a continuous wavelength swept operation can be achieved. In the exemplary embodiment of the system 3700, the SOA can be driven with, e.g., a 61 ns current pulse. The round trip of the of the long cavity (ABABA) was 244.75 ns (approximately 50.1 m), e.g., almost 4 times larger than the SOA current pulse. This can produce an approximately 25% duty cycle at the laser output. To increase the A-line rate, a 4× copy-and-paste buffering delay line 3704 can be used to create a 16.3 MHz A-line rate. A booster SOA 3742 was used after the copy-and-paste delay line. The delay line comprised a set of 50/50 couplers (3741*a*,3741*b*,3741*c*) and delay fibers (3743*a*,3743*b*). Polarization controllers were included in the paths to align polarization state to the booster SOA 3742.

In this exemplary embodiment, FP etalons with finesse values between 3 and 25 were used to provide low noise operation. In this laser embodiment, a FP etalon with a line width that is broader than the desired lasing line width was used. Lasing provides line width narrowing while the broader FP pass band can yield lower noise performance. For example, the FP can be a solid etalon, or can be constructed from two partial mirrors with an air space between the mirrors. Using air-spaced mirrors can facilitate the FSR of the etalon to be changed dynamically.

It should be understood by those skilled in the art that the output coupler in the laser designs (for example output coupler 3718 shown in FIG. 37) can be located anywhere within the laser cavity to provide laser output light. In further exemplary embodiments, the optical frequency comb source can provide light/radiation at discrete optical frequencies spaced by more than 20 GHz and an instantaneous line width of less than 10 GHz for each optical frequency.

Figure 38:
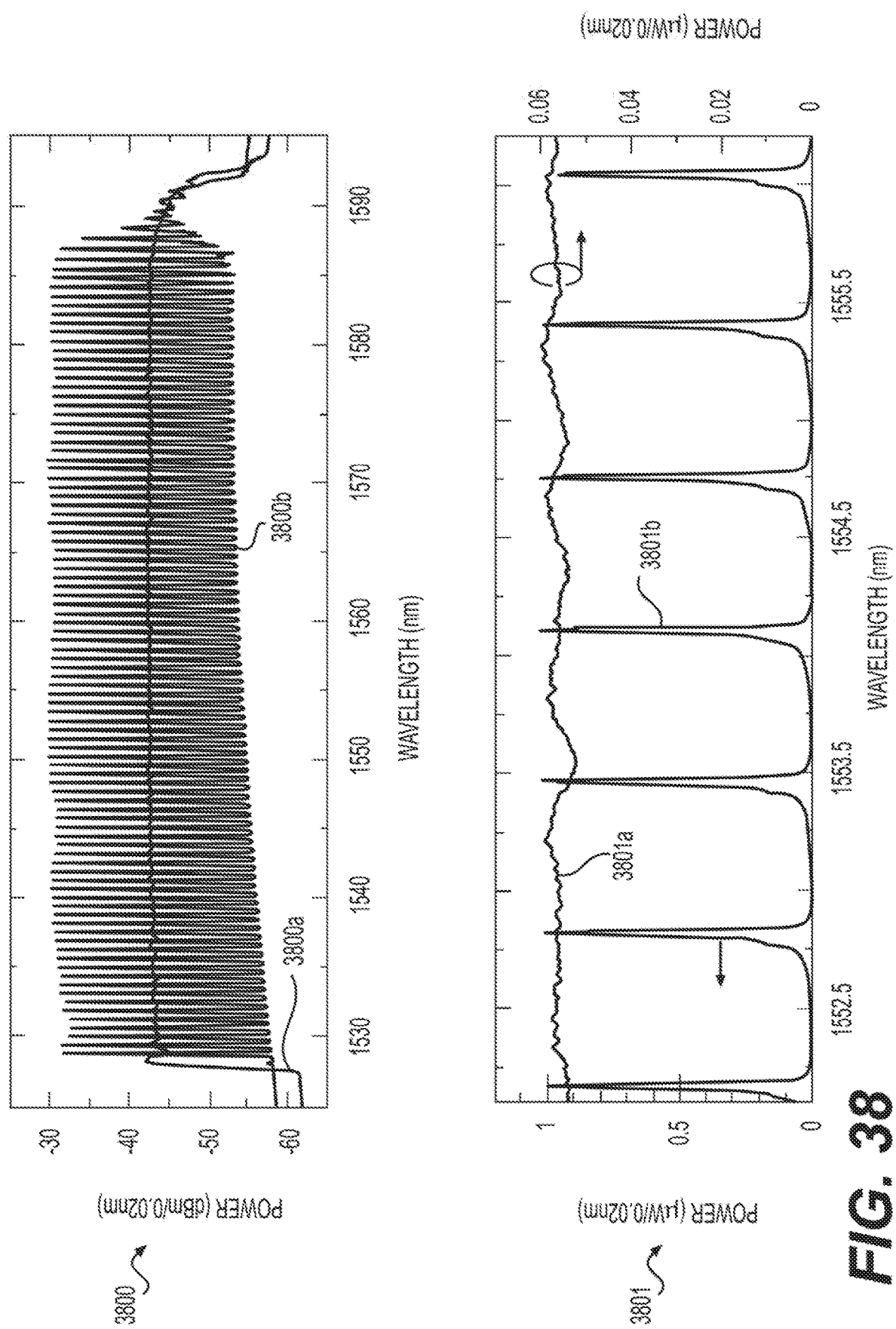
FIG. 38 is a set of graphs providing an exemplary measurement of the spectral output of the exemplary OS-OCT source according to an exemplary embodiment of the present disclosure.

FIG. 38 shows a set of graphs providing an exemplary measurement of the spectral output of the exemplary OS-OCT source according to an exemplary embodiment of the present disclosure. For example, output spectrum 3800, 3801 of the laser after the 4× copy-and-paste delay line 3704 (of FIG. 37) illustrated in FIG. 38 for continuous (3800*a*, 3801*a*) and frequency comb (3800*b*, 3801*b*) configurations. In each such exemplary configuration, the SOA drive current pulse of 61 ns set the lasing bandwidth to ~62 nm (1525-1587). In the exemplary frequency comb configuration, output lines spaced by 80 GHz are observed with FWHM line width below the 0.02 nm resolution of the optical spectrum analyzer. The output power of the laser before 4× copy-and-paste buffering was 1.7 mW and 1.5 mW for the continuously swept and frequency comb configurations, respectively. These power measurements are low in part due to the 25% duty cycle of the output. After copy-and-paste buffering and booster amplification, the output power was measured to be 35 mW for both continuous and frequency comb configurations.

Figure 39:
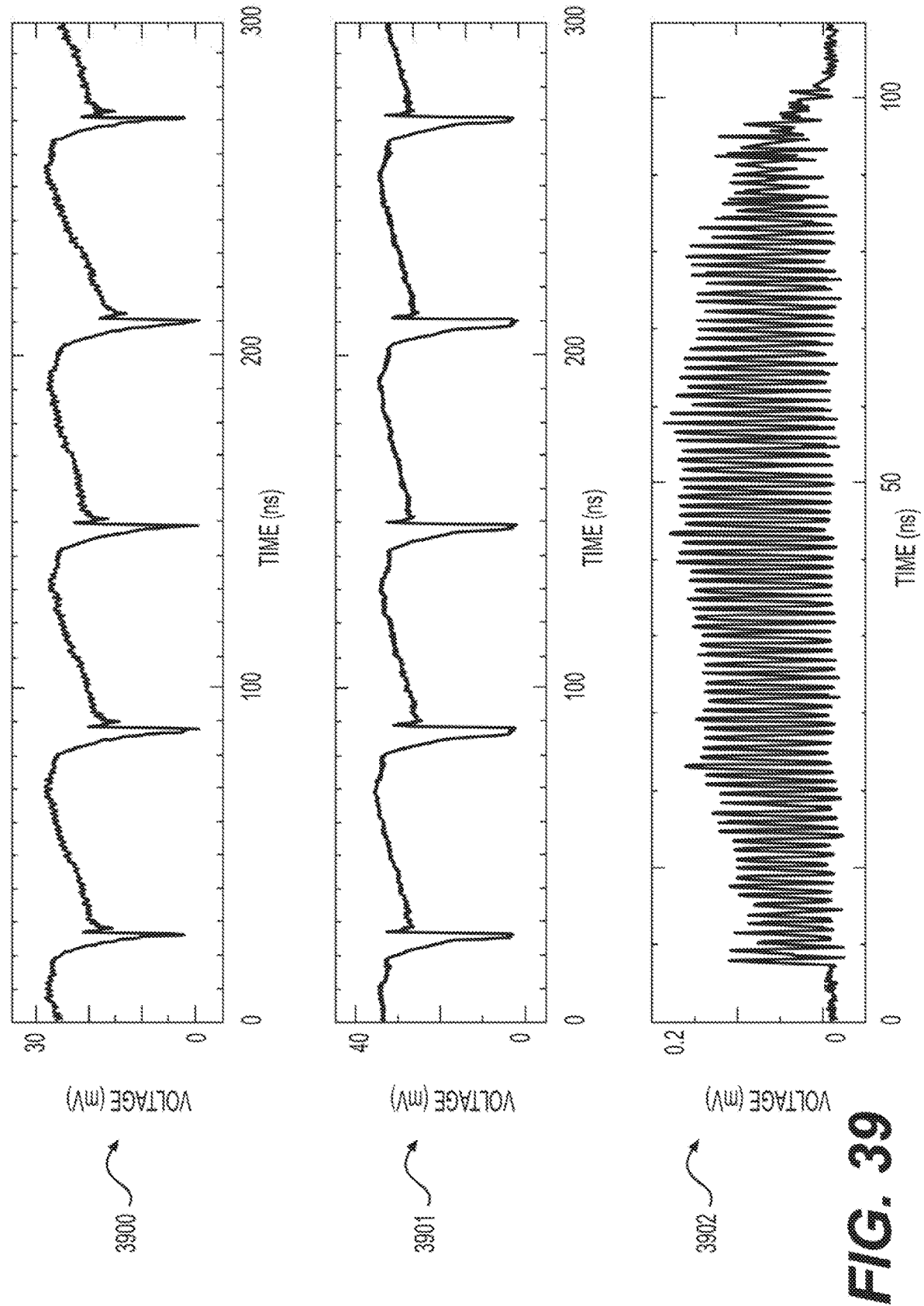
FIG. 39 is a set of graphs providing an exemplary measurement of the temporal output of the exemplary OS-OCT source according to an exemplary embodiment of the present disclosure.

FIG. 39 shows a set of graphs providing an exemplary measurement of the temporal output of the exemplary OS-OCT source according to an exemplary embodiment of the present disclosure. In particular, as illustrated in FIG. 39, output traces of the laser measured with an 8 GHz photoreceiver and a 2 GHz oscilloscope for continuous (3900) and frequency comb (3901) configurations are provided. In the exemplary frequency comb configuration, the EOM can be driven with a 525 ps electrical pulse, and the CFBG dispersion at 1550 nm was 930 ps/nm yielding an approximately 600 ps separation between 80 GHz spaced pulses. This pulse structure is difficult to detect due in part to 2 GHz oscilloscope bandwidth. A second CFBG can be provided to stretch the laser output post-cavity (without copy-and-paste buffering) to further separate the optical pulses in the time-domain 3902.

Figure 40:
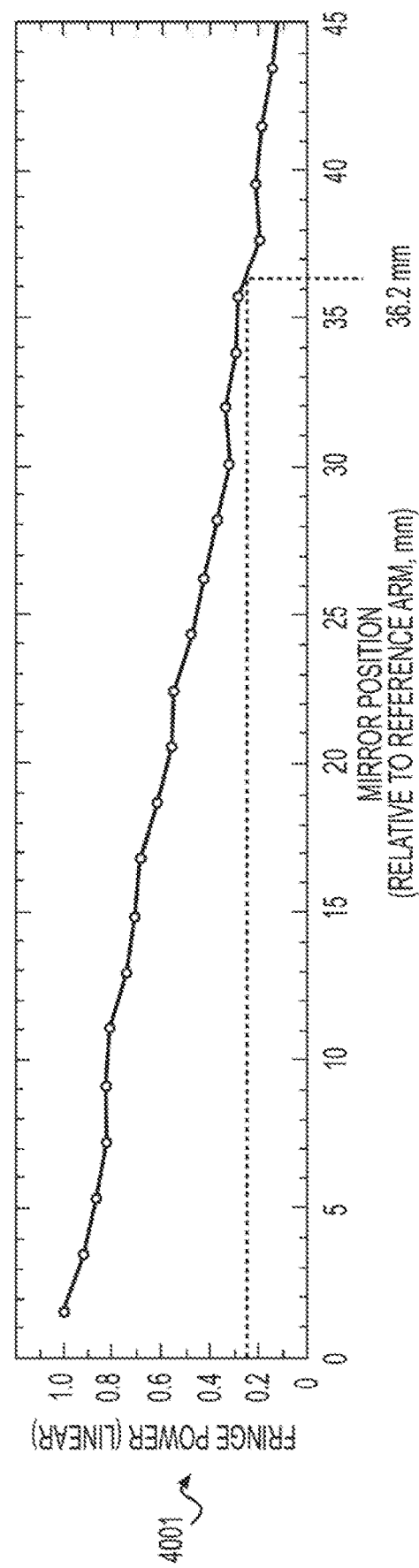
FIG. 40 is a set of graphs providing an exemplary measurement of the coherence length of the exemplary OS-OCT source according to an exemplary embodiment of the present disclosure.
Figure 40:
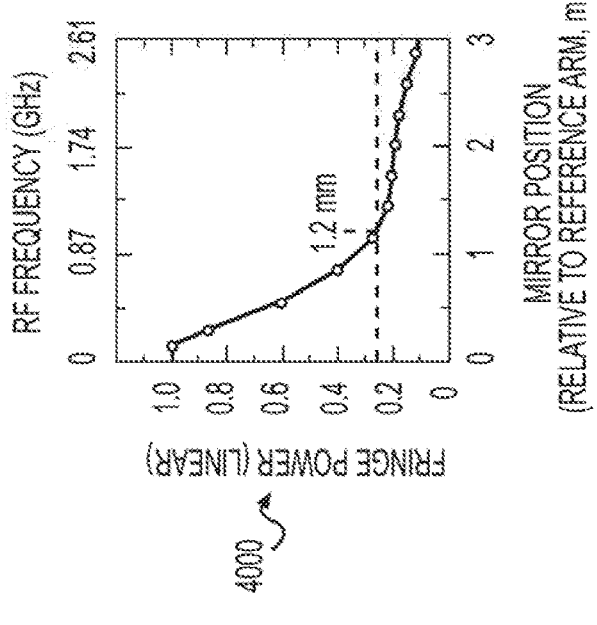

FIG. 40 illustrates a set of graphs providing an exemplary measurement of the coherence length of the exemplary OS-OCT source according to an exemplary embodiment of the present disclosure, including the coherence properties of the continuously swept and frequency comb configurations. For each such exemplary configurations, the laser was output to a Mach-Zehnder interferometer to generate interference fringes. For the continuous wavelength swept configuration 4000, this fringe signal was detected using the 8 GHz photoreceiver and the fringe amplitude was measured using an RF spectrum analyzer. The fringe amplitude was measured as a function of mirror position relative to the zero delay point. Because the frequency comb configuration generates RF frequencies within a confined baseband, an 800 MHz photoreceiver and a high-speed digitizer can be used running above 1 GS/sec to capture fringes as a function of mirror position. The reference arm measurement was subtracted from these fringes and the amplitude of the fringe was calculated as a function of mirror position. As shown in 4001, the frequency comb configuration provided much longer coherence lengths.

Figure 41:
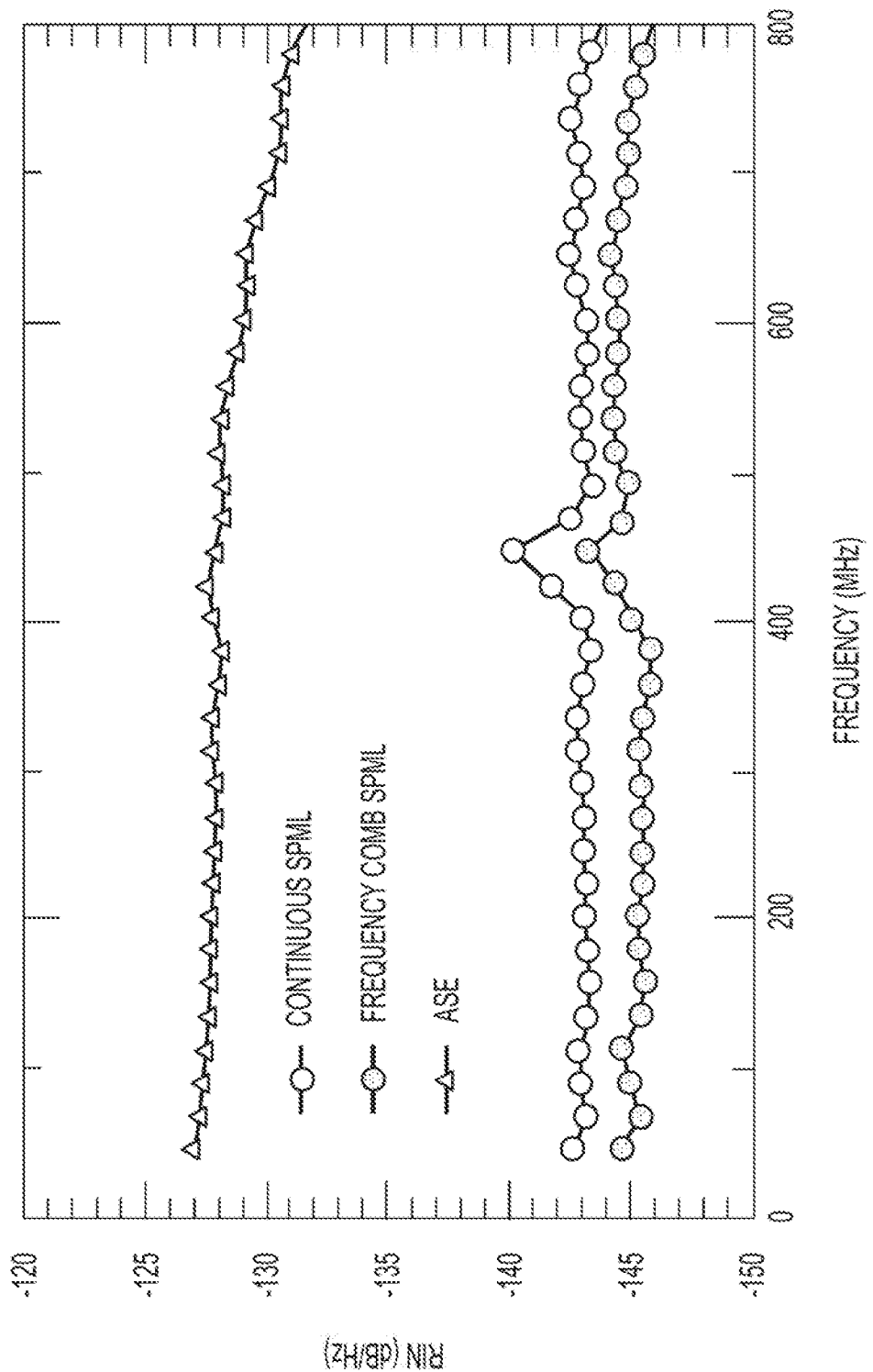
FIG. 41 is a graph providing an exemplary measurement of the noise of the exemplary OS-OCT source according to an exemplary embodiment of the present disclosure.

FIG. 41 shows a graph providing an exemplary measurement of the noise of the exemplary OS-OCT source according to an exemplary embodiment of the present disclosure, including the relative intensity noise (RIN) of the laser sources. The RIN was measured using an 800 MHz photoreceiver and a greater than 2 GS/sec digitizer. RIN levels of −140 dB/Hz and −145 dB/Hz for the continuously swept and frequency comb lasers are obtained.

The foregoing merely illustrates the principles of the present disclosure. Various modifications and alterations to the described embodiments will be apparent to those skilled in the art in view of the teachings herein. Indeed, the arrangements, systems and methods according to the exemplary embodiments of the present disclosure can be used with and/or implement any OCT system, OFDI system, SD-OCT system, SECM system, OBM system or other imaging systems capable of imaging in vivo or fresh tissues, and for example with those described in International Patent Application PCT/US2004/029148, filed Sep. 8, 2004 which published as International Patent Publication No. WO 2005/

047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, U.S. Patent Publication No. 2002/0122246, published on May 9, 2002, U.S. Patent Application No. 61/649,546, U.S. patent application Ser. No. 11/625,135, U.S. Patent Application No. 61/589,083, and International Application No. PCT/US2014/048256, the disclosures of which are incorporated by reference herein in their entireties. It will thus be appreciated that those skilled in the art will be able to devise numerous systems, arrangements and methods which, although not explicitly shown or described herein, embody the principles of the present disclosure and are thus within the spirit and scope of the present disclosure. Further, various exemplary embodiments described herein can be interchangeably used with all other exemplary described embodiments, as should be understood by those having ordinary skill in the art. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus for collecting interferometric information, comprising:
   an analog to digital converter (ADC) having an input,
      the input being configured to receive an interferometric fringe signal from a sample, and
      the ADC being configured to digitize the interferometric fringe signal to produce a first digital value having a first number of bits of resolution; and
   an averaging engine comprising a storage register configured to store a second digital value having a second number of bits of resolution greater than the first number of bits of resolution,
      the averaging engine being configured to:
         receive the first digital signal from the ADC, and
         calculate a third digital signal having the second number of bits of resolution,
            the third digital signal being based on the first digital signal and the second digital signal.

2. The apparatus of claim 1, wherein the first number of bits of resolution is 8.

3. The apparatus of claim 1, wherein the second number of bits of resolution is one of 10, 12, 14, or 16.

4. The apparatus of claim 3, wherein the second number of bits of resolution is 16.

5. The apparatus of claim 1, wherein the ADC and the averaging engine are implemented on a field programmable gate array.

6. The apparatus of claim 1, wherein the interferometric fringe signal comprises an A-line generated by an interferometric imaging apparatus,
   wherein the apparatus comprises a plurality of averaging engines including the averaging engine, and
   wherein the ADC is further configured to:
      digitize the interferometric fringe signal to produce a plurality of digital values each having the first number of bits of resolution, and
      transmit each of the plurality of digital values to a different one of the plurality of averaging engines.

7. The apparatus of claim 6, wherein a number of the plurality of digital values generated by the ADC when digitizing the A-line is equal to a number of the plurality of averaging engines.

8. The apparatus of claim 1, wherein the interferometric fringe signal is based on at least one laser source,
   wherein the ADC comprises a clock that is synchronized to an output of the at least one laser source.

9. A method for collecting interferometric information, comprising:
   receiving, by an input of an analog to digital converter (ADC), an interferometric fringe signal from a sample;
   digitizing, by the ADC, the interferometric fringe signal to produce a first digital value having a first number of bits of resolution;
   receiving, by an averaging engine, the first digital signal from the ADC,
   storing, by a storage register of the averaging engine, a second digital value having a second number of bits of resolution greater than the first number of bits of resolution; and
   calculating, by the averaging engine, a third digital signal having the second number of bits of resolution,
      the third digital signal being based on the first digital signal and the second digital signal.

10. The method of claim 9, wherein digitizing the interferometric fringe signal to produce a first digital value having a first number of bits of resolution further comprises:
   digitizing the interferometric fringe signal to produce a first digital value having a 8 bits of resolution.

11. The method of claim 9, wherein storing a second digital value having a second number of bits of resolution further comprises:
   storing a second digital value having one of 10, 12, 14, or 16 bits of resolution.

12. The method of claim 11, wherein storing a second digital value having a second number of bits of resolution further comprises:
   storing a second digital value having 16 bits of resolution.

13. The method of claim 9, wherein the ADC and the averaging engine are implemented on a field programmable gate array.

14. The method of claim 9, wherein the interferometric fringe signal comprises an A-line generated by an interferometric imaging apparatus,
   wherein the apparatus comprises a plurality of averaging engines including the averaging engine, and
   wherein the method further comprises:
      digitizing, by the ADC, the interferometric fringe signal to produce a plurality of digital values each having the first number of bits of resolution, and
      transmitting, by the ADC, each of the plurality of digital values to a different one of the plurality of averaging engines.

15. The method of claim 14, wherein a number of the plurality of digital values generated by the ADC when digitizing the A-line is equal to a number of the plurality of averaging engines.

16. The method of claim 9, wherein the interferometric fringe signal is based on at least one laser source, and
   wherein the method further comprises:
      synchronizing a clock of the ADC to an output of the at least one laser source.

* * * * *